United States Patent [19]
Bluestone

[11] Patent Number: 6,143,297
[45] Date of Patent: Nov. 7, 2000

[54] METHODS OF PROMOTING IMMUNOPOTENTIATION AND PREPARING ANTIBODIES WITH ANTI-CD3 ANTIBODIES

[75] Inventor: Jeffery A. Bluestone, Chicago, Ill.

[73] Assignee: Arch Development Corporation, Chicago, Ill.

[21] Appl. No.: 08/458,462

[22] Filed: Jun. 2, 1995

Related U.S. Application Data

[62] Division of application No. 08/286,805, Aug. 5, 1994, and a continuation of application No. 07/990,553, Dec. 14, 1992, abandoned, which is a continuation of application No. 07/524,304, May 16, 1990, abandoned, which is a continuation of application No. 07/429,729, Oct. 27, 1989, abandoned.

[51] Int. Cl.[7] .......................... A61K 39/00; A61K 39/395
[52] U.S. Cl. ..................................... 424/184.1; 424/130.1; 424/141.1; 424/143.1; 424/144.1; 424/154.1; 424/173.1; 424/178.1; 424/182.1; 424/184.1; 424/185.1; 424/193.1
[58] Field of Search .............................. 424/184.1, 185.1, 424/178.1, 130.1, 144.1, 193.1, 182.1, 141.1, 154.1, 173.1

[56] References Cited

U.S. PATENT DOCUMENTS

| | | |
|---|---|---|
| 4,079,126 | 3/1978 | Homma et al. . |
| 4,221,794 | 9/1980 | Simon et al. . |
| 4,361,549 | 11/1982 | Kung et al. . |
| 4,395,394 | 7/1983 | Wolff et al. . |
| 4,515,893 | 5/1985 | Kung et al. . |
| 4,658,019 | 4/1987 | Kung et al. . |
| 4,676,980 | 6/1987 | Segal et al. . |
| 4,695,624 | 9/1987 | Marburg et al. . |
| 4,830,852 | 5/1989 | Marburg et al. . |
| 4,882,317 | 11/1989 | Marburg et al. . |
| 4,882,424 | 11/1989 | Schlossman et al. . |
| 5,078,998 | 1/1992 | Bevan et al. . |
| 5,093,241 | 3/1992 | Bennett et al. . |
| 5,225,538 | 7/1993 | Capon et al. . |
| 5,691,449 | 11/1997 | Paradiso et al. . |
| 5,709,862 | 1/1998 | Anderson et al. . |

FOREIGN PATENT DOCUMENTS

| | | |
|---|---|---|
| 0172107 | 2/1986 | European Pat. Off. . |
| 336 379 | 10/1989 | European Pat. Off. . |
| 440 373 | 8/1991 | European Pat. Off. . |
| 613 944 | 9/1994 | European Pat. Off. . |
| 90916853.6-2116 | 2/1995 | European Pat. Off. . |
| 60-248622 | 12/1985 | Japan . |
| WO 89/06974 | 8/1989 | WIPO . |
| WO 89/12458 | 12/1989 | WIPO . |
| WO 90/03985 | 4/1990 | WIPO . |
| WO 90/05541 | 5/1990 | WIPO . |
| WO 91/01143 | 2/1991 | WIPO . |
| WO 91/04053 | 4/1991 | WIPO . |
| WO 91/09968 | 7/1991 | WIPO . |
| WO 92/00092 | 1/1992 | WIPO . |
| WO 92/15671 | 9/1992 | WIPO . |
| WO 93/00431 | 1/1993 | WIPO . |
| WO 93/19767 | 10/1993 | WIPO . |
| WO 93/25712 | 12/1993 | WIPO . |
| WO 94/23760 | 10/1994 | WIPO . |
| WO 94/28027 | 12/1994 | WIPO . |
| WO 94/28912 | 12/1994 | WIPO . |
| WO 95/03408 | 2/1995 | WIPO . |
| WO 95/05464 | 2/1995 | WIPO . |

OTHER PUBLICATIONS

Sultzer and Craig, "Immunomodulation by proteins of *Bordetella pertussels*," *Chemical Abstracts*, 107(15):32, Abstract#126693z, 1987.

Tamura et al., "Protection against influenza virus infection by vaccine inoculated intranasally with cholera toxin B subunit," *Vaccine*, 6(5):409–413, 1988.

Rammensee et al. Eur. J. Immunol. 17: 433–436 (1987).

Ellenhorn et al. Science 242: 569–574 (1988).

Dresser in Weir (ed.) Handbook of Experimental Immunology Fourth Edition Blackwell Scientific Publications, Oxford (1986) pp. 8.1–8.21.

Edwin, C. et al. Applied and Environmental Microbiology 48: 1171–1175, Dec. 1984.

Giardina, S. L. et al. Journal of Immunological Methods 89 (1): 1–7, May 1986.

Harlow, E. et al. Antibodies: A Laboratory Manual, Cold Spring Harbor Laboratory, Cold Spring Harbor, N Y, pp. 72–77, 92–97, 128–135, 141–157, 1988.

Weir, D.M. et al. Handboodk of Experimental Immunology, Blackwell Scientific Publications, Boston, MA, vol. 4, pp. 8.6–8.7, 1986.

Asano, Y., Singer, A., and Hodes, R., "Role of the Major Histo–compatibility Complex in T Cell Activation of B Cell Sub–populations." *Journal of Experimental Medicine*, vol. 154 (Oct. 1981), pp. 1100–1115.

(List continued on next page.)

*Primary Examiner*—Christina Y. Chan
*Assistant Examiner*—Phillip Gambel
*Attorney, Agent, or Firm*—Fulbright & Jaworski

[57] ABSTRACT

Disclosed are immunopotentiating agents, and vaccines thereof, which enhance and/or otherwise modify immune responses, and method for their preparation and use in vivo. Immunopotentiating agents can be single agents that act directly, adjuvants added concurrently with the agents, or heteroconjugates wherein the immunopotentiating agent is chemically coupled to the compound against which an immune response is desired. Examples of immunopotentiating agents include monoclonal antibodies, such as anti-CD3, anti-CD2) and anti-CD5 antibodies, and proteins derived from microorganisms (e.g., enterotoxins) which activate T cells. The compounds against which an immune response can be generated, which may be the second component in a heteroconjugate, include compound from abnormal or diseased tissues such as tumors, or infectious agents, such as viruses, bacteria, fungi, protozoal or metozoal parasites, and can be obtained by natural or recombinant means. Methods of using the invention to prepare monoclonal antibodies are particularly disclosed.

27 Claims, 15 Drawing Sheets

OTHER PUBLICATIONS

Bayer, E. and Wilchek, M. "The Use of the Avidin–Biotin Complex as a Tool in Molecular Biology." in: *Methods of Bio–chemical Analysis*, vol. 26 (1980), pp. 1–45.

Bluestone, J., Hirsch, R., and Ellenhorn J., "In Vivo Administration of Monoclonal Anti–T Cell Antibodies Can Activate Immune Responses and Prevent Malignant Progressive Tumor Growth." Presented at U.S. Japan Cooperative Program in Cancer Research, Honolulu, Hawaii (Jan. 1989).

Bluestone, J., Hirsch, R., and Ellenhorn, J., "Tumor Specific Immunity Augmented by Anti–CD3 Treatment." Presented at the Princess Taketmatsu Cancer Research Symposium (Nov. 1988).

Carlsson, J., Drevin, H., Axen, R., "Protein Thiolation and Reversible Protein–Protein Conjugation." *Biochemistry Journal*, vol. 173 (1978), pp. 723–737.

"CD Guide 1989: Workshop on Human Leucocyte Differentiation Antigens." *Immunolgy Today*, vol. 10, No. 8 (1989), pp. 254–255.

Cease, K., Berkower, I., York–Jolley, J., et al., "T Cell Clones Specific for an Amphipathic Alpha–Helical Region of Sperm Whale Myoglobin Show Differing Fine Specificities for Synthetic Peptides." *Journal of Experimental Medicine*, vol. 164 (Nov. 1986), pp. 1779–1784.

Cease, K., Margalit, H., Cornette, J., et al., "Helper T–Cell Antigenic Site Identification in the Acquired Immunodeficiency Syndrome Virus gp120 Envelope Protein and Induction of Immunity in Mice to the Native Protein Using a 16–Residue Synthetic Peptide." *PNAS* (USA), vol. 84 (Jun. 1987). pp. 4249–4253.

Cumber, A., Forrester, J., Foxwell, B., et al., "Preparation of Antibody–Toxin Conjugates." in: *Methods of Enzymology*, vol. 112 (Academic Press, Inc., 1985), pp. 207–217.

Ellenhorn, J., Hirsch, R., Hartley, J., et al., "Dose–Dependent Activation of Murine T Cells Following In Vivo Administration of Anti–Murine CD3." Transplantation Proceedings, vol. 21, No. 1 (Feb. 1989), pp. 1013–1014.

Ellenhorn, J., Schreiber, H., and Bluestone, J., "Mechanism of Tumor Rejection in Anti–CD3 Mab Treated Mice." *Journal of Immunology*, vol. 144 (1990), pp. 2840–2846.

Friend, S., "Anti–T Cell Antibodies as Adjuvants for Immunization." *Faseb Journal*, 73rd Annual Meeting of Federation of American Society for Experimental Biology, Mar. 19–23, 1989, in New Orleans.

Gallo, R., "HIV—The Cause of AIDS: An Overview on Its Biology, Mechanisms of Disease Induction, and Our Attempts to Control It." *Journal of Acquired Immune Deficiency Syndromes*, vol. 1 No. 6 (1988), pp. 521–535.

Glennie, M., McBride, H., Worth, A., et al., "Preparation and Performance of Bispecific F (ab'gamma)$_2$ Antibody Containing Thioether–Linked Fab'gamma Fragments." *Journal of Immunology*, vol. 139, No. 7 (Oct. 1, 1987), pp. 2367–2375.

Goldstein, G., "Overview of the Development of ORTHOCLONE OKT3: Monoclonal Antibody for Therapeutic Use of Transplantation." Transplantation Proceedings, vol. XIX, No. 2, Suppl. 1 (Apr. 1987), pp. 1–6.

Green, N. "Avidin." in: Afinsen, C., et al. (eds.), *Adv. in Prot.* vol. 29 (1975), pp. 85–133.

Gunter, K., Malek, T., and Shevach, E., "T Cell–Activating Properties of an Anti–Thy–1 Monoclonal Antibody." *Journal of Experimental Medicine*, vol. 159 (Mar. 1984), pp. 716–730.

Hirsch, R., Chatenoud, L., Gress, R., et al, "Suppression of the Humoral Response to Anti–CD3 Monoclonal Antibody." *Transplantation*, vol. 47, No. 5 (May 1989), pp. 853–857.

Hirsch, R., Chatenoud, L., Gress, R., et al. "Suppression of the Humoral Response to Anti–CD3 mAB by Pretreatment with Anti–CD4 mAB." Transplantation Proceedings, vol. 21, No. 1 (Feb. 1989) pp. 1015–1016.

Hirsch, R., Eckhaus, M., Auchincloss, H., et al., "Effects of In Vivo Administration of Anti–T3 Monoclonal Antibody on T Cell Function in Mice." *Journal of Immunology*, vol. 140, No. 11 (Jun. 1, 1988), pp. 3766–3772.

Hirsch, R., Gress, R., Pluznik, D., et al., "Effects of In Vivo Administration of Anti–CD3 Monoclonal Antibody on T Cell Function in Mice." *Journal of Immunology*, vol. 142, No. 3 (Feb. 1, 1989), pp. 737–743.

Hoffman, R., Bluestone, J., Leo, O., et al., "Lysis of Anti–T3–Bearing Murine Hybridoma Cells by Human Allospecific Cytotoxic T Cell Clones and Inhibition of That Lysis by Anti–T3 and Anti–LFA–1 Antibodies." *Journal of Immunology*, vol. 135, No. 1 (Jul. 1985), pp. 5–8.

International Search Report for corresponding PCT/US 90/06177.

Krieger, J., Jenis, D., Chesnut, R., et al., "Studies on the Capacity of Intact Cells and Purified Ia from Different B Cell Sources to Function in Antigen Presentation to T Cells." *Journal of Immunology*, vol. 140, No. 2 (Jan. 15, 1988), pp. 388–394.

Kronenberg, M., Siv, G., Hood, L., et al., "The Molecular Genetics of the T–Cell Antigen Receptor and T–Cell Antigen Recognition." *Ann. Rev. Immunol.*, vol. 4 (1986), pp. 529–591.

Leo, O., Foo, M., Henkart, P., et al., "Role of Accessory Molecules in Signal Transduction of Cytolytic T Lymphocyte by Anti–T Cell Receptor and Anti–Ly–6.2C Monoclonal Antibodies." *Journal of Immunology*, vol. 139, No. 11 (Dec. 1, 1987) pp. 3556–3563.

Leo, O., Foo, M., Sachs, D., et al., "Identification of a Monoclonal Antibody Specific for a Murine T3 Polypeptide." *PNAS* (USA), vol. 84 (Mar. 1987), pp. 1374–1378.

Leo, O., Foo, M., Segal, D., et al., "Activation of Murine T Lymphocytes with Monoclonal Antibodies: Detection on Lyt–2+ Cells of an Antigen Not Associated with the T Cell Receptor Complex But Involved in T Cell Activation." *Journal of Immunology*, vol. 139, No. 4 (Aug. 15, 1987), pp. 1214–1222.

Leo, O., Sachs, D., Samelson, L., et al., "Identification of Monoclonal Antibodies Specific for the T Cell Receptor Complex by FC Receptor–Mediated CTL Lysis." *Journal of Immunology*, vol. 137, No. 12 (Dec. 15, 1986), pp. 3874–3880.

Merrifield, R., "Synthesis of a Tetrapeptide." *Journal of American Chemical Society*, vol. 85 (Jul. 20, 1963), pp. 2149–2154.

Meuer, S., Hodgdon, J., Hussey, R., et al., "Antigen–Like Effects of Monoclonal Antibodies Directed at Receptors on Human T Cell Clones." *Journal of Experimental Medicine*, vol. 158 (Sep. 1983), pp. 988–993.

Nelson, P., Cosimi, A., Delmonico, F., et al., "Antithymocyte Renal Allograft Globulin as the Primary Treatment for Rejection." *Transplantation*, vol. 36, No. 5 (Nov. 1983), pp. 587–589.

Rosenberg, S., Lotze, M., Muul, L., et al., "A Progress Report on the Treatment of 157 Patients with Advanced Cancer Using Lymphokine–Activated Killer Cells and Interleukin–2 or High–Dose Interleukin–2 Alone." *New England Journal of Medicine,* vol. 316, No. 15 (Apr. 9, 1987), pp. 889–897.

Saito, T., Weiss, A., Miller, J., et al., "Specific Antigen–IA Activation of Transfected Human T Cells Expressing Murine Ti AlphaBeta–Human T3 Receptor Complexes." *Nature,* vol. 325 (Jan. 8, 1987), pp. 125–130.

Samelson, L., Germain, R., and Schwartz, R., "Monoclonal Antibodies Against the Antigen Receptor on a Cloned T–Cell Hybrid." *PNAS* (USA), vol. 80 (Nov. 1983), pp. 6972–6976.

Samelson, L., Harford, J., and Klausner,R., "Identification of the Components of the Murine T Cell Antigen Receptor Complex." *Cell,* vol. 43 (Nov. 1985), pp. 223–231.

Shield, C., Cosimi, A., Tolkoff–Rubin, N., et al. "Use of Antithymocyte Globulin for Reversal of Acute Allograft Rejection." *Transplantation,* vol. 28, No. 6 (Dec. 1979), pp. 461–464.

Starzl, T., Marchioro, T., Porter, K., et al., "The Use of Heterologous Antilymphoid Agents in Canine Renal and Liver Momotransplantation and in Human Renal Homotransplantation." *Surgery, Gynecology & Obstetrics* (Feb. 1967), pp. 301–318.

Strauss, H., Van Waes, C., Fink, M., et al., "Identification of a Unique Tumor Antigen as Rejection Antigen by Molecular Cloning and Gene Transfer." *Journal of Experimental Medicine,* vol. 164 (Nov. 1986), pp. 1516–1530.

Sussman, J., Bonifacino, J., Lippincott–Schwartz, J., et al., "Failure to Synthesize the T Cell CD3–1 Chain: Structure and Function of a Partial T Cell Receptor Complex." *Cell,* vol. 52 (Jan. 15, 1988), pp. 85–95.

Takada, S. and Engleman, E., "Evidence for an Association Between CD8 Molecules and the T Cell Receptor Complex on Cytotoxic T Cells." *Journal of Immunology,* vol. 139, No. 10 (Nov. 15, 1987), pp. 3231–3235.

Tam, J., Heath, W., and Merrifield, R., "$S_n2$ Deprotection of Synthetic Peptides with a Low Concentration of HF in Dimethyl Sulfide: Evidence and Application in Peptide Synthesis." *Journal of American Chemical Society,* vol. 105 (1983), pp. 6442–6455.

Topalian, S., Solomon, D., Avis, F., et al., "Immunotherapy of Patients with Advanced Cancer Using Tumor–Infiltrating Lymphocytes and Recombinant Interleukin–2: A Pilot Study." *Journal of Clinical Oncology,* vol. 6, No. 5 (May 1988), pp. 839–853.

Unkeless, J., "Characterization of a Monoclonal Antibody Directed Against Mouse Macrophage and Lymphocte Fc Receptors." *Journal of Experimental Medicine,* vol. 150 (Sep. 1979), pp. 580–596.

Van Waes, C., Urban, J., Rothstein, J., et al. "Highly Malignant Tumor Variants Retain Tumor–Specific Antigens Recognized by T Helper Cells." *Journal of Experimental Medicine,* vol. 164 (Nov. 1986), pp. 1547–1565.

Van Wauwe, J., De Mey,J., and Goossens, J., "OKT3: A Monoclonal Anti–Human T Lymphocyte Antibody with Potent Mitogenic Properties." *Journal of Immunology,* vol. 124, No. 6 (Jun. 1980), pp. 2708–2713.

Weiss, A., Imboden, J., Shoback, D., et al., "Role of T3 Surface Molecules in Human T–Cell Activation: T3–Dependent Activation Results in an Increase in Cytoplasmic Free Calcium." *PNAS* (USA), vol. 81 (Jul. 1984), pp. 4169–4173.

White, J., Herman, A., Pullen, A., et al., "The VBeta–Specific Superantigen Staphylococcal Enterotoxin B: Stimulation of Mature T Cells and Clonal Deletion in Neonatal Mice." *Cell,* vol. 56 (Jan. 13, 1989), pp. 27–35.

Wortzel, R., Phillips, C., and Schreiber, H., "Multiple Tumour–Specific Antigens Expressed on a Single Tumour Cell." *Nature* (Lond.), vol. 304 (Jul. 14, 1983), pp. 165–167.

Ellenhorn, J., Hirsch, R., Schreiber, H., et al. "In vivo administration of monocolonal anti–CD3 antibody prevents malignant progressor tumor growth." *Science,* vol. 242 (1988), pp. 564–571.

Hird et al., "Immunotherapy with Monoclonal Antibodies," *Genes & Cancer,* 1990, pp. 183–189, Carney and Sikora, eds., John Wiley & Sons, Ltd., Chichester, England.

Harris et al., "Therapeutic Antibodies—the Coming of Age," *Tibtech,* 1993, 11:42–44, Feb. 1993.

Roitt et al., *Immunology,* p. 9.9, Gower Medical Publishing, London, England, van den Berghe, ed., 1989.

Carayanniotis and Barber, "Adjuvant–free IgG Responses Induced with Antigen Coupled to Antibodies Against Class II MHC," *Nature,* 327:59–61, 1987.

Cosimi et al., "Prolonged Survival of Nonhuman Primate Renal Allograft Recipients Treated Only with Anti–CD4 Monoclonal Antibody," *Surgery,* 108(2):406–414, 1990.

Harlow and Lane, "Storing and Purifying Antibodies," *Antibodies A Laboratory Manual,* 284–287, 1988.

Jenkins, M.K., et al., "Induction and Maintenance of Anergy in Mature T Cells", *Advances in Experimental Medicine and Biology,* 292:167–176, 1991.

Jenkins, M.K., et al., "CD28 Delivers a Costimulatory Signal Involved in Antigen–specific IL–2 Production by Human T Cells", *The Journal of Immunology,* 147:2461–2466, 1991.

Ortho Multicenter Transplant Study Group, "A Randomized Clinical Trial of OKT3 Monoclonal Antibody for Acute Rejection of Gadaveric Renal Transplants," *The New England Journal of Medicine,* 313(6):337–342, 1985.

Seed, Brian, "An LFA–3 cDNA encodes a phospholipid–linked membrane protein homologous to its receptor CD2," *Nature,* 329:840–842, 1987.

Seed, B. and Aruffo, A., "Molecular cloning of the CD2 antigen, the T–cell erythrocyte receptor, by a rapid immunoselection procedure," *Proc. Natl. Acad. Sci. USA,* 84:3365–3369, 1987.

Wedrychowski et al., "Immune Enhancers Composed o Polyvalent Binding Sites of Anti–CD3 Antibodies," *Bio/Technology,* 11:486–489, 1993.

Richards et al., "Phase IB Evaluation of OKT3," 82nd Annual Meeting of the American Association for Cancer Research, Houston, Texas, USA, May 15–18, 1991.

Woodle et al., "Humanized OKT3 Antibodies: Successful Transfer of Immune Modulating Properties and Idiotype Expression," *The Journal of Immunology,* 148:2756–2763, May 1992.

Barnes, "The CD4 Receptor's Changing Role," *J. NIH Research,* 1:30, 50–52, May/Jun. 1989.

Kappler et al., "Vbeta–Specific Stimulation of Human T Cells by Staphylococcal Toxins," *Science,* 244(4906):811–813, May 1989.

Langlet et al., "Role of Ti/CD3, Thy–1, and Ly–6 in Cytolytic T–Cell Activation Analyzed with Ti Loss Variants," *In: Cytotoxic T Cells: biology and Relevance to Diseases,* Battisto et al. (Eds.), Ann Ny Acad Sci, 532:33–43, 1988.

Putney et al., "HTLV–III/Lav–Neutralizing Antibodies to an *E. Coli*–Produced Fragment of the virus Envelope," *Science*, 234:1392–1395, Dec. 1986.

Robey et al., "Prospect for Prevention of Human Immunodeficiency Virus Infection: Purified 120–kDa Envelope Glycoprotein Induces Neutralizing Antibody," *PNAS USA*, 83:7023–7027, Sep. 1986.

Hirsch et al., "In Vivo Administration of Anti–CD3 Monoclonal Antibody Can Activate Immune Responses Thus Preventing Malignant Tumor Growth," *In: Immune System and Cancer*, Hamaoka et al. (Eds.), Japan Sci. Soc. Press, Tokyo/Taylor & Francis, LTD., pp. 239–245, 1989.

Hirsch et al., "Anti–CD3 Antibody for Autoimmune Disease, A Cautionary Note," *Lancet*, 1:1390, Jun. 1989.

Ferran et al., "Cytokine Related Syndrome Following Injection of Anti–CD3 Monoclonal Antibody: Further Evidence for Transient In Vivo T Cell Activation," *Eur. J. Immunol.*, 20:509–515, 1990.

Kast et al., "Treatment with Monoclonal Anti–CD3 Antibody Projects Against Lethal Sendai Virus Infection by Induction of NK Cells," *Journal of Immunology*, 145(7):2254–2259, Oct. 1990.

Ellenhorn et al., "Activation of Human T Cells In Vivo Following Treatment of Transplant Recipients with OKT3," *Transplantation*, 50(4):608–612, Oct. 1990.

Ferran et al., "Reduction of Morbidity and Cytokine Release in Anti–CD3 moAb–Treated Mice by Corticosteroids," *Transplantation*, 50(4):642–648, Oct. 1990.

Newell et al., "In Vivo T Cell activation by Staphylococcal Entertoxin B Prevents Outgrowth of a Malignant Tumor," *PNAS USA*, 88:1074–1078, Feb. 1991.

Woodle et al., "T–Cell Activation and Lymphokine Production Induced by Antihuman CD3 Monoclonal Antibodies," *Transplantation Proceedings*, 23:81–82, Feb. 1991.

Newell et al., "Immunopotentition of Anti–Viral and Anti–Tumor Imjmune Responses Using Anti–T Cell Receptor Antibodies and Mitogens," *NY Acad. Sci.*, Oct. 22–24, 1990.

Woodle et al., "Anti–CD3 Monoclonal Antibody Therapy: An Approach Toward Optimization by In Vitro Analysis of New Anti–CD3 Antibodies," *Transplantation*, 52(2):361–368, Aug. 1991.

Woodle et al., "OKT3 F (ab')$^2$ Fragments Retention of the Immunosuppressive Properties of Whole Antibody with Marked Reduction in T Cell Activation and Lymphokine Release," *Transplantation*, 52(2):354–360, Aug. 1991.

Male et al., *Advanced Immunology*, Hadjidimitriadou (Ed.), London: Gower Medical Publishing, pp. 11.8–11.9, 1987.

Geppert et al., "Accessory Cell Independent Proliferation of Human T4 Cells Stimulated by Immobilized Monoclonal Antibodies to CD3," *J. Immunol*, 138(6):1660–1666, Mar. 1987.

Adair et al., "Humanization of the Murin Anti–Human CD3 Monoclonal Antibody OKT3," *Hum. Antibodies Hybridomas*, 5(1&2):41–47, 1994.

Alegre et al., "A Non–Activating 'Humanized' Anti–CD3 Monoclonal Antibody Retains Immunosuppressive Properties In Vivo," *Transplantation*, 57(11):1537–1543, Jun. 1994.

Alegre et al., "In vitro and In Vivo Properties of 'Humanized' Anti–CD3 Monoclonal Antibodies with Different Affinities for Fc Receptor," *8th International Congress of Immunology*, Aug. 23–28, 1992.

Alegre et al., "Effect of a Single Amino Acid Mutation in nthe Fc Portion of a 'Humanized' OKT3 on T Cell Responses In Vitro," *J. Am. Soc. Nephol.*, 2(3):S30, 1991.

Alegre et al., "Effect of a Single Amino Acid Mutation on the Activating and Immunosuppreassive Properties of a 'Humanized' OKT3 Monoclonal Antibody," *The Journal of Immunology*, 148(11):3461–3468, Jun. 1992.

Alegre et al., "Cytokine Release Syndrome Induced by the 145–2C11 Anti–CD3 Monoclonal Antibody in Mice: Prevention by High Doses of Methylprednisolone," *The Journal of Immunology*, 146(4):1184–1191, Feb. 1991.

Alegre et al., "In Vitro and In Vivo Properties of 'Humanized' Anti–CD3 Monoclonal Antibodies with Different Affinities for Fc Receptor," submitted to FASEB Summer Conference, Jun. 1993.

Archer et al., "Inverse Relationship Between Immune Interferon Induction and Mitogen Effects on the Maturation of the Primary Antibody Response," *Immunopharmacology*, 3:71–81, 1981.

Aruffo et al., "Molecular Cloning of a CD28 cDNA by a High–Efficiency COS Cell Expression System," *Proc Natl Acad Sci USA*, 84:8573–8577, Dec. 1987.

Azuma et al., "B70 Antigen is a Second Ligand for CTLA–4 and CD28," *Nature*, 366:76–79, Nov. 1993.

Azuma et al., "Involvement of CD28 in MHC–Unrestricted Cytotoxicity Mediated by a Human Natural Killer Leukemia Cell Line," *The Journal of Immunology*, 149:1115–1123, Aug. 1992.

Beyers et al., Activation of T Lymphocytes via Monoclonal Antibodies Against Rat Cell Surface Antigens with Particular Reference to CD2 Antigen, *Immunological Reviews*, 111:59–77, 1989.

Bierer and Burakoff, T–Lymphocyte Activation: The Biology and Function of CD2 an dCD4, *Immunological Reviews*, 111:276–293, 1989.

Bolt et al., "The Generation of a Humanized, Non–Mitogenic CD3 Monoclonal Antibody which Retains In Vitro Immunosuppressive Properties," *Eur J Immunol*, 23:403–4111, 1993.

Boussiotis et al., "Activated Human B Lymphocytes Express Three CTLA–4 Counterreceptors that Costimulate T–Cell Acitvation," *Proc Natl Acad Sci, USA*, 90:11059–11063, Dec. 1993.

Boussiotis et al., "B7 But Not Intercellular Adhesion Molecule–1 Costimulation Prevents the Induction of Human Alloantigen–Specific Tolerance," *J. Exp. Med*, 178:1753–1763, Nov. 1993.

Burton, "Immunoglobin G: Functional Sites," *Molecular Immunology*, 22(3):161–206, 1985.

Chang et al., "Does OKT3 Monoclonal Antibody React with an Antigen–Recognition Structure on Human T Cells?" *Proc Natl Acad Sci USA*, 78(3):1805–1808, Mar. 1981.

Chatenoud et al., "Systemic Reacton to the Anti–T–Cell Monoclonal Antibody OKT3 in Relation to Serum Levels of Tumor Necrosis Factor and Interferon–α," *The New England Journal of Medicine*, 320(21):1420–1421, May 1989.

Chen et al., "Costimulation of T Cells for Tumor Immunity," *Immunology Today*, 14(10):483–486, Sep. 1993.

Danbolt et al., "Purification and Reconstitution of the Sodium– and Potassium–Coupled Glutamate Transport Glycoprotein from Rat Brain," *Biochemistry*, 29:6734–6740, 1990.

DeVries et al., "Interplay Between the TCR/CD3 Complex and CD4 or CD8 in the Activation of Cytotoxic T Lymphocytes," *Immunological Reviews*, 109:119–141, 1989.

Duncan et al., "Localization of the Binding Site for the Human High–Affinity Fc Receptor on IgG," *Nature*, 332:563–564, Apr. 1988.

Emmrich et al., "Cross–Linking of the T Cell Receptor Complex wiht the Subset–Specific Differentiation Antigen Stimulates Interleukin 2 Receptor Expression in Human CD4 and CD8 T Cells" *Eur J Immunol*, 17:529–534, 1987.

Flens et al., "Efficient Expansion of Tumor–Infiltrating Lymphocytes from Solid Tumors by Stimulation with Combined CD3 and CD28 Monoclonal Antibodies," *Cancer Immunol Immunother*, 37:323–328, 1993.

Fraser et al., "Regulation of Interleukin–2 Gene Enhancer Activity by the T Cell accessory Molecule CD28," *Science*, pp. 313–316, Jan. 1991.

Freedman et al., "Selective Induction of B7/BB–1 on Interferon–$\gamma$ Stimulated Monocytes: A Potential Mechanism for Amplification of T Cell Activation Through the CD28 Pathway," *Cellular Immunology*, 137:429–437, 1991.

Freeman et al., "Uncovering of Functional Alternative CTLA–4 Counter–Receptor in B7–Deficinet Mice," *Science*, 262:907–909, 1993.

Freeman et al., "Murine B7–2, An Alternative CTLA4 Conter–Receptor that Costimualtes T Cell Proliferation and Interleukin 2 Production," *The Journal of Experimental Medicine*, 178:2185–2192, Dec. 1993.

Freeman et al., "Cloning of B7–2: A CTLA–4 Counter–Receptor that Costimulates Human T Cell Proliferation," *Science*, 262:909–911, Nov. 1993.

Gabizon et al., "Effect of Liposome Composition and Other Factors on the Targeting of Liposomes to Experimental Tumors: Biodistribution and Imaging Studies," *Cancer Research*, 50:6371–6378, Oct. 1990.

Gergely and Sarmay, "The Two Binding–Site Models of Human IgG Binding Fc$\gamma$ Receptors," *The FASEB Journal*, 4:3275–3283, Dec. 1990.

Gimmi et al., "B–Cell Surface Antigen B7 Provides a Costimulatory Signal that Induces T Cells to Proliferate and Secrete Interelukin 2," *Proc Natl Acad Sci USA*, 88:6575–6579, Aug. 1991.

Gross et al., "Identification and Distribution of the Costimulatory Receptor CD23 in the Mouse," *The Journal of Immunology*, 149:380–388, Jul. 1992.

Guerder et al., "Costimulator B7–1 Confers Antigen–Presenting–Cell Function to Parenchymal Tissue and In Conjunction with Tumor Necrosis Factor $\alpha$ Leads to Autoimmunity in Transgenic Mice," *Proc Natl Acad Sci, USA*, 91:5138–5142, May 1994.

Harding and Allison, "AC28–B7 Interactions Allow the Induction of CD8$^+$ Cytotoxic T Lymphocytes in the Absence of Exogenous Help," *J Exp Med*, 177:1791–1796, Jun. 1993.

Harding et al., "CD28–Mediated Signalling Co–Stimulates Murine T Cells and Prevents Induction of Anergy in T–Cell Clones," 356:607–609, Apr. 1992.

Harper et al., "CTLA–4 and CD28 Activated Lymphocyte Molecules are Closely Related in Both Mouse and Human as to Sequence, Message Expresion, Gene Structure, and Chromosomal Location," *The Journal of Immunology*, 147:1037–1044, Aug. 1991.

Havran et al., "Expresssion and Function of the CD3–Antigen Receptor on Murine CD4$^+$8$^+$ Thymocytes," *Nature*, 330(12):170–173, Nov. 1987.

Heath et al., "Autoimmune Diabetes as a Consequence of Locally Produced Interleukin–2," *Nature*, 359:547–549, Oct. 1992.

Janeway, "The T Cell Receptor as a Multicomponent Signalling Machine: CD4/CD8 Coreceptor and CD45 in T Cell Activation," *Annu Rev Immunol*, 10:645–74, 1992.

Jefferis et al., "Molecular Definition of Interaction Sites on Human IgG for Fc Receptors (huFc$\gamma$R)," *Molecular Immunology*, 27(12):1237–1240, 1990.

Jolliffe, "Humanized Antibodies: Enahcing Therapeutic Utility through Antibody engineering," *Intern Rev Immunol*, 10:241–250, 1993.

June et al., "The B7 and CD28 Receptor Families," *Immunol Today*, 15(7):321–331, Jun. 1994.

Lenschow et al., "Expression and Functional Significance of an Additional Ligand for CTLA–4," *Proc Natl Acad Sci USA*, 90:11054–11058, Dec. 1993.

Lenschow et al., "Long–Term Survival of Xenogeneic Pancreatic Islet Grafts Induced by CTLA4lg," *Science*, 257:789–792, Aug. 1992.

Li et al., "Costimulation of Tumor–Reactive CD4$^+$ and CD8$^+$ T Lymphocytes by B7, a Natural Ligand for CD38, Can be sued to Treat Established Mouse Melanoma," *The Journal of Immunology*, 421–428, Jul. 1994.

Lin et al., "Long–Term Acceptance of Major Histocompatibility Complex Mismatched Cardiac Allografts Induced by CTLA4Ig Plus Donor–Specific Transfusion," *J Exp Med*, 178:1801–1806, Nov. 1993.

Lindsten et al., "Characterization of CTLA–4 Structure and Expression on Human T Cells," *The Journal of Immunology*, 151(7):3489–3499, Oct. 1993.

Lindsten et al., "Regulation of Lymphokine Messenger RNA Stability by a Surface–Mediated T Cell Activation Pathway," *Science*, 244:339–343, Apr. 1989.

Linsley et al., "CTLA–4 is a Second Receptor for the B Cell Activation Antigen B7," *J Exp Medi*, 174:561–569, Sep. 1991.

Liu and Linsley, "Costimulation of T–Cell Growth," *Current Opinion in Immunology*, 4:265–270, 1992.

Mannik and Person, "New Antigenic Determinants Revealed on Human IgG by Binding Two Immunoblotting Membranes," *Journal of Immunological Methods*, 144:265–267, 1991.

Newell et al., "Death of Mature T Cells by Separate Ligation for CD4 and the T–Cell Receptor for Antigen," *Nature*, 347:286–289, Sep. 1990.

Nickoloff et al., "Discordant Expression of CD28 Ligands, BB–1, and B7 on Keratinocytes In Vitro and Psoriatic Cells In Vivo," *American Journal of Pathology*, 142(4):1029–1040, Apr. 1993.

Partridge et al., "The Use of Anti–IgG Monoclonal Antibodies in Mapping the Monocyte Receptor Site in IgG," *Molecular Immunology*, 23(12):1365–1372, 1986.

Parlevliet et al., "Anti–CD3 Murine Monoclonal Isotype Switch Variants Tested for Toxicity and Immunologic Monitoring in Four Chimpanzees," *Transplantation*, 50(5):889–892, Nov. 1990.

Razi–Wolf et al., "Expression and Function of the Murine B7 Antigen, the Major Costimulatory Molecule Expressed by Peritoneal Exudate Cells," *Proc Natl Acad Sci, USA*, 89:4210–4214, May 1992.

Reiser et al., "Murine B7 Antigen Provides an Efficient Costimulatory signal for Activation of Murine T Lymphocytes Via theT–Cell Receptor/CD3 Complex," *Proc Natl Acad Sci, USA*, 89:271–275, Jan. 1992.

Robbins and Bergdoll, "Production of Rabbit Antisera to the Staphylococcal Enterotoxins," *Biol Abs,* 78(5):4028, abstract No. 35589, 1984.

Rudd, "CD4, CD8 and the TCR–CD3 Complex: A Novel Class of Protein–Tyrosine Kinase Receptor," *Immunology Today,* 11(11):400–406, 1990.

Rudd et al., "Molecular Interactions, T–Cell Subsets and a Role of the CD4/CD8:p56$^{lck}$ Complex in Human T–Cell Activation," *Immunological Reviews,* 111:225–266, 1989.

Schiff et al., "Lymphocyte Killing of Macrophages Induced by OKT3 Monoclonal Antibody," *FASEB,* 70th Annual Meeting, St. Louis, Missouri, pp. 1100, No. 5499, Apr. 13, 18, 1986.

Schwartz et al., "T–Cell Clonal Anergy," *Cold Spring Harbor Symposia on Quantitative Biology,* LIV:605–610, 1989.

Schwartz, "A Cell Culture Model for T Lymphocyte Clonal Anergy," *Science,* 248:1349–1356, Jun. 1990.

Sehon, "Carl Prausnitz Memorial Lecture, Suppression of Antibody Responses by Chemically Modified Antigens," *Int Arch Allergy Appl Immunol,* 94:11–20, 1991.

Shahinian et al., "Differential T Cell Costimulatory Requirements in CD28–Deficient Mice," *Med and Clin Microbiol,* 83(10):AB–590, Abstract No. 98234, 1987.

Shinagawa et al., "Purification of Staphylococcal Toxic Shock Syndrome Toxin–1 (Enterotoxin F) and Preparation of Anti–Toxic Shock Syndrome Toxin–1 Serum," *J Fac Agriciwate Univ,* 18(1):47–58, 1987.

Smith et al., "Inhibition of T Cell Activation by a Monoclonal Antibody Reactive Against the α3 Domain of human MHC Class I Molecules," *The Journal of Immunolgy,* 1054–1067, Jul. 1994.

Thistlethwaite, Jr. et al., "OKT3 Treatment of Steroid–Resistant Renal Allograft Rejection," *Transplantation,* 43(2):176–184, 1987.

Waid et al., "Treatment of Acute Cellular Rejection with T10B9.1A–31 or OKT3 in Renal Allograft Recipients," *Transplantation,* 53(1):80–86, Jan. 1992.

Woof et al., The Monocyte Binding Domains(s) on Human Immunoglobulin G, *Molecular Immunology,* 21(6):523–527, 1984.

Wu et al., "A Major Costimulatory Molecule on Antigen–Presenting Cells,CTLA4 Ligan A, is Distinct from B7," *J Exp Med,* 178:1789–1793, Nov. 1993.

Xu et al., "Costruction of a Mouse–Human Chimeric Light Chain from Murine Monoclonal Antibodies 33.28 Against Colorectal Carcinoma–Associated Antigens," *FASEB 7th Annual Meeting,* Abstract No. 2109, Atlanta, GA, Apr. 21–25, 1991.

Xu, "Humanization and Effector Function Modification of ORTHOCLONE OKT®3," poster abstract for Lymphocytes and Antibodies FASEB Summer Res Conference, dated Mar. 25, 1993.

Zivin, "Functional Analysis of Humanized OKT3 and OKT4A," Second Annual IBC International Conference on Antibody Engineering, San Diego, CA, Dec. 16–17, 1991.

Zivin, a talk presented by Linda Jolliffe, sponsored by Journal of Human Antibodies and Hybridomas, abstract for Second International Confereference on Human Antibodies and Hybridomas, Mar. 24,–26, 1992, Cambridge, England.

Zivin, "Monoclonal Antibodies in Transplantation," a talk presented by Linda Jolliffe at the Tokyo Symposium on Therapeutic Antibodies, Jan. 1993.

Zivin, "Fc Region Modified CDR–Grafted OKT3: Effector Functions by Design," poster presentation for FASEB Summer Conference: Antibodies and Lymphocytes, Jun. 1993.

Bluestone et al., "In Vivo Administration of Monoclonal Anti–T Cell Antibodies Can Activate Immune Responses and Prevent Malignant Progressive Tumor Growth," presented at the U.S. Japan Cooperative Program in Cancer Research, Honolulu, Hawaii, Jan. 1989.

Bruce et al., "Enhanced Humoral Response to HIV–Peptidic Antigen with Coadministration of Low–Dose Anti–CD3 Monoclonal Antibody in Mice," abstract for the Joint Meeting of the American Society for Biochemistry and Molecular Biology and the American Association of Immunologists, New Orleans, LA, Jun. 4–7, 1990, *FASEB,* 4(7):A2015, 1990.

Newell et al., "In Vivo TCR–Mediated and T Cell Activation Results in Immunopotentiation and Tumor Regression," abstract for the Joint Meeting of the American Society for Biochemistry and Molecular Biology and the American Association of Immunologists, New Orleans, LA, Jun. 4–7, 1990, *FASEB,* 4(7):A2022, 1990.

Urba et al., "Anti–CD3 Monoclonal Antibody Treatmet of Patients with CD3–Negative Tumors," *Cancer Research,* 52:2394–2401, May 1992.

Stohl, W. et al. Clin. Immunol. Immunopathol. 49 (2): 273–282, 1988.

Hirohata, S. et al. J. Immunol. 140: 3726–3744, Jun. 1988.

Weir et al. Immunochemistry, vol. 1, Blackwell Scientific Publications, Boston, MA, 1986.

Hirsch, R. et al. 72nd Anual FASEB Mtg., Las Vegas, NE, May 1–5, 1988, FASEB J. 2(5):Abstract 5506, May 1988.

mAb-A(ANTI-CD3)  PEPTIDE

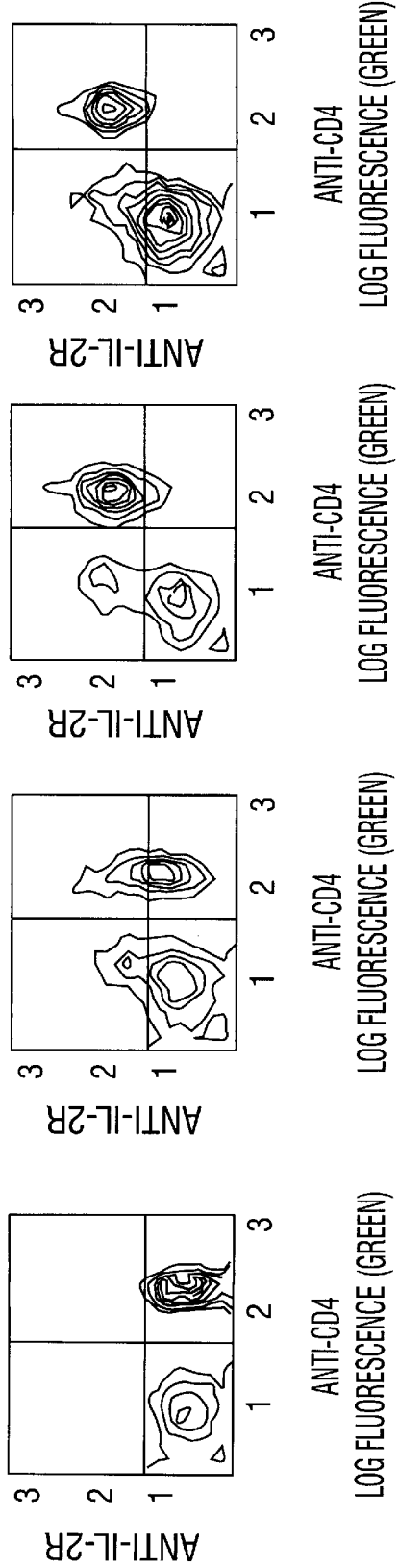
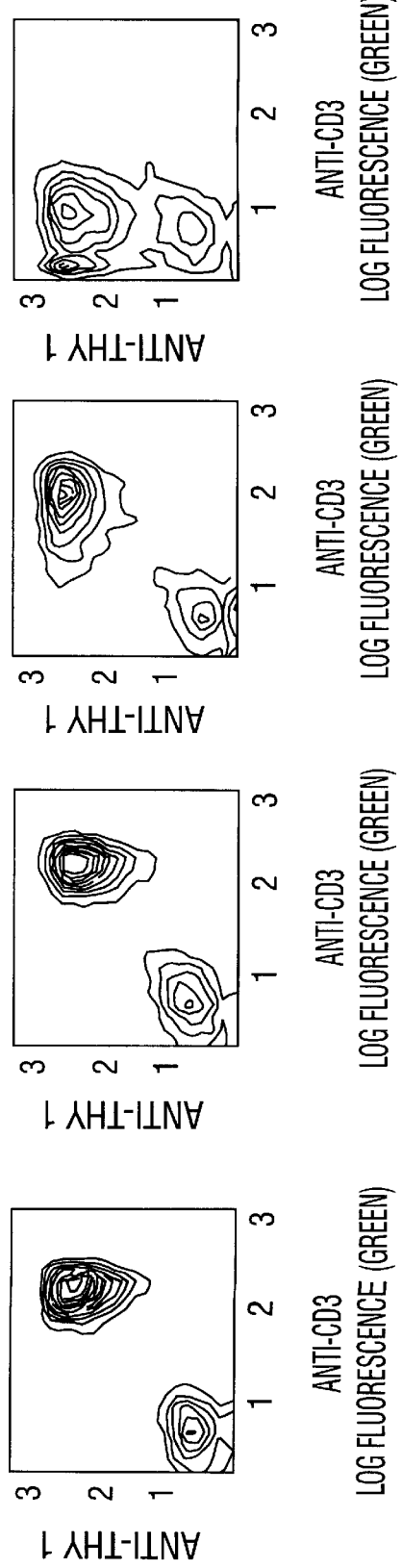

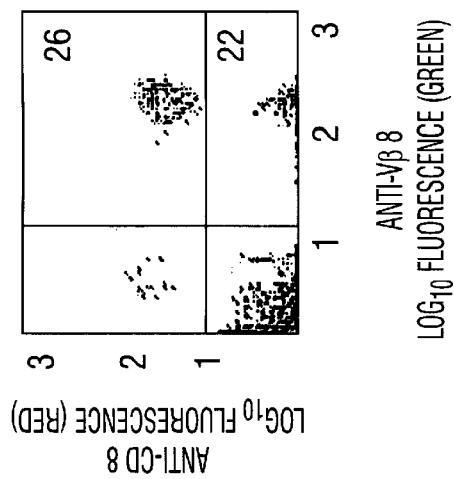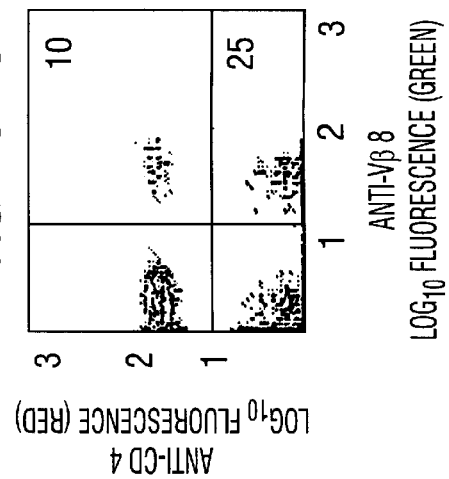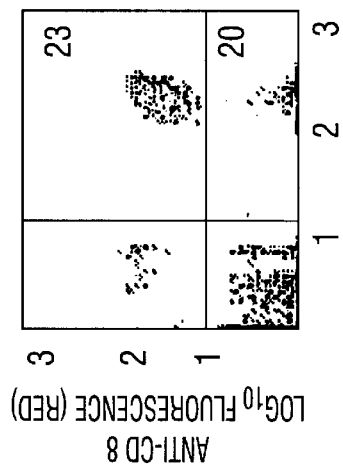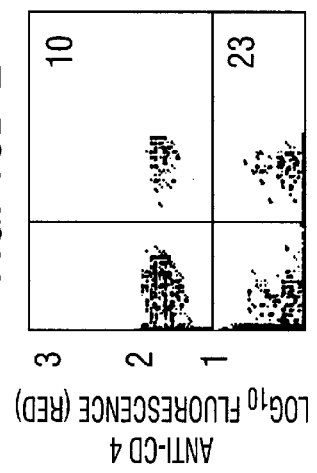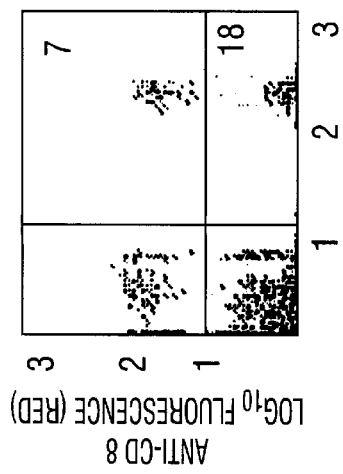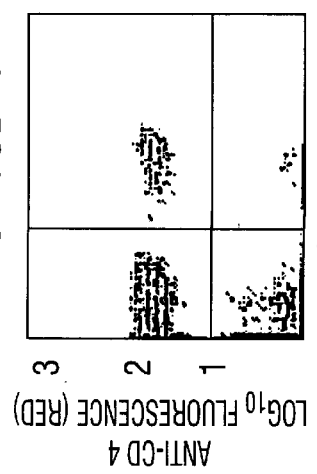

METHODS OF PROMOTING IMMUNOPOTENTIATION AND PREPARING ANTIBODIES WITH ANTI-CD3 ANTIBODIES

This is a divisional application of copending application Ser. No. 08/286,805, filed Aug. 5, 1994 and a continuing application of U.S. Ser. No. 07/990,553 filed Dec. 14, 1992, now abandoned, which is a continuing application of U.S. Ser. No. 07/524,304 filed May 16, 1990 now abandoned, which is a continuing application of Ser. No. 07/429,729, filed Oct. 27, 1989, now abandoned.

BACKGROUND OF THE INVENTION

1. Field of the Invention

This invention relates to immunology, and, more specifically, to the preparation and use of immunopotentiating agents which are capable of eliciting, enhancing and/or otherwise modifying immune responses. These agents, through their ability to elicit or enhance cellular or humoral responses, have potential utility in a variety of disease conditions wherein immunotherapy might be expected to provide a benefit.

2. Description of Related Art

The body's immune system serves as a defense against a variety of conditions, including, e.g., injury, infection and neoplasia, and is mediated by two separate but interrelated systems, the cellular and humoral immune systems. Generally speaking, the humoral system is mediated by soluble products, termed antibodies or immunoglobulins, which have the ability to combine with and neutralize products recognized by the system as being foreign to the body. In contrast, the cellular immune system involves the mobilization of certain cells, termed T-cells, that serve a variety of therapeutic roles.

(a) The Immune System

The immune system of both humans and animals include two principal classes of lymphocytes: the thymus derived cells (T cells), and the bone marrow derived cells (B cells). Mature T cells emerge from the thymus and circulate between the tissues, lymphatics, and the bloodstream. T cells exhibit immunological specificity and are directly involved in cell-mediated immune responses (such as graft rejection). T cells act against or in response to a variety of foreign structures (antigens). In many instances these foreign antigens are expressed on host cells as a result of infection. However, foreign antigens can also come from the host having been altered by neoplasia or infection. Although T cells do not themselves secrete antibodies, they are usually required for antibody secretion by the second class of lymphocytes, B cells.

There are various subsets of T cells, which are generally defined by antigenic determinants found on their cell surfaces, as well as functional activity and foreign antigen recognition. Some subsets of T cells, such as $CD8^+$ cells, are killer/suppressor cells that play a regulating function in the immune system, while others, such as $CD4^+$ cells, serve to promote inflammatory and humoral responses. (CD refers to cell differentiation cluster; the accompanying numbers are provided in accordance with terminology set forth by the International Workshops on Leukocyte Differentiation (5). A general reference for all aspects of the immune system may be found in (1)).

(b) T Cell Activation

Human peripheral T lymphocytes can be stimulated to undergo mitosis by a variety of agents including foreign antigens, monoclonal antibodies and lectins such as phytohemagglutinin and concanavalin A. Although activation presumably occurs by binding of the mitogens to specific sites on cell membranes, the nature of these receptors, and their mechanism of activation, is not completely elucidated. Induction of proliferation is only one indication of T cell activation. Other indications of activation, defined as alterations in the basal or resting state of the cell, include increased lymphokine production and cytotoxic cell activity.

T cell activation is an unexpectedly complex phenomenon that depends on the participation of a variety of cell surface molecules expressed on the responding T cell population (2,3). For example, the antigen-specific T cell receptor (TcR) is composed of a disulfide-linked heterodimer, containing two clonally distributed, integral membrane glycoprotein chains, $\alpha$ and $\beta$, or $\gamma$ and $\delta$, non-covalently associated with a complex of low molecular weight invariant proteins, commonly designated as CD3 (the older terminology is T3) (2,4).

The TcR $\alpha$ and $\beta$ chains determine antigen specificities (6). The CD3 structures are thought to represent accessory molecules that may be the transducing elements of activation signals initiated upon binding of the TcR $\alpha\beta$ to its ligand. There are both constant regions of the glycoprotein chains of TcR, and variable regions (polymorphisms). Polymorphic TcR variable regions define subsets of T cells, with distinct specificities. Unlike antibodies which recognize soluble whole foreign proteins as antigen, the TcR complex interacts with small peptidic antigen presented in the context of major histocompatibility complex (MHC) proteins. The MHC proteins represent another highly polymorphic set of molecules randomly dispersed throughout the species. Thus, activation usually requires the tripartite interaction of the TcR and foreign peptidic antigen bound to the major MHC proteins.

With regard to foreign antigen recognition by T cells the number of peptides that are present in sufficient quantities to bind both the polymorphic MHC and be recognized by a given T cell receptor, thus inducing immune response as a practical mechanism, is small. One of the major problems in clinical immunology is that the polymorphic antigens of the MHC impose severe restrictions on triggering an immune response. Another problem is that doses of an invading antigen may be too low to trigger an immune response. By the time the antigenic level rises, it may be too late for the immune system to save the organism.

The tremendous heterogeneity of the MHC proteins among individuals remains the most serious limiting factor in the clinical application of allograft transplantation. The ability to find two individuals whose MHC is identical is extremely rare. Thus, T cells from transplant recipients invariably recognize the donor organ as foreign. Attempts to suppress the alloreactivity by drugs or irradiation has resulted in severe side effects that limit their usefulness. Therefore, more recent experimental and clinical studies have involved the use of antibody therapy to alter immune function in vivo. The first successful attempt to develop a more selective immunosuppressive therapy in man was the use of polyclonal heterologous anti-lymphocyte antisera (ATG) (7, 8, 9).

Clinical trials of the ATG treatment suggested a significant reduction of early rejection episodes, improved long term survival and, most importantly, reversal of ongoing rejection episodes. However, the results were often inconsistent due to the inability to standardize individual preparations of antisera. In addition, the precise nature of the target antigens recognized by the polyclonal reagents could not be defined, thus making scientific analysis difficult. The advent of monoclonal antibody (mAb) technology provided the basis for developing potentially therapeutic reagents that react with specific cell surface antigens which are involved in T cell activation.

(c) Effect of Monoclonal Antibodies on the Immune System

Monoclonal antibodies (mAb) were developed by Kohler and Milstein in 1975. The methods generally used to produce mAb consist of fusing (hybridizing) two types of somatic cells: (1) a neoplastic myeloma cell line; and (2) a normal B lymphocyte obtained from an immunized animal. The result is called a hybridoma which is characterized by immortal growth and the ability to secrete antibodies specific for the immunization antigen.

One of the clinically successful uses of monoclonal antibodies is to suppress the immune system, thus enhancing the efficacy of organ or tissue transplantation. U.S. Pat. No. 4,658,019, describes a novel hybridoma (designated OKT3) which is capable of producing a monoclonal antibody against an antigen found on essentially all normal human peripheral T cells. This antibody is said to be monospecific for a single determinant on these T cells, and does not react with other normal peripheral blood lymphoid cells. The OKT3 mAb described in this patent is currently employed to prevent renal transplant rejection (10).

One unexpected side effect of the OKT3 therapy was the profound mitogenic effect of the mAb in vivo (28). Although anti-CD3 mAb has been shown to activate T cells in vitro to produce various lymphokines, etc. (11), OKT3 has not been previously used to stimulate the immune system in vivo.

In addition, other cell surface molecules have been identified that can activate T cell function, but are not necessarily part of the T cell surface receptor complex. Monoclonal antibodies against Thy-1, TAP, Ly-6, CD2, or CD28 molecules can activate T cells in the absence of foreign antigen in vitro (12, 13,14,15,16). Moreover, certain bacterial proteins although differing in structure from mAbs, also have been shown to bind to subsets of T cells and activate them in vitro (17). Although some of these agents, in vitro effects have previously been demonstrated, in vitro activity is often not a reliable predictor of in vivo effects.

(d) Immune System and Tumor Growth

One cause of malignant tumor growth is believed to be the inability of the immune system to respond appropriately to tumor antigen. For example, malignant progressor tumors are only weakly immunogenic and can evade host recognition and rejection. Both specific and non-specific effector pathways have been implicated in tumor immunity. Treatment by immunotherapy is aimed at remedying defects in the immune weaponry. The aim of immunotherapy has been the enhancement of one or both of these pathways. One potential approach to therapy is to activate host antitumor cellular effector mechanisms.

Historically, non-specific adjuvants such as BCG or pertussis have been used to augment immune responses. In normal individuals these adjuvants amplify immune responses by providing non-specific stimuli that enhance overall immunity. However, these adjuvants do not selectively act on T cells, or subsets of T cells, and have not been shown capable of overcoming immunodeficiency states. Unfortunately, current modes of immunotherapy which induce non-specific effector cells are not effective enough in potentiating anti-tumor responses (18). Recently, immunotherapy regimens which utilize the ability of the immune system to recognize tumor antigens in a specific manner, for instance utilizing specific tumor-infiltrating lymphocytes, for immunotherapy, have been suggested to result in superior anti-tumor immunity (19). Thus, current efforts toward developing more efficacious forms of immunotherapy have focussed on specific anti-tumor response and memory-following antigen recognition. One approach that has not previously been accomplished has been the in vivo administration of T cell activating mAbs to promote anti-tumor activity.

(e) Defenses Against Viral Infections

Human immunodeficiency virus (HIV), the biologic agent of AIDS, causes a persistent infection associated with profound immunosuppression resulting in susceptibility to opportunistic infections. Immunological responses to HIV infection require the development of both humoral and cell mediated effector mechanisms; however current efforts in treatment and vaccine design have fallen short of success either due to the immunodeficiency associated with the viral infection, or to the low immunogenicity of the vaccine (20). The development of a safe and effective vaccine against infection with human immunodeficiency virus (HIV) is complicated by a lack of understanding of protective immunity to HIV and disease development, and the absence of an adequate and convenient animal model for studying HIV infection.

Because HIV can be transmitted as either a cell-free or cell-associated virus, a protective immune response against HIV infection will likely require both humoral and cell-mediated immunity, including neutralizing antibody against HIV, antibodies involved in antibody-dependent cellular cytotoxicity and cytotoxic lymphocytes. All of these activities involve virus-specific T cells. T cell activation requires potent in vivo immune responses to foreign antigens such as viruses.

In individuals infected with HIV, two components of the immune system are suboptimal and, therefore, the ability to generate an immune response in these individuals has been compromised. First, the reduced frequency of antigen-reactive $CD4^+$ T cells is apparently not sufficient to mount an appropriate immune response to HIV, especially if the quantity of HIV antigen is low. CD4 is a membrane protein that acts as a binding site and entry port into $CD4^+$ lymphocytes for the human immunodeficiency virus-type 1 (HIV-1) (21). Second, all immune responses are dependent on the ability of T cells to recognize processed antigen associated with major histocompatibility antigens (MHC). Any vaccine approach which utilizes HIV peptides or inactivated virus antigen must depend on the ability of antigenic peptides to bind the appropriate MHC antigens necessary to initiate an immune response. Given the tremendous polymorphism of the MHC antigens expressed in the population, and the variation of the HIV virus, developing a successful HIV vaccine for general use is difficult and has not yet been successful.

(f) Problems in Developing Vaccines to Weakly Immunogenic Antigens

The usefulness of certain peptides, proteins or other potential or desired immunogens in vaccines can be limited by several critical factors. For example, low immunogenicity of the peptide or other structure which one desires to employ can be a difficult problem to overcome, particularly with smaller peptides and those peptides which do not contain appropriately strong B- and/or T-cell potentiating sequences. Such peptides are typically only weakly immunogenic at best. Moreover, to be of widespread applicability, the peptides chosen must be capable of inducing an immune response in a majority of the population.

It has been difficult to protect against attack by organisms such as the HIV virus or to provide tumor immunity for several reasons. For example, genetic differences exist among individuals at the major histocompatibility locus, which limits the system's ability to respond to individual small peptides. Thus, the various components of the immune response, including the T cells and B cells, may not interact appropriately in generating a response to non- or weakly-immunogenic small peptides. Attempts to improve peptidyl immunogenicity have centered principally on the use of adjuvants such as alum or complete Freund's adjuvant. However, prior adjuvants such as these have proven to be inadequate for various reasons, including an inability of the adjuvant to specifically enhance T or B cell activity and the inability of the adjuvant to overcome the severe limitations of MHC restriction.

Although glimpses into the defense mechanisms of the body's own immune system have been provided by in vitro studies and by observation of some in vivo reactions, there is a serious lack of successful therapeutic methods to augment immunity in vivo. Improved compositions and/or methodology for eliciting or enhancing cellular or humoral responses in mammals are needed both to provide animal models for investigation of therapeutic regimes, to provide novel means of preparing improved immune system-directed products such as improved immunotherapeutic antibodies, and to advance treatment and possible immunization, e.g., for conditions such as HIV, cancer and infections.

SUMMARY OF THE INVENTION

The present invention is concerned with a broad array of embodiments, generally involving methods and compositions for potentiating one or more aspects of the immune response of a human or other animal having an immune system, as well as to products which may be derived out of the use of these methods and compositions. Generally speaking, the invention concerns essentially four categories of what may be referred to broadly as immunopotentiating or immunoactivating compositions: 1) individual immunopotentiating agents which are used to potentiate one or more aspects of the immune system; 2) immunopotentiating "adjuvant" compositions wherein immunopotentiating agents are employed essentially as "adjuvants" to improve the body's immune responsiveness to other compounds which are co-administered with, or included in with, compositions containing the immunopotentiating agent; 3) immunopotentiating conjugates wherein the immunopotentiating agent is actually chemically coupled to the compound against which an immune response is desired; and 4) products derived from the administration of one or more of the foregoing, including, e.g., antibodies, antibody-producing cells, T-cells, potentiated bone marrow progenitor cells, and the like.

The term "activation" is generally defined to refer to any change induced in the basal or resting state of T or B cells. This includes, but is not limited to, increased cell proliferation and DNA synthesis, lymphokine and cytotoxic cell production, a rapid rise in intracellular calcium, release of water soluble inositol phosphates, increased IL-2 receptor expression, enhanced proliferative response to IL-2, and enhanced responses to foreign antigens or MHC (23). In contrast, the term "immunopotentiating" is classically defined as the ability to produce an effect on the immune system which enhances the system's ability to respond to foreign antigens. Thus, immunopotentiation may affect the cellular response, humoral response, or both. Exemplary indices of immunopotentiation include, but are not limited to, cell proliferation, increased DNA synthesis, increased production of lymphokines, increased production of cytotoxic cells, calcium efflux, or any other change that raises the cell above the basal or resting state.

While one can consider there to be a distinction between the terms "potentiation" and "activation", in the context of the present invention the use of the term "potentiation" is intended to include both potentiation and activation. Thus, the immunopotentiation achieved by the methods and agents of this invention may affect all T cells, certain subsets of T cells, or B cells, depending on the nature of the agent(s) and their dose levels. One of the objects of this invention is to provide means for fine tuning immunopotentiation, allowing one to target T and/or B cell response depending on the nature of the clinical condition to be treated.

Accordingly, in certain general embodiments, the present invention concerns the preparation and use of immunopotentiation agents, whether used alone as a direct immunopotentiation agent, or combined with other compounds, either covalently or simply admixed in the same composition. In the context of the present invention, the term immunpotentiation agent is intended to include immunopotentiating antibodies, as well as certain bacterial proteins which have been determined to have profound immunopotentiation actions.

In terms of antibodies, useful immunopotentiation agents will generally involve antibodies against a cell surface epitope of T-cells wherein binding of the antibody to the surface epitope of the T-cell will result in immunopotentiation. An exemplary antibody is anti-CD3 (e.g., OKT3), previously known only to be immunosuppressive and not previously known to be immunopotentiating. The present inventor has surprisingly discovered that, in fact, when anti-CD3 is administered at relatively low doses (e.g., on the order of 100 to 200 $\mu$g/kgm body weight), rather than being immunosuppressive it exhibits a very profound immunopotentiation effect. The reason for this appears to include but may not be limited to the induction of lymphokines, the proliferation of T cells, or even the progression of T cells from a naive to memory state.

While anti-CD3 is a useful immunopotentiation agent, numerous other immunopotentiation antibodies are contemplated to be within the scope of the present invention. Such antibodies are defined generally as antibodies which recognize and activate a T cell activation molecule or epitope on the cell surface of T cells. For example, monoclonal antibodies which are particularly useful in the practice of the present invention will comprise those directed against the T cell variable or constant epitopes on the cell surface of T cells. The T cell activation molecules which are expressed on the cell surface may be either those associated with the T cell receptor complex or those with the antigens distinct from, that is not physically associated with, TcR on the cell surface. Specific embodiments of T cell activation molecules comprise either the variable or the constant region epitopes as expressed on the antigen specific T cell receptor polymorphic chains, e.g., $\alpha$, $\beta$, $\gamma$, and $\delta$ chains.

Embodiments of the non-polymorphic TcR associated CD3 chains against which monoclonal antibodies may be directed for use as immunopotentiating agents are the $\gamma$, $\delta$, $\epsilon$ or $\zeta$ chains. Monoclonal antibodies have been developed against some of these chains, as exemplified by OKT3, SP34, UCHTI or 64.1 (68–70). Among the T cell surface antigens which are distinct from, and not physically associated with, TcR, are CD2, CD28, Thy-1, and the activation epitopes expressed on members of the Ly-6 protein family.

As noted, the immunopotentiation agents of the present invention will also include certain potentiating bacterial proteins such as bacterial enterotoxins, exemplified by staphylococcal enterotoxin B (SEB). SEB is now known to activate T-cells and provide surprisingly profound and subset-specific potentiation. As with some of the potentiating antibodies, the mechanism of how enterotoxins function to stimulate the immune system is not entirely clear, but could involve lymphokine production or T cell proliferation. While SEB comprises a preferred enterotoxin for immunopotentiation purposes, the invention contemplates that other similar enterotoxins, such as staphylococcal enterotoxins A, $C_1$, $C_2$, D, E, toxic shock syndrome toxin (TSST), exfoliating toxin (ExFT) and likely even mycoplasma arthriditis substance, will find similar utility.

For use directly as immunopotentiation agents, one will generally desire to first combine the agent in a pharmacologically suitable vehicle, such as combining with an appropriate diluent or buffer, in an amount and concentration that is appropriate to effectuate potentiation of the immune system when administered. Typically, in the case of, e.g., anti-CD3, one will desire to provide parenteral compositions having from about 0.1 mg/ml to about 1 mg/ml, in order to allow the parenteral administration of appropriate amounts of the antibody.

As mentioned, the present invention contemplates the use of these immunopotentiating agents in immunogen containing compositions such as vaccines, where the agents serve as "adjuvants" to improve the immunogenicity of other components of the composition. Thus, it is contemplated that through the use such agents as "adjuvants", the preparation of useful vaccines using only weakly or non-immunogenic molecules not previously known to function as immunogens is enabled. In such embodiments, the immunopotentiating protein is admixed or otherwise coadministered with the molecule against which an immune response is desired, with the immunopotentiating agent being present in amounts effective to promote potentiation upon administration to the particular subject.

It is proposed that still further advantages will be realized where the immunopotentiation agent is actually conjugated to the molecule against which an immune response is desired. These conjugates are referred to in the context of the present invention as "heteroconjugates". As used herein, an immunopotentiating heteroconjugate is defined as an immunopotentiating agent conjugated to a second protein or other molecule against which an immune response is desired, the conjugation being in the nature of a chemical or molecular crosslink.

Exemplary embodiments of the second molecule include proteins which comprise amino acid sequences or other potential determinants (e.g., a non-amino acid determinant such as a sialo group) against which a cellular or humoral immune response is desired. However, as with the adjuvant embodiments, the present invention also contemplates the use of non-protein molecules, such as glycolipids, carbohydrates or even lectins, as the second molecule against which an immune reaction is sought. All that is required for use in the context of heteroconjugates is that one be capable of conjugating the molecule to the immunopotentiation agent.

The immunopotentiating protein of the heteroconjugate may also be formed by linking two monoclonal antibodies directed against two distinct but specific T cell epitopes. A specific embodiment of this type of immunopotentiating protein is anti-CD3 coupled with anti-CD4 to form a CD4 subset-specific immunopotentiating protein. It has been demonstrated that administering of such a bispecific antibody construct in vivo activates T cells to a surprising degree (see, e.g., U.S. Pat. No. 4,676,980 to Segal, and FIG. 14 herein). It is proposed by the present inventor that one may employ such a bispecific antibody construct as the immunopotentiating ligand of heteroconjugates formed with a second protein against which an immune response is desired.

Use of the heteroconjugate disclosed in this invention is believed to aid in directing the immune attack to specific epitopes, via the attached compound or protein. Thus, it is proposed that a particular utility of these embodiments will be found in the treatment of diseases such as cancer, where only weakly immunogenic tumor-specific or tumor-associated proteins are found to appear on the cell surface of many tumors, or are found to characterize the tumor.

It is proposed that other particularly important applications are in the context of viral-specific or viral-associated epitopes, particularly those where the immune system may be compromised, such as in the case of HIV infections. Moreover, amino acid sequences homologous to those derived from genes in a bacteria, fungus, protozoal or metazoal parasite, may also be used as conjugating agents.

Of course, where desired, the epitopes used as second proteins may either be derived from the cell surface or extracted from cells which are infected or diseased. Alternatively, amino acid sequences can be made synthetically by standard chemical synthetic or molecular biology methods. Thus, for example, in the case of HIV immunotherapy, amino acid sequences are known for various peptides isolated from the HIV virus gp120 cell membrane which can be employed as embodiments of the second compound, whether it be conjugated to the immunopotentiating protein or simply admixed in an appropriate pharmaceutical vehicle. Preferred embodiments of peptides which may be used as second proteins in a heteroconjugate used to augment immunity against HIV, comprise peptides 18, T1, T2, or peptides derived from the CD4 binding site.

In similar fashion, epitopes specific for amino acid sequences homologous with those expressed on the surface of human hepatitis virus, or extracted from cells infected with the virus may be used as the second protein. Viral specific epitopes may also comprise amino sequences homologous with those expressed on the surface of infected cells.

Immunogenic compositions may be prepared for administration to subjects by including any of the foregoing immunopotentiating compositions, and formulated to include an effective amount of 1) an immunopotentiating protein (i.e., where one desires simply generalized immunopotentiation rather than potentiation that is directed against a second compound), 2) an immunopotentiation protein in combination with a second compound, or 3) an immunopotentiation protein conjugated to such a second compound. The materials that are formulated are preferably rendered pharmacologically acceptable by manufacturing in accordance with good manufacturing practices, extensively dialyzed to remove undesirable small molecular weight molecules and/or lyophilized for more ready formulation into a desired vehicle.

Where such compositions are intended for human administration, one will typically desire to include an amount of immunopotentiation agent that will result in T cell activation in the absence of concomitant immunosuppression. The determination of exact amounts will depend on the particular circumstances, such as the particular condition to be treated, the physical condition of the patient, the type of immunogenic composition that is to be administered, and the like. Thus, e.g., based on murine studies performed by the inventor one can extrapolate in the case of embodiments incorporating immunopotentiating antibodies such as anti-CD3, anti-CD28 or anti-CD2, that suitable formulations should typically include from about 10 ug to about 1000 ug bolus/patient every 14 days or so, and more preferably 100 ug to about 400 ug of the antibody per patient. Similarly, one can extrapolate in the case of enterotoxins that one should typically desire to employ from about 100 ug to about 10 mg of the enterotoxin per dosage, and more preferably about 1 to about 5 mg/dose.

For the preparation of compositions suitable for parenteral administration, the immunogens of the invention may be formulated in oils such as sesame or peanut oil, aqueous propylene glycol, in liposomes or in sterile aqueous solutions. Such solutions are typically suitably buffered if necessary and the liquid diluent first rendered isotonic with sufficient saline or glucose. Additionally, stabilizers in the form of, for example, sorbitol or stabilized gelatin may be included. These particular aqueous solutions may be particularly well suited for intramuscular and subcutaneous injections, as may be preferred for vaccination using antigenic preparations.

The proteins may be formulated into the composition as neutral or salt forms. Pharmaceutically acceptable salts, include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isoprophylamine, trimethylamine, 2-ethylamino ethanol, histidine, procaine, and the like.

The compositions are administered in a manner compatible with the dosage formulation, and in such amount as will be therapeutically effective and immunogenic. The quantity to be administered depends on the subject to be treated, including, e.g., the capacity of the individual's immune system to synthesize antibodies, and the degree of protection desired. Precise amounts of active ingredient required to be administered depend on the judgment of the practitioner. Suitable regimens for initial administration and booster shots are also variable, but are typified by an initial administration followed by subsequent inoculations or other administrations.

Various methods of achieving additional adjuvant effect for the vaccine includes use of agents such as aluminum hydroxide or phosphate (alum), commonly used as 0.05 to 0.1 percent solution in phosphate buffered saline, admixture with synthetic polymers of sugars (Carbopol) used as 0.25 percent solution, aggregation of the protein in the vaccine by heat treatment with temperatures ranging between 70° to 101° C. for 30 second to 2 minute periods respectively. Aggregation by reactivating with pepsin treated (Fab) antibodies to albumin, mixture with bacterial cells such as C. parvum or endotoxins or lipopolysaccharide components of gram-negative bacterial, emulsion in physiologically acceptable oil vehicles such as mannide mono-oleate (Aracel A) or emulsion with 20 percent solution of a perfluorocarbon (Fluosol-DA) used as a block substitute may also be employed.

While administration of the foregoing immunopotentiating compositions will likely find their greatest utility and application in the treatment of human disease, the invention is by no means limited to human application, and is intended to apply to any mammal having an immune system, including, e.g., rodents such as mice, hamsters and rats, primates, rabbits, even farm animals such as cows, pigs, etc. Thus, the invention contemplates, e.g., that certain of the foregoing embodiments will have general applicability wherever one desires to obtain an enhanced immune response against a desired molecule, such as in the initial immunization of animals for hybridoma or even polyclonal antibody development.

While it is contemplated that the nature of the second molecule is not crucial to the successful practice of the invention, it is recognized that the invention will find its greatest utility where the second molecule is a peptide, in that peptides are often notoriously difficult to obtain an immune response against. Thus, it is believed that particular benefits will be realized through the use of peptides having from about 8 to about 100 amino acids in length, and even more preferably, about 8 to about 50 amino acids in length.

In the context of heteroconjugates, it is contemplated that numerous methods for conjugation may be applied, including but not limited to: 1) the formation of biotin-avidin bridges; 2) the use of cross linkers such as SPDP to link the functional units; 3) cross-linking of maleimide and SH groups; as well as numerous other possibilities. In general, all that is required is that the cross-linking maintain the integrity of the peptidic antigen and leave unaltered the activating property of the immunopotentiating reagent.

As mentioned above, the present invention contemplates that various useful biological products may be derived through the application of the foregoing immunopotentiating compositions. For example, the adjuvant and heteroconjugate embodiments will provide extremely useful means for preparing antibodies, including monoclonal antibodies. Moreover, it has been found that immunopotentiating antibodies such as anti-CD3 can serve to promote the recruitment of hematopoietic progenitor cells, presumably by stimulating the release of cytokines and lymphokines from activated T-cells. This lends the possibility that such embodiments may be employed to prepare highly active bone marrow for transplantation, or even for administration to bone marrow transplant recipients or those with depleted bone marrow cells to provide a metabolic boost to the marrow. Moreover, it is contemplated that activated T cells themselves will find some utility, such as in anti-tumor therapy that employs tumor-infiltrating lymphocytes.

BRIEF DESCRIPTION OF THE DRAWINGS

Other objects and advantages of the invention will become apparent upon reading the following detailed description and upon reference to the drawings in which:

FIG. 2. Activation of peripheral lymph node T cells from anti-CD3-treated C3H mice as assessed by flow cytometry (FCM). Two color FCM from control animals and those treated with, 4, 40, or 400 μg of anti-CD3 are displayed as contour plots on a logarithmic scale. Intensity of green FITC fluorescence is plotted along the x-axis and red (B-phycoerythrin) fluorescence is plotted along the y-axis. (A) Anti-CD4 staining on the x-axis and anti-IL-2 receptor (Il-2R) staining on the y-axis. (B) Anti-CD3 staining on the x-axis and anti-Thy-1 staining on the y-axis. C3H/HeN MTV$^-$ mice were killed 18 hours after intravenous injection of purified anti-CD3 (mAb 145-2C11) that was grown and purified as described (24). Femoral, axillary, and mesenteric lymph nodes were removed and dissociated into a single-cell suspension and FCM analysis was performed (25). Cells were stained with FITC-anti-CD3 or FITC-anti-CD4 (mAb GK1.5) (Becton Dickinson), and biotin-conjugated anti-IL-2R (mAb 3C7) or biotin-conjugated mAb to Thy-1.2 (Becton Dickinson), then counterstained with B-phycoerythrin-conjugated egg white avidin (Jackson Immuno Research Laboratories). These results show that low dose (4 ug) anti-CD3 treatment activates T cells as evidenced by IL-2R expression but does not modulate T cell receptors.

FIG. 10. Expansion of $V_\beta 8^+$ cells in SEB-treated mice. Three days after treatment of mice with SEB, spleen cells were incubated with anti-$V_\beta 8$ and $V_\beta 8^+$ cells were assayed by flow cytometry. Expansion of $V_\beta 8^+$ cells was observed due to SEB treatment.

The results demonstrate that when the peptide was administered alone by either route, very little specific antibody titer developed. However, when anti-CD3 was co-administered, a surprising increase in specific antibody titer resulted.

Figure 15:
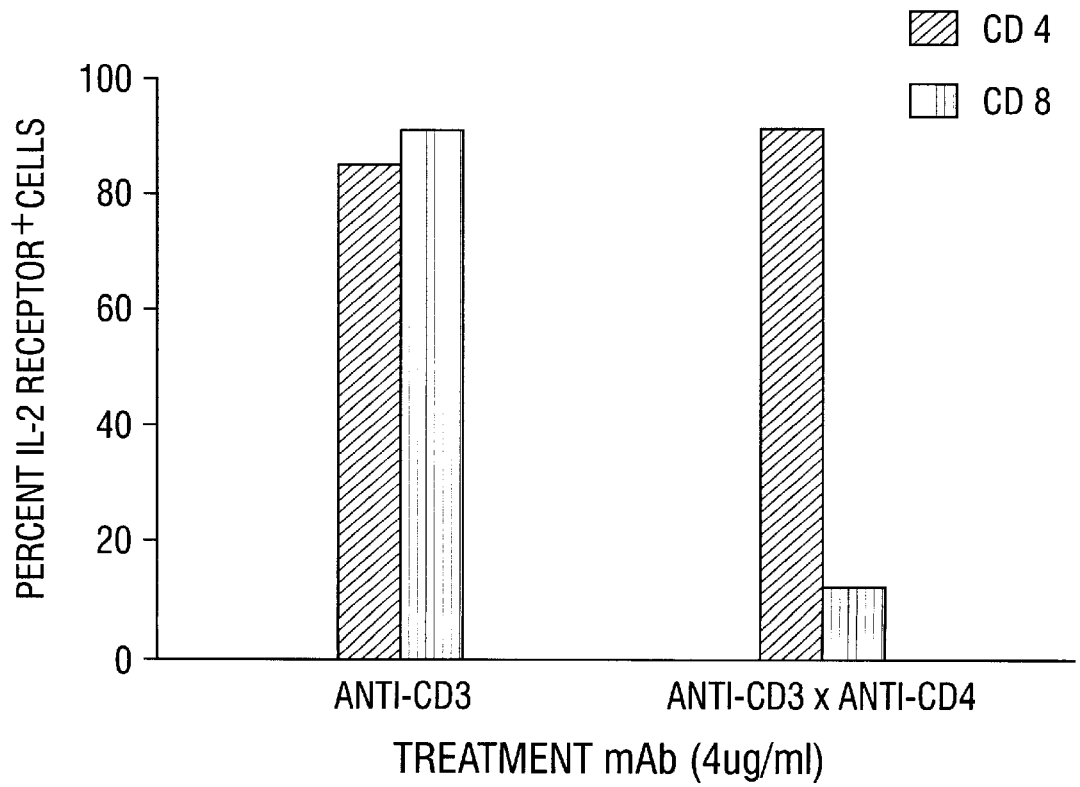

FIG. 15. In vivo treatment with mAbs. The response of IL-2 receptor positive cells was compared after treatment with anti-CD3 alone versus after treatment with a heteroconjugate comprising anti-CD3 and anti-CD4. Anti-CD3 alone resulted in significant increases in both CD4+ and CD8+ IL-2 receptor+ cells. The heteroconjugate (linked by the SPDP method) produced an enhanced IL-2R expression on CD4+ cells, indicative of a subset-specific response.

Figure 16A:
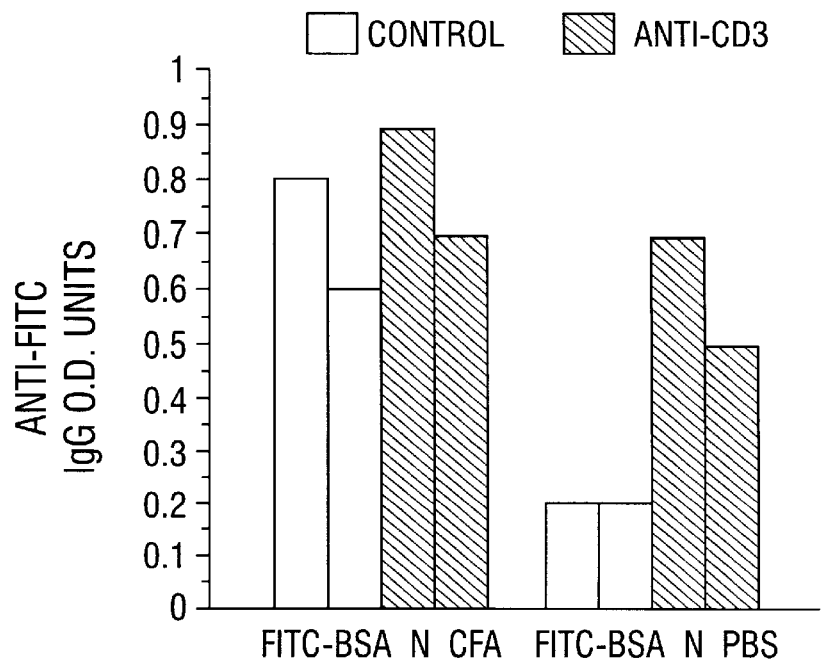
Figure 16B:
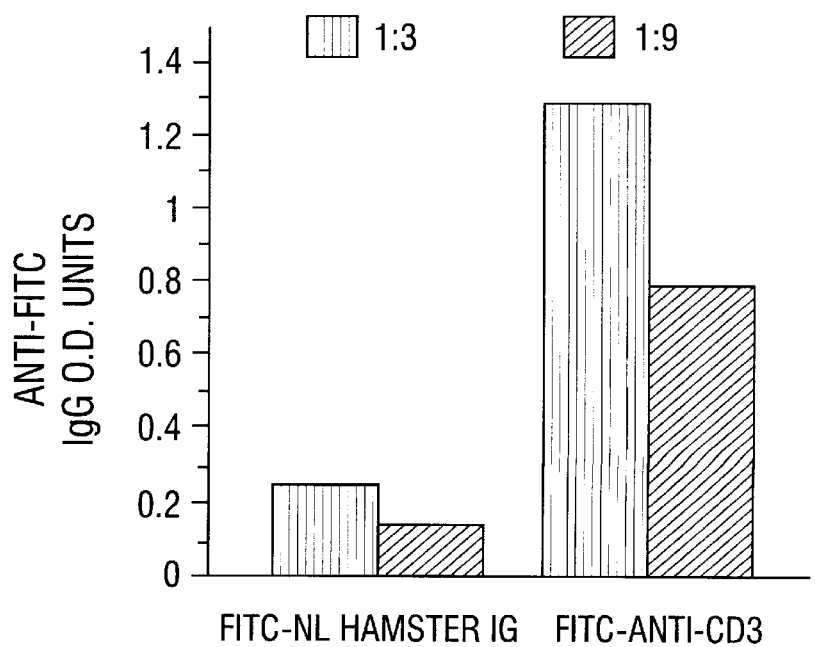

FIG. 16. In vivo immune stimulation of mice administered a heteroconjugate. Panel A: IgG anti-FITC antibody production in anti-CD3 treated mice immunized with FITC-BSA in complete Freunds adjuvant (CFA) or PBS, compared to ELISA measurements of sera from control mice (open bars). Panel B: IgG anti-FITC antibody production measured from sera of FITC-anti-CD3 treated mice (left-hatched bars) compared to FITC-normal Hamster Ig (cross-hatched bars) measured by ELISA performed on day 10 bleeds.

Figure 17:
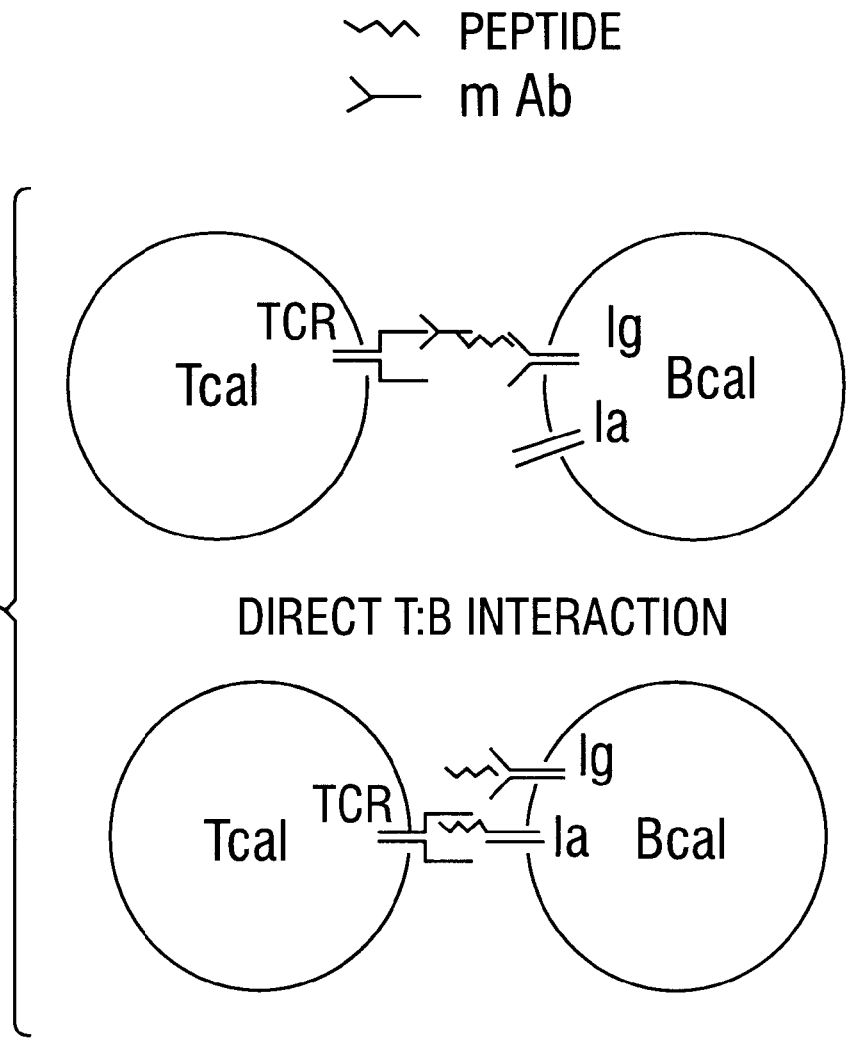

FIG. 17. Two models of T:B collaboration. A) Direct T:B interaction. B) Classical MHC restricted antigen interaction. Panel A illustrates the conventional model of T-B collaboration namely that the ability of T cells to recognize foreign antigen and promote immunoglobulin production depends on the recognition by TcR of peptidic antigen presented in the context of the polymorphic MHC molecules. In panel B, it is proposed that one can bypass the strict requirement of MHC-restricted antigen recognition by the use of immunopotentiating heterococonjugates. For example, F(AB')$_2$ fragment of anti-CD3 are coupled to peptidic antigen to bridge the T cell with peptide specific B cells. The resulting cross-linking of the TcR by this T-B interaction would result in the localized secretion of helper factors necessary to augment B cell triggering and Ab production in the absence of an MHC-restricted interaction.

DESCRIPTION OF THE PREFERRED EMBODIMENT

The body's immune system is not invincible. It succumbs to attack when it is unable to recognize the need to repel invaders, for example, when the foreign or abnormal stimulus is too weakly immunogenic to produce a response. Genetic immunodeficiency states as well as acquired immunodeficiency (e.g., drug or viral induced) also undermine the immune system's ability to respond to infection or abnormal growth such as neoplasms. Moreover, artificial suppression of the immune system, often employed in an attempt to minimize the risk of transplantation failure due to host versus graft disease, is accompanied by the risk of generating serious side effects, e.g., infection and even tumor development. A different type of problem arises when non-selective stimulation attacks normal as well as abnormal cells, leading to self-destruction.

That the immune system has a role in prevention or suppression of malignant growth is undisputed, but the nature and extent of that role is unclear. Attempts have been made to strengthen the immune response and/or to alter tumor responses to attack. However, such attempts to develop suitable immunotherapeutic protocols have not generally been successful. For example, both the transfer of immune lymphocytes as well as immune stimulation has been employed in attempts to treat tumors in cancer patients with little success. Moreover, the search for the "magic bullets," such as through the injection of antibodies or of antibodies with non-specific tumoricidal agents, e.g., toxins, have not resulted in the hoped-for regression of tumors. Similarly, non-specific stimulation of the immune system of tumor-bearing individuals by injecting adjuvants, e.g., BCG, has met with only limited success (e.g., in the case of melanoma). Moreover, immunization with unmodified allogenic tumor cells is ineffective, and may even result in a more rapid tumor growth.

The present invention discloses a collection of related strategies for overcoming one or more failures of the prior art in immunotherapy. The success and potential success of this strategy is demonstrated in the following examples. The strategy comprises producing new immunopotentiating agents and compositions which employ, for example, the use of 1) selected immunopotentiating agents alone, 2) as "adjuvants" with second agents against which a selected response is desired, or 3) as heteroconjugates wherein the immunopotentiating agent is conjugated to the second compound.

Figure 1A:
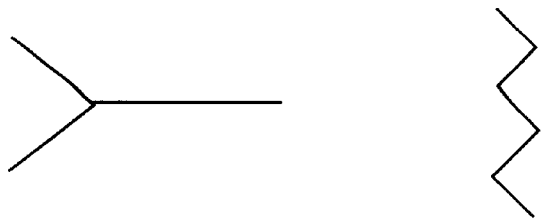
FIG. 1. Forms of Immune Augmentation. This figure demonstrates an overview of various embodiments of the invention, including "immunoadjuvant" embodiments wherein the immunopotentiating protein is simply admixed with a compound against which an immune response is desired (top panel), or where and actual heteroconjugate is formed between the immunopotentiating protein and the compound (middle panel). In the bottom panel is shown an embodiment wherein the immunopotentiating ligand is actually a bifunctional conjugate formed between two antibodies.
Figure 1B:
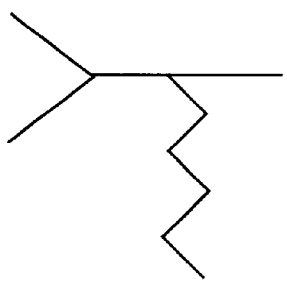
Figure 1C:
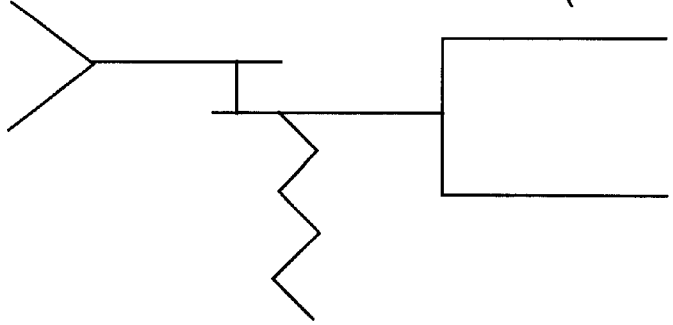

Shown in FIG. 1 is an overview of various embodiments of the invention. In the upper panel is shown a basic embodiment wherein an immunopotentiating protein (in the example shown, the immunopotentiating protein is an immunopotentiating antibody, anti-CD3) in an admixture with a peptide against which an immune response is desired. In the middle panel is shown a heteroconjugate embodiment, comprising a conjugate between an immunopotentiating protein (in this case an antibody) and a peptide against which an immune response is desired. In the bottom panel is shown a bifunctional ligand-conjugate formed between two antibodies (e.g., anti-CD4 and anti-CD3), wherein one of the antibodies is coupled to a peptide against which an immune response is desired.

As the following examples will illustrate, the success of the various strategies of the invention was demonstrated by in vivo responses of animals and humans to these immunopotentiating agents, indicating that immunopotentiation, tumor growth limitation, induced tumor immunity, resistance to infection, and enhanced bone marrow stem cell recruitment, has indeed been achieved as predicted by the inventor's novel theories.

1. Immunopotentiation Agents Achieving Potentiation Directly

A. Protection Against Infection or Abnormal Growth (Neoplasm)

It has been shown in vitro that monoclonal antibodies (mAb) recognizing specific T cell surface molecules can activate T cells in the absence of nominal antigen (26,27). The mAb apparently mimics the physiologic antigen and bypasses the T cell receptor (TcR) antigen-specific recognition mechanism. While T cell activation is critical to generating potent in vivo immune responses to, for example, tumor antigens, in many instances, an individual's resident T cells are not sufficient to mount an appropriate immune response. To overcome this limitation, the inventor has developed in vivo treatments that are capable of enhancing the immune potential of T cells, providing a powerful tool to amplify the immune system.

Based on results illustrated in the following examples, it is now clear that antibodies directed against TcR/CD3 and other T cell surface structures can profoundly potentiate T cell function in vivo. This action of monoclonal antibodies was unexpected in vivo because a major clinical use of mAbs directed against T cell surface proteins has been to suppress, not to stimulate, the immune response to foreign antigens. Moreover, monoclonal antibodies (mAb) to T lymphocyte antigens have been used to suppress immune responses in vivo and in vitro by blocking T cell receptor-mediated antigen recognition, a property exploited clinically to prevent and reverse organ transplant rejection.

In the practice of the invention, an important aspect is the ability to identify appropriate immunopotentiation agents which can be employed in immunopotentiation compositions hereof. This identification is routinely accomplished through the use of assays which identify potentiation and/or activation of immune system cells. For example, the inventor routinely employs assays for activation of T cells such as might be exhibited as cytolytic activity by a responder cell such as activated CD8+ cells, against a target cell such as K562 cells. Alternatively, T cell activation can be read out by the production of lymphokines (e.g., GMCSF, IL-2, -Y-IFN) released by the responder cells. Such assays are well known in the art as illustrated by reference 64. Another useful assay employs thymidine incorporation as a measure of T cell proliferation. (65). Other possible assays include IL-2 receptor expression, phosphoinositide turnover, and even $Ca^{++}$ flux (66, 67).

In the context of the present invention, the inventor routinely employs the induction of cytolytic activity, lymphokine production and T cell proliferation as assays for immunopotentiation. Exemplary assays are set forth in Tables 1 and 2 below, which were employed to identify mAb 145-2C11 (29), the mAb specific for the 25 kd protein CD3-ε. The data set forth in these two tables together demonstrate the ability of the 145-2C11 mAb to activate T cells. In Table 1, an assay is set forth wherein the ability of the mAb to redirect lysis of cytotoxic T lymphocytes (CTLs) to irrelevant target cells is assessed. Details of the assay are as set forth in references 29 and 45. The results demonstrated that none of the alloreactive murine CTLs significantly lysed the human target cell K562 in the absence of mAb (Table 1). However, addition of the culture supernatant from the hybridoma secreting anti-CD3-ε mAb resulted in lysis of target cells.

The lysis was dependent on the presence of effector CTLs, as incubation of the K562 cells with the mAb alone did not result in target-cell lysis. None of several other antibodies, including anti-Lyt-2.2 and anti-LFA-l mAbs, that inhibited antigen-specific lytic activity were able to promote lysis of the K562 targets by the CTL effectors. This ability to redirect lysis of the BM10-37 CTL clone to the K562 target had in fact been used as the screening procedure for identifying the 145-2C11 mAb.

TABLE 1 mAb 145-2C11 Activates Murine T Cells; Evidenced by Induction of Non-antigen-specific Lysis

| | | | % Specific Lysis Target (K562) | | |
|---|---|---|---|---|---|
| Responder | Stimulator | mAb | E/T 100:1 | E/T 33:1 | E/T 10:1 |
| bm10 | B10 | None | 2.8 | 1.7 | 1.5 |
| | | anti-T3-ε (145-2C11) | 53.6 | 42.0 | 37.0 |
| | | anti-Ly-6C (144-4B11) | 1.0 | 0.6 | −0.1 |
| | | anti-Thy-1 (145-7E12) | 1.3 | −0.1 | 0.1 |
| | | anti-Lyt-2.2 (83-12-5) | 2.2 | 0.7 | −0.6 |
| | | anti-LFA-1 (H35-89.9) | 0.1 | 0.5 | 0.5 |
| YBR | B10 | None | 3.0 | 2.1 | 2.0 |
| | | anti-T3-ε | 44.3 | 34.0 | 23.5 |
| | | anti-Ly-6C | 3.7 | 2.9 | 2.1 |
| | | anti-Thy-1 | 3.5 | 0.8 | 1.4 |
| | | anti-Lyt-2.2 | 1.9 | 0.9 | 1.2 |
| | | anti-LFA-1 | 2.0 | 2.3 | 2.3 |

The induction of CTL activity was determined by incubating the effector CTL and the antigen negative human target K562 in the presence of 5 μl of culture supernatant for 8 hr at 37° C. Similar results were obtained by using a wide range of antibody concentrations (from 50 μl to 1 μl of culture supernatant). E/T=effector/target ratio.

In the studies set forth in Table 2, the mitogenic properties of the mAbs were assessed by proliferation assays. In particular, the ability of mAb 145-2C11 to induce T cell proliferation was studied. In these studies, T cells ($10^5$) were cultured in RPMI-1640 medium containing 10% fetal bovine serum and 50 uM 2-mercaptothanol with irradiated (2000 rads; 1 rad=0.01 Gy) spleen cells ($2\times10^5$) in the presence or absence of mAb and/or factors in flat-bottomed microwell plates. The recombinant human interleukin 2 was provided by Cetus (Palo Alto, Calif.). After 2 days, the cells were incubated with 1 uCi (1 Ci=37 GBq) of [$^3$H]thymidine per well for 18 hr, the samples were harvested, and incorporation of radioactive isotope was measured with a scintillation counter.

Thus, purified T cells were cultured with 145-2C11 or control mAbs in the absence or presence of costimulating factors. The 145-2C11 mAb induced significant proliferation in the absence of exogenous factors. However, the addition of either phorbol 12-myristate 13-acetate or recombinant interleukin 2 significantly increased the proliferative response. Finally, both Lyt-2$^+$ (CD8), L3T4$^-$ (CD4) and Lyt2$^-$ (CD8), L3T4$^+$ (CD4) splenic T cells proliferated in the presence of soluble anti-CD3-ε mAb. By comparison, a soluble anti-Vβ8-specific mAb, has been shown to strongly stimulate CD8 T cells but to only minimally affect CD4 lymphocytes. Thus, phenotypically distinct subsets of T cells might be differentially activated by antibodies specific for different components of the murine TCR-T3 complex.

TABLE 2 mAb 145-2C11 Activates T cells as Evidenced by Induction of T-Cell Proliferation

| | | | | [$^3$H]Thymidine incorporated, cpm × $10^{-3}$ | | |
|---|---|---|---|---|---|---|
| | Responder* | | | | Control | |
| Exp. | Strain | Treatment$^t$ | PMA$^f$ | rIL-2$^§$ | mAb$^¶$ | 145-2C11 |
| 1 | B10 | None | − | − | 1.0 | 61.5 |
| | | | + | − | 6.2 | 249.6 |
| | | | − | + | 5.2 | 258.0 |
| 2 | B10 | C | − | + | 2.6 | 90.4 |
| | | anti-CD8 + C | − | + | 3.9 | 161.6 |
| | | anti-CD4 + C | − | + | 7.0 | 57.9 |
| | | C | + | − | 3.1 | 137.1 |
| | | anti-CD8 + C | + | − | 5.2 | 128.3 |
| | | anti-CD4 + C | + | − | 6.9 | 54.3 |

*C57BL/10 T cells ($10^5$) were cultured with irradiated spleen cells (2 × $10^5$) as stimulators.
$^t$spleen cells were incubated with antibodies to the CD8 or CD4 molecules followed by rabbit complement (C). In both cases, antibody treatment resulted in the elimination of >95% of the corresponding cell population, as judged by flow cytometry.
$^f$Phorbol 12-myristate 13-acetate (10 ng/ml).
$^§$Recombinant interleukin 2 (50 units/ml).
$^¶$mAb 145-8D10.

Figure 3:
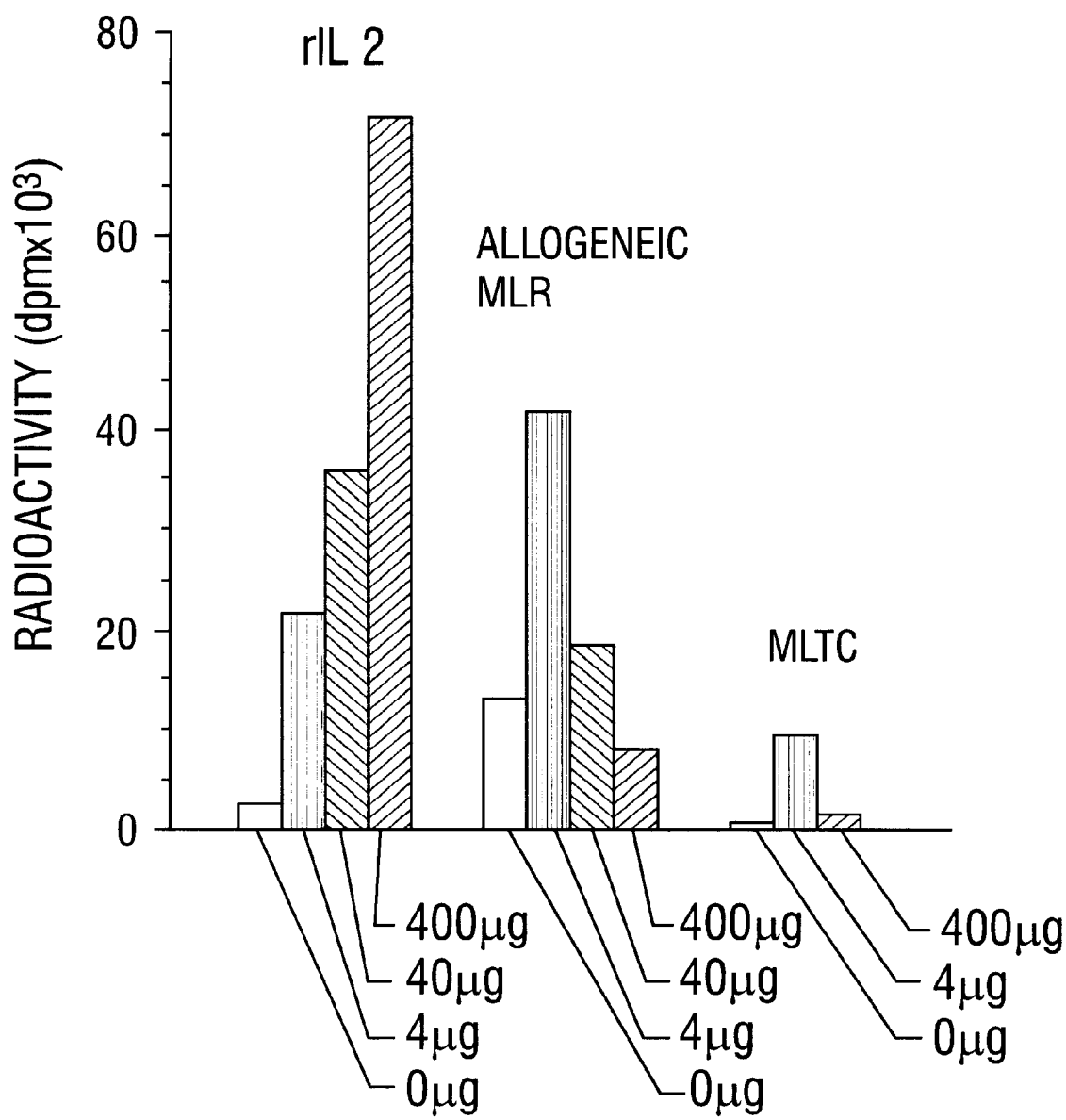
FIG. 3. In vitro proliferation of lymph node T cells from anti-CD3 treated C3H mice. Eighteen hours after intravenous anti-CD3 administration, lymph nodes were removed from animals and the cells ($1 \times 10^5$ cells for mixed lymphocyte reaction (MLR) and mixed lymphocyte tumor culture (MLTC)) were incubated in medium that contained irradiated syngeneic spleen cells ($2 \times 10^5$) plus recombinant IL-2 (rIL-2), or irradiated allogeneic (C57BL/10) spleen cells, or mitomycin C-treated Pro-4L tumor cells ($5 \times 10^3$). Proliferation was measured by [$^3$H]thymidine uptake at 48 hours (rIL-2) or 72 hours (MLR and MLTC). Background uptake (generally less than $5 \times 10^3$ cpm) was determined from lymph node cells stimulated with syngeneic irradiated accessory cells, or from mitomycin C-treated tumor cells cultured alone, and was subtracted from values for treated cells. All assays were performed in triplicate; standard deviations were less than 5%. The results show that a) functional IL-2R is expressed on anti-CD3 treated cells; and b) anti-CD3 treated T cells responded more vigorously to allogeneic MHC and tumor antigens than did untreated cells under otherwise similar conditions.
Figure 4A:
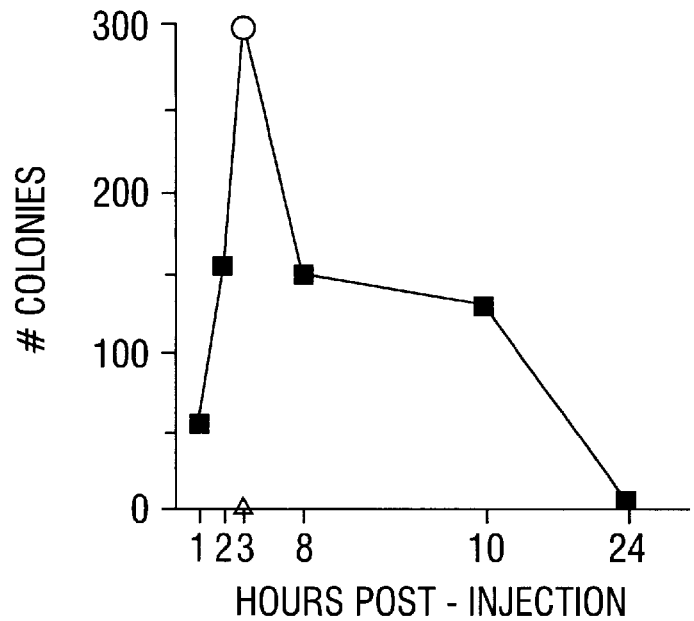
FIG. 4. Colony Stimulating Factor (CSF) in serum of mice after injection of anti-CD3. Pooled sera from three animals were placed at 6% final dilution with murine bone marrow cells, and the number of colonies were counted after 7 days. Each sample was tested in duplicate and the results were averaged. In all cases, duplicate values differed by no more than 5% A: Mice received 400 μg anti-CD3 Ig(■), or 250 μg of F(ab')$_2$ fragments of anti-CD3 (○). (The number of colonies at 3 h for anti-CD3 treated mice was more than 300.) B: Number of colonies after various doses of anti-CD3. Serum was collected 3 h after injection. These results show that anti-CD3 in vivo induces lymphokines including colony stimulating factors.
Figure 4B:
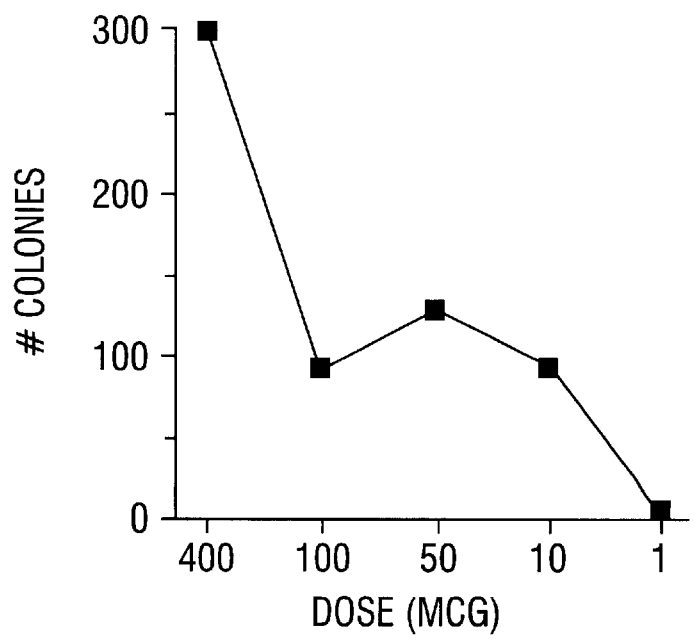

Thus, antibodies against CD3-ε (e.g., 145-2C11) have the ability to provide immunopotentiation in the forgoing assays, as measured by proliferation, secretion of lymphokines and the expression of interleukin 2 receptor (IL-2R). Similar phenomena occur following the treatment of mice with doses of, e.g., on the order of 4 μg to 400 μg anti-CD3 mAb in vivo (30; FIGS. 2–4). At higher doses, however (e.g., on the order of 40 μg to 400 μg) anti-CD3 mAbs also cause TcR coating, modulation and depletion of T cells from peripheral blood and lymphoid organs. Thus, the net result of treatment with high doses of anti-CD3 mAbs in vivo is immunosuppression. For this reason, the present invention is concerned with compositions and protocols which are tailored to allow the administration of relatively lower doses.

It is contemplated that assays such as those set forth above for T cell activation and potentiation can be employed in a variety of fashions to assist in achieving the goals of the present invention. For example, it is proposed that assays such as these can be employed for screening hybridoma colonies to identify those which secrete mAbs having the desired immunopotentiating effect. Similarly, assays such as these can be readily employed to screen for and identify other suitable immunopotentiation agents such as immunopotentiating bacterial or mycoplasmal proteins. Furthermore, assays such as these can be employed as an initial step in the determination of appropriate dosages in test animals (e.g., in terms of mg/kg body weight) which will provide immunopotentiation as opposed to immunosuppression.

Figure 5A:
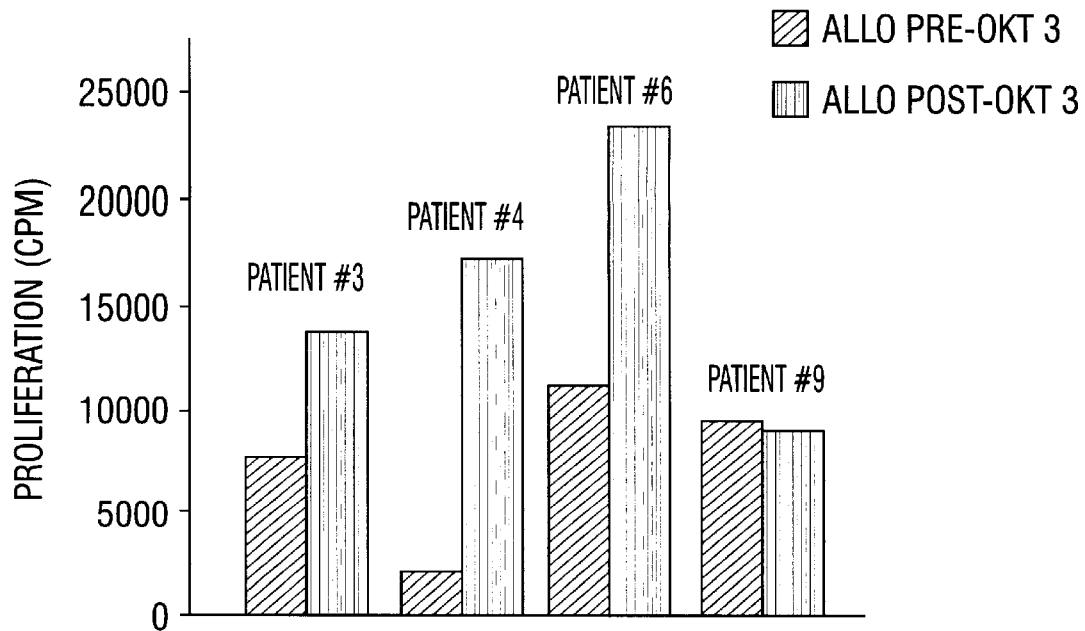
FIG. 5. Clinical Response to anti-CD3 (OKT3) Treatment. A: Increased allogenic MHC response in patients treated with OKT3. B: Proliferation of T cells before and after OKT3 treatment in the presence (cross-hatched bars) or absence (closed bars) of rIL-2 suggest that in vivo treatment with OKT3 activates human T cells.
Figure 5B:
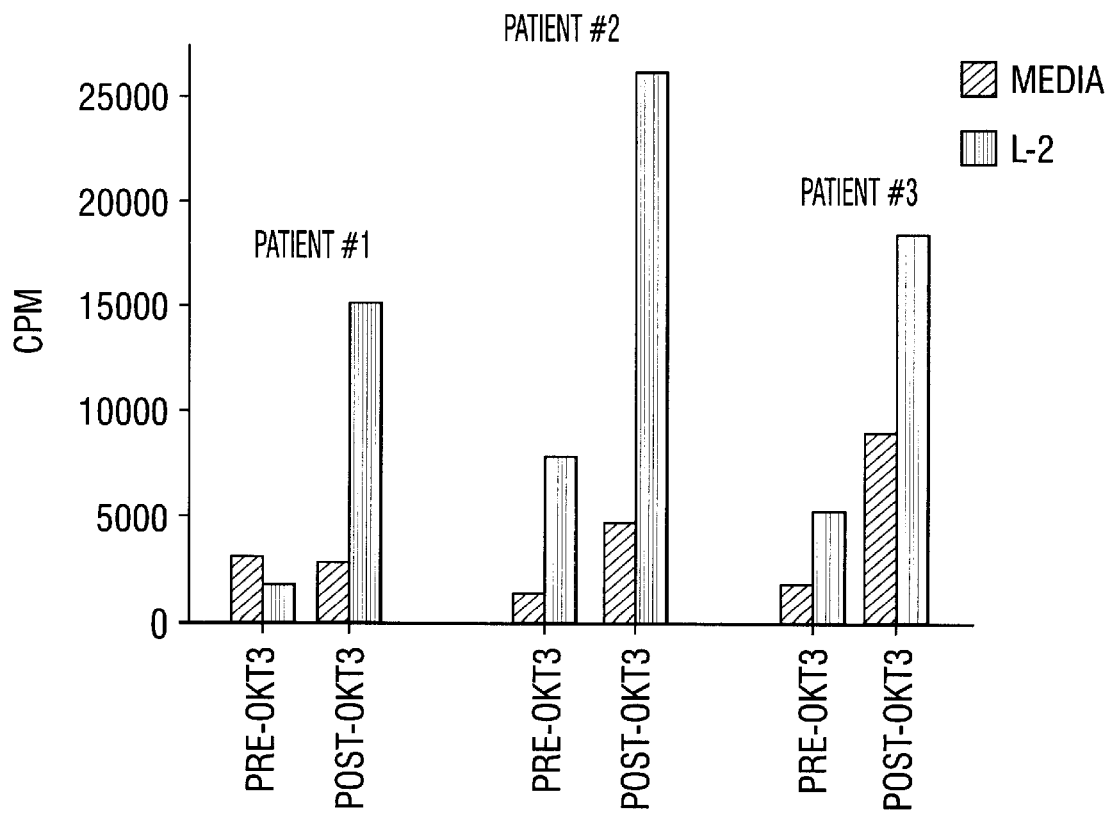

The foregoing information can, in turn, be employed by those of skill in the art to determine reasonable dosages which would likely be successful in human therapy. For example, anti-CD3 (OKT3) administered to humans during a clinical trial on the use of anti-CD3 in cancer treatment, is found to act in similar fashion to activate T cells as in the above test systems (FIGS. 5A and B).

Although immunopotentiating antibodies directed at activation antigens expressed on all T cells can be used in the practice of the present invention, it is proposed that antibodies or reagents specifically directed at T cell subsets are even more useful as immune adjuvants without producing associated immunosuppression, because this specificity ensures that the majority of T cells will remain unaffected.

Thus, in the practice of the invention, the potentiation reagents used will in certain cases activate all T cells, and in others subsets of T cells will be selectively activated.

T cell subsets are defined as individual families of T cells that share common features including cell surface proteins such as CD4 and CD8 which are expressed on 66% and 33% of the T cells, respectively, Ly-6 and CD28 expressed on distinct families of T cells, or the TcR proteins. (11, 15, 16)

Listed below in Table 3 are a series of preferred T cell epitopes which it is proposed can be employed in the practice of the present invention to generate immunopotentiating mAbs.

TABLE 3

Preferred T Cell Epitopes

1. Proteins in the T cell Receptor Complex (TcR)
   a. Non-polymorphic (Monomorphic) Epitopes
      (e.g. CD3-$\gamma$, $\delta$, $\epsilon$, $\zeta$ or epitopes from the
      constant region of the TcR $\alpha$, $\beta$, $\gamma$, $\delta$ chains)
   b. Polymorphic Subset Specific Epitopes
      (e.g. epitopes expressed on the variable
      portion of TcR, V$\alpha$, V$\beta$ V$\gamma$ or V$\delta$ chains)
2. Proteins Not Associated with the TcR
   a. Non-polymorphic (Monomorphic) Epitopes
      (e.g. Thy-1, CD2)
   b. Polymorphic Subset Specific Epitopes
      (e.g. CD4, CD8, Ly-6, CD28)

Figure 7:
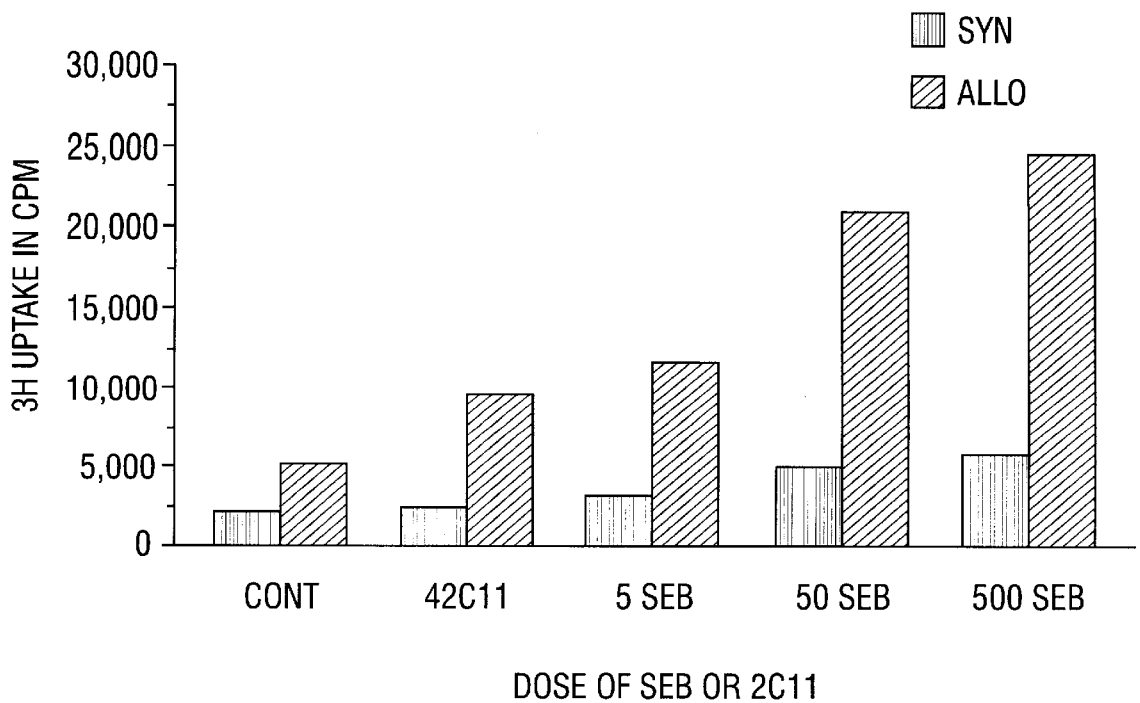
FIG. 7. Alloresponse of lymphocytes from C3H mice treated with Staphylococcus enterotoxin B (SEB) or mAb 145-2C11. The response as measured by cell proliferation ($^3$H uptake in CPM) was compared among control cells versus those treated either with mAb 145-2C11 (anti-CD3) or one of 3 doses of SEB. Cell proliferation was increased above control levels by either treatment. In addition, the stimulation by SEB showed a dose response.
Figure 9:
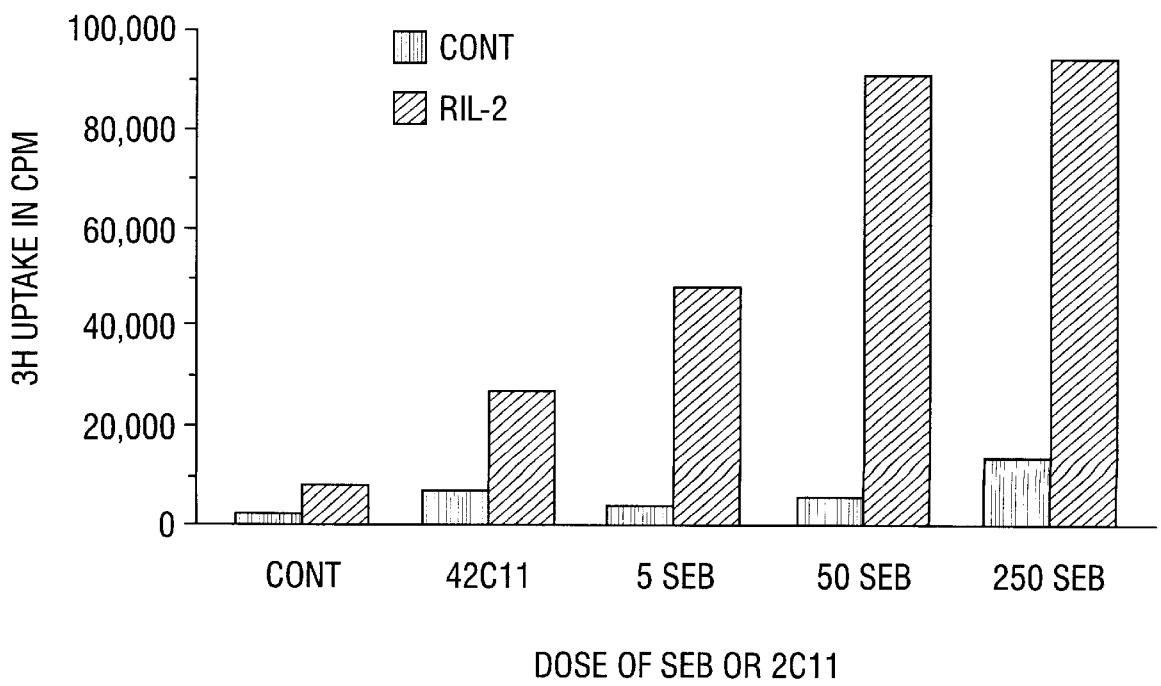
FIG. 9. Proliferative response to SEB. Lymph node cell proliferation was assayed by $^3$H uptake (CPM) in C3H mice at 18 hours after administration of SEB. rIL-2 response to SEB $^3$H was enhanced compared to controls or to 145-2C11-treated mice. In addition, there was a dose response (5, 50, 250 μg of SEB).
Figure 8A:
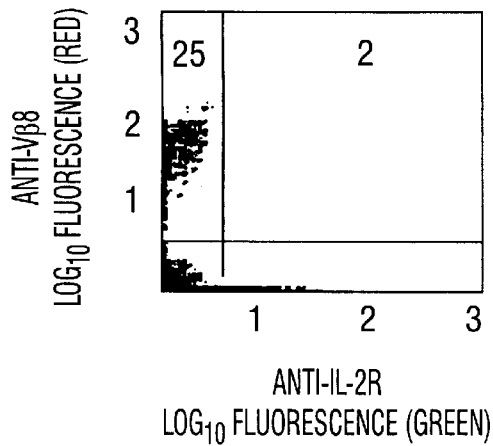
FIG. 8. IL-2R expression on T cells from SEB-treated mice. Mice were treated with increasing doses of SEB (0, 5, 50, 250 μg). Il-2R expression after 18 hours was compared using flow cytometry and showed enhanced expression. Dose response was observed.
Figure 8B:
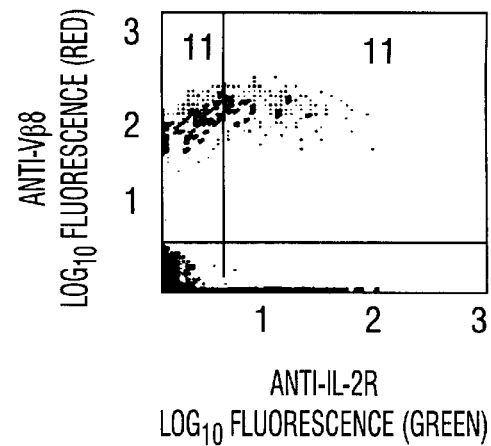
Figure 8C:
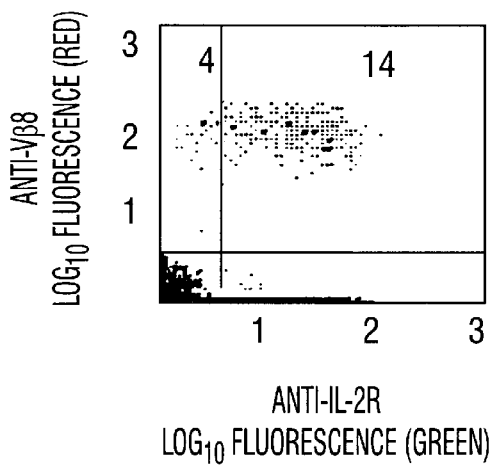
Figure 8D:
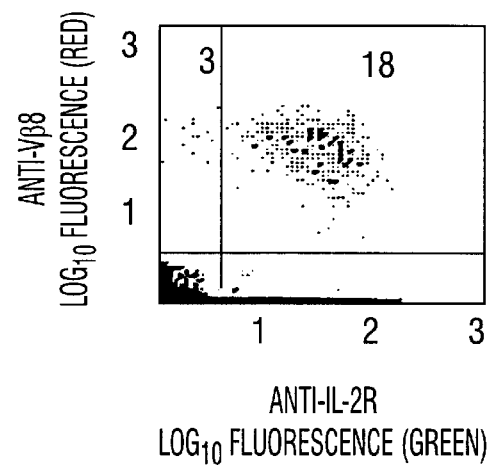

The response of the immune system to Staphylococcus enterotoxin (SEB) as an immunopotentiating agent is surprisingly stronger than, although qualitatively similar to, that seen in response to anti-CD3. (FIGS. 7–10). For example, SEB produced a dose responsive increase in allogeneic cell proliferation in mice (FIG. 7). In another assay for immunopotentiation, SEB administration exhibited a surprisingly enhanced IL-2R expression by T cells, and also showed a dose response. (FIG. 8). Moreover, proliferative effects evoked by SEB administration, as measured in the presence of RIL-2, were also of a surprising magnitude (FIG. 9).

It is of particular importance to note that, in contrast to anti-CD3, SEB application results in an expansion of a selected subset of lymphocytes, $V_\beta 8^+$ cells (FIG. 10). $V_\beta 8^+$ cells are a subset of T cells representing only 20%, and are important because they mediate a variety of immune responses. Thus, the ability of SEB to preferentially expand $V_\beta 8^+$ is of particular significance because it activates only a small subset of polyclonal T cells without directly affecting the majority of the T cell response.

B. Recruitment of Stem Cells and Enhancement of Transplantation

It is proposed that mAb therapy in accordance with certain embodiments of the present invention will have profound utility in connection with bone marrow transplantation. One of the biggest problems in bone marrow transplantation is the presence of T cells in the inoculum. Although several studies have suggested that depletion of T cells is critical in avoiding graft versus host disease (GvHD), T cells may play a critical role in engraftment. First, T cells may be required for limiting cytomegalovirus and Epstein-Barr virus infection in transplanted individuals. Second, when bone marrow transplantation is used in leukemia patients, specific T cells may provide potent graft vs. leukemia responses that eliminate residual tumor. Finally, T cells may provide a critical role in engraftment by producing a variety of growth factors such as GM-CSF. Thus, while total T cell depletion may eliminate GVHD, it may also compromise successful bone marrow engraftment.

It is proposed that aspects of the present invention may be useful in addressing this problem. There is apparently an interrelation between immunosuppression and immunopotentiation. The use of certain doses of activating anti-CD3 antibodies in vivo will not only prevent GvHD but will also activate endogenous T cells to produce hematopoietic growth factors that facilitate engraftment. Exemplary doses for achieving this effect will range from 5 mg/kg to 20 mg/kg, with about 10 mg/kg being proposed as optimal. The ability of immunopotentiating agents to increase hematopoiesis is demonstrated, e.g., by studies wherein it is shown that specific recruitment of stem cells such as myelocyte and bands occurs upon administration of such agents in humans, and increased colony formation in both mice and humans. In addition, it is proposed that mAbs directed at activation antigens present on stem cells or other hematopoietic cells may induce factor production or cell differentiation that will facilitate engraftment in the absence of T cells.

Importantly, high dose anti-CD3 treatment blocks graft vs. host disease. In an exemplary study, (C57BL/10×BALB/C)$_{F1}$ mice were first treated i.p. with 250 $\mu$g of the anti-CD3 mAb (145-2C11) and then exposed to 500 rads gamma-irradiation. Within one to two hours after irradiation, the mice were injected with spleen cells from a C57BL/10 mouse. Control mice, not pretreated with anti-CD3 died of GVH disease within 2 weeks. In contrast, 75% of mice given a single dose of anti-CD3 survived. Note that the anti-CD3 antibody was preadministered because it is proposed that circulating anti-CD3 antibody would modulate TcR from host T cells and thereby inhibit HvD reactions in experiments focused on enhancement of allogeneic bone marrow engraftment. Thus, because circulating anti-CD3 mAb depleted alloreactive T cells from the donor innoculum before GvH reactions can be initiated. (FIG. 13) Additionally, the mAb effects were examined by CSF assays, in vivo, and CFU-C, BFU-E and CSF assays in vitro.

Studies have demonstrated that mAbs may be directed to recognize activation molecules expressed on hematopoietic cells. Several antibodies have recently been identified that react with subsets of hematopoietic stem cells. Ly-6A, also known as Scal, is expressed on the earliest hematopoietic stem cells and studies have shown that mAbs directed at the Ly-6A epitope will activate T cells. A second mAb 143-4-2, which reacts with the Ly-6C epitope expressed on 40% of non-stem cells in the bone marrow has also been shown to activate T cells [27]. These results support the belief that mAbs can stimulate bone marrow.

Figure 11:
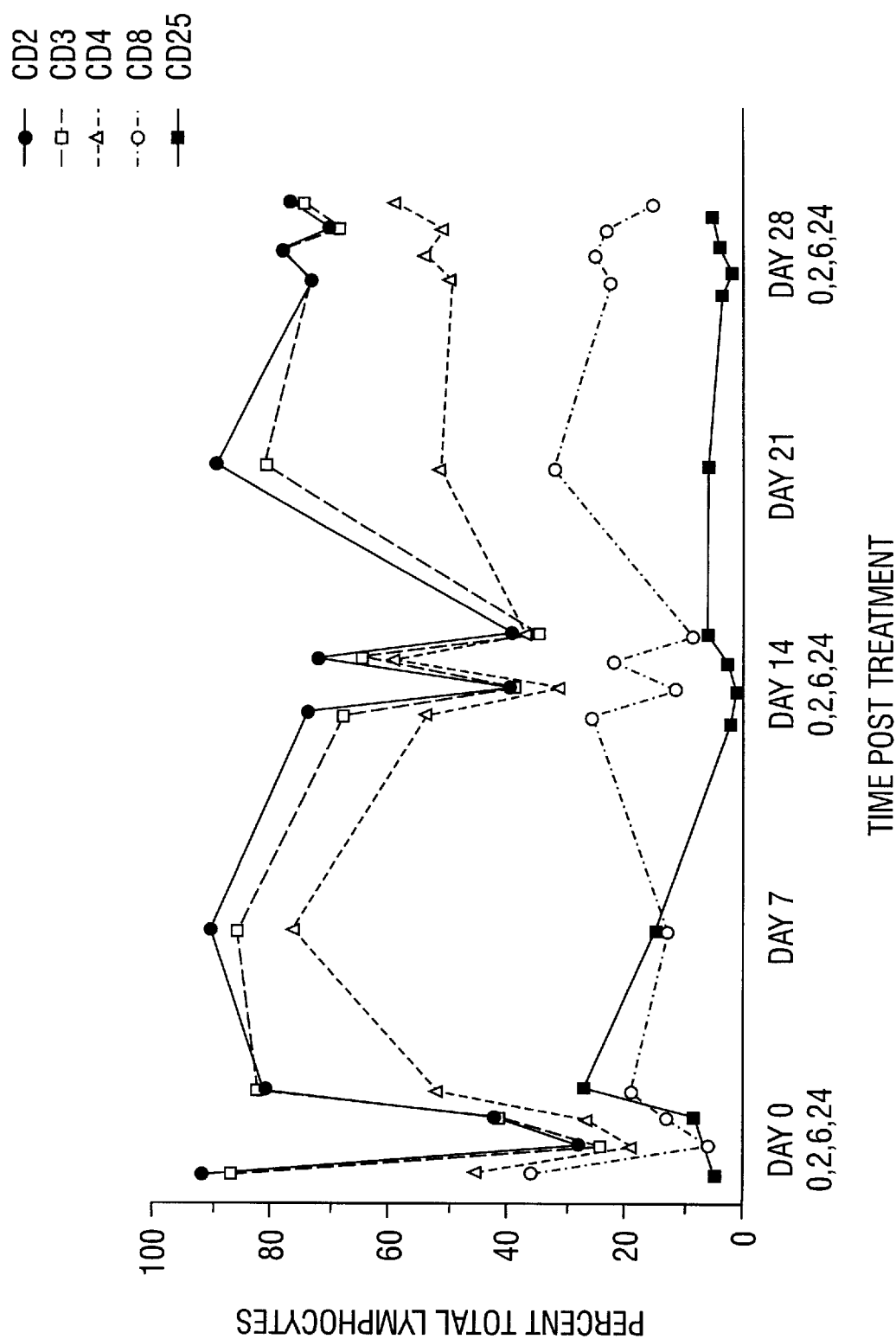
FIG. 11. Distribution of lymphocyte subsets after treatment with low doses of OKT3. After treatment with low dose OKT3 (100 μg/patient), there was observed an initial decrease in lymphocyte subsets, followed by a dramatic recovery of CD2, CD3 and CD4 positive cells, and to a lesser extent CD8 positive lymphocytes. In addition, cells were observed to be activated by the anti-CD3 treatment based on an enhanced expression of IL-2 receptor (CD25) on post-treatment lymphocytes.
Figure 12:
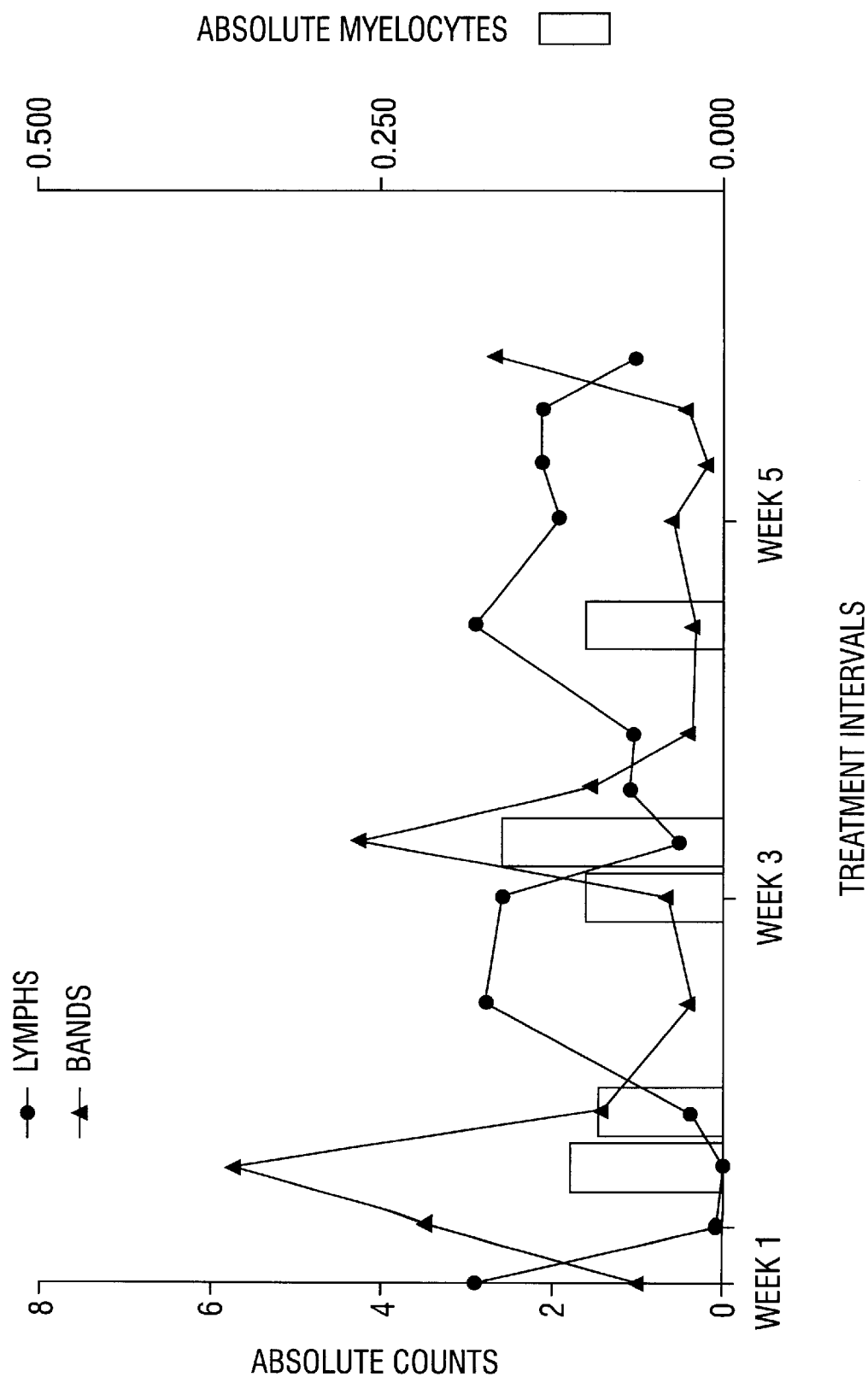
FIG. 12. Increased lymphokine production after treatment of humans with OKT3. In response to in vivo treatment of a patient with a 100 μg dose of OKT3, relative levels of hematopoietic progenitor cells (e.g., bands, myelocytes) are seen to increase dramatically in response to OKT3 administration.

The data in FIG. 12 demonstrates that administration of 1–3 doses of 100 μg results in profound increases in circulating stem cells, such as myelocyte and bands, directly in response to the administration. A single dose of 250 μg of anti-CD3 resulted in a >100-fold increase in CFU-C, BFU-E and total bone marrow colonies (FIG. 11) 4 to 10 days post injection. These increases in hematopoiesis have also been observed in humans treated with OKT3 (FIG. 12). These studies were carried out by histological examination and standard in vitro bone marrow colony formation assays in the absence or presence of exogenous growth factors erythropoetin or GM-CSF.

Similarly, Table 4 below presents data demonstrating the in vivo effects of anti-CD3 on hematopoiesis. The studies shown in Table 4 were performed by injecting 250 μg of anti-CD3 on day 0. Bone marrow cells were harvested on days 4 and 10 and examined in vitro for bone marrow colony formations as above. As can be seen, the administration of anti-CD3 to mice in all cases resulted in profound increases in hematopoetic progenitor cell activity.

TABLE 4

In vivo effects of anti-CD3 on hematopoiesis

|  | Day 1 | Day 4 | Day 10 |
|---|---|---|---|
| NL BM |  |  |  |
| + 0 | 0 | 0 | 12.3 +/− 2 |
| + 100 U GMCSF | 96 +/− 4 | 98 +/− 2 | 95.3 +/− 4 |
| + 3 U EPO  (CFU-C) | 7.3 +/− 2 | 11.5 +/− 3 | 19.3 +/− 1 |
| (BFU-E) |  |  | 17.8 +/− 3 |
| αCD3-Treated BM |  |  |  |
| + 0 | 27.3 +/− 3 | 253.3 +/− 5 | 302.8 +/− 6 |
| + 100 U GMCSF | 238.8 +/− 4 | 950+/19 | 416.3 +/− 6 |
| + 3 U EPO | 56.3 +/− 4 | 162.5 +/− 3 | 292.5 +/− 1 |
|  | 15.3 +/− 2 | 150.8 +/− 3 | 102 +/− 5 |

2. Immunopotentiation Agents As Immunoadjuvants

As noted above, an important aspect of the invention is the recognition that immunopotentiation agents described herein can be employed an "immunoadjuvants" in order to evoke an improved immune response to compounds against which such a response is desired. Thus, it is contemplated that such immunopotentiation agents may be formulated with or otherwise coadministered together with such compounds in order to improve or to develop an immune response against such compound. Various studies have been performed which serve to demonstrate the surprising potential for the immunopotentiation agents hereof to act in this manner as immunoadjuvants.

In one such study, the ability of various adjuvant substances were compared on the basis of their ability to promote the formation of antibodies against a Keyhole Limpet Hemocyanin (KLH) test antigen. The adjuvants studied were PBS (phosphate buffered saline control), CFA (complete Freund's adjuvant) and anti-CD3. The study was carried out as follows: 100 μg of KLH was injected on day 0 i.p. in the presence or absence of adjuvant. Mice were boosted on day 14 and bled at weekly intervals. Antibody activity was assessed in sera by standard ELISA.

Figure 6:
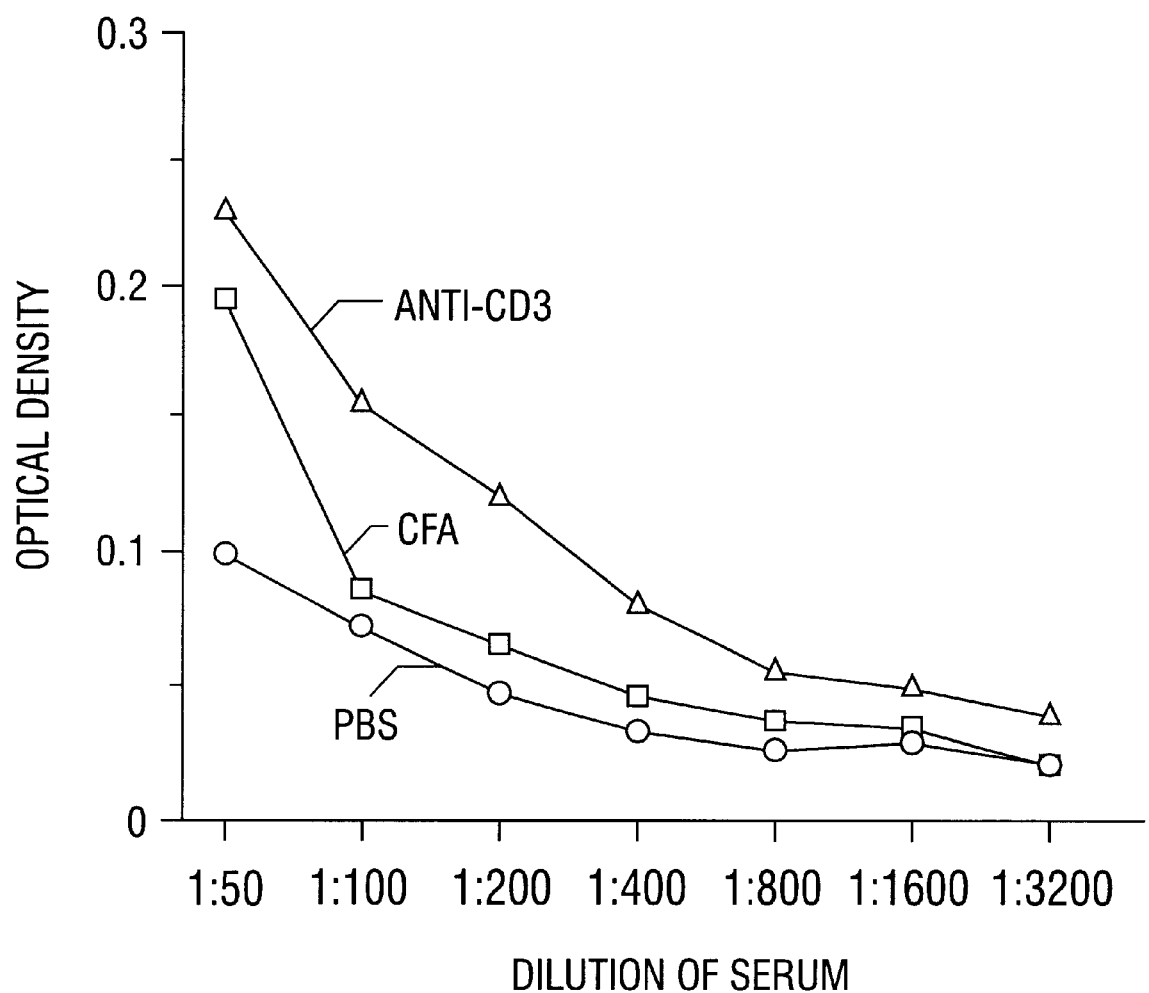
FIG. 6. Anti-CD3 augments immune response. Anti-KLH (Keyhole limpet hemocyanin) antibodies in mice treated with KLH using PBS, CFA, or anti-CD3 as immunoadjuvants. The results suggest anti-CD3 potentiates anti-KLH antibody responses.

The results of this study are shown in FIG. 6. As can be seen, at all dilutions of the resultant antiserum, the co-administration of anti-CD3 significantly outperformed the CFA adjuvant in terms of the specific anti-KLH titer which developed.

Figure 14:
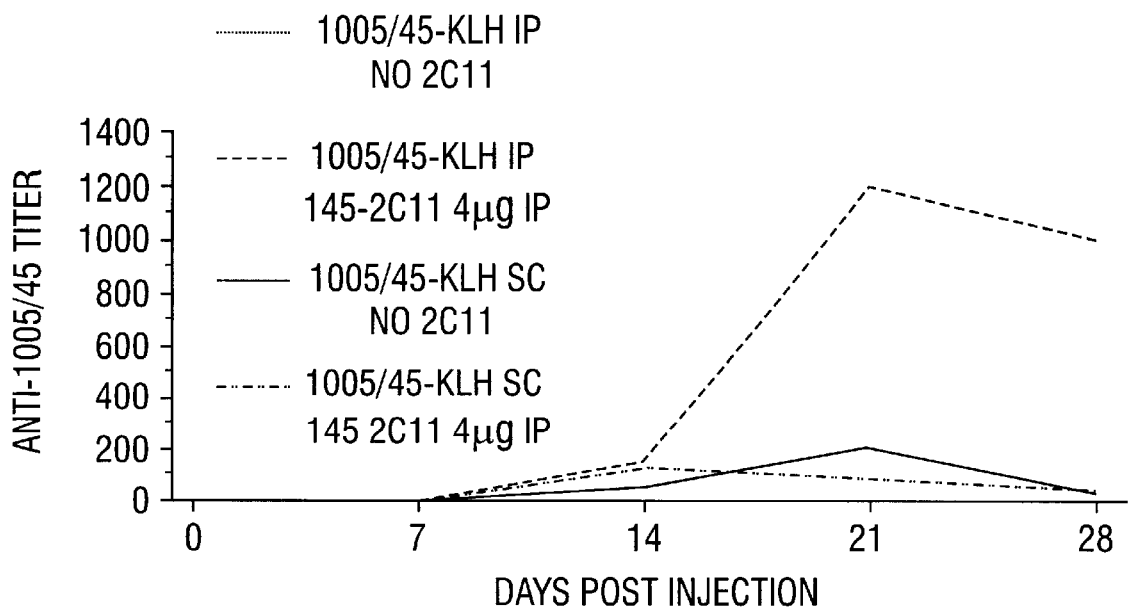
FIG. 14. Effects of treatment of mice in vivo with a combination of 1005/45-KLH and 145-2C11. This figure reflects studies conducted to demonstrate the adjuvant characteristics of anti-CD3 (mAb 145-2C11, an anti-murine CD3 mAb specific for a 25 kd protein CD3-ε) when co-administered with a KLH-linked peptide (1005/45; ref. 29), when administered intraperitoneally. C57BL/10 mice were administered 100 μg of the 1005/45-KLH conjugate, intraperitoneal (IP) or subcutaneously (SC), either alone or co-administered with 4 ug of anti-CD3 (145-2C11) IP. Titers of anti-1005/45 were assayed from 7–28 days post injection.

In another series of studies, mice were tested for their ability to produce specific antibodies in response to challenge by various routes with a KLH-linked peptide, termed peptide 1005/45-KLH, with and without co-administration of anti-CD3. This peptide is derived from the CD4-binding portion of the HIV-GP120 molecule. Mice were administered the test immunogen, 1005/45-KLH, either 100 ug subcutaneously (sc) or 100 ug intraperitoneally (i.p.) at day 0 and 14, followed by administration of 4 ug of anti-CD3 (145-2C11) i.p. in test animals. At various time points thereafter (7, 14, 21 and 28 days), the respective mouse sera was tested for the appearance of antibodies against 1005/45 (anti-1005/45 titer). As shown in FIG. 14, the results demonstrated a profound increase in the 1005/45-specific titer by day 21 in the 145-2C11-treated animals as compared to the controls. The strongest response, in terms of serum titers of anti-1005/45 antibodies, was in the group that received both the antigen and 145-2C11 intraperitoneal. (Table 5, FIG. 14) There was essentially no response in the control groups or in those treated subcutaneously. The results indicate the immunopotentiating effect of anti-CD3 as an adjuvant when administered in conjunction with a relatively non-immunogenic protein.

TABLE 5

SERUM TITERS OF ANTI-1005/45
ANTIBODIES IN C57BL/10
TREATED WITH INTRAPERITONEAL (IP) OR
SUBCUTANEOUSLY (SC) 1005/45-KLH AND 145-2C11

|  | Days post injection | | | |
|---|---|---|---|---|
| Tag # | 7 | 14 | 21 | 28 |
| (antigen SC, no 2C11) |  |  |  |  |
| 1 | ND | 100 | 400 | 50 |
| 2 | ND | ND | ND | ND |
| (antigen SC, 2C11 IP) |  |  |  |  |
| 3 | ND | 50 | 100 | 50 |
| 4 | ND | 100 | 50 | 50 |
| (antigen IP, no 2C11) |  |  |  |  |
| 5 | ND | ND | ND | ND |
| 6 | ND | ND | ND | ND |
| (antigen IP, 2C11 IP) |  |  |  |  |
| 7 | ND | 100 | 800 | 400 |
| 8 | ND | 200 | 1600 | 1600 |

Data are expressed as highest dilution at which antibody was detected in serum by ELISA.
ND = not detectable.

3. Heteroconjugates

Small peptides have been found to act as immunogens when used with adjuvants other than monoclonal antibodies or bacterial enterotoxins. However, activation of immune system components was not reliable enough to predict clinical success. Long term, specific immunity is due in many instances to the stringent requirements for T cell recognition of antigens in the context of the polymorphic MHC molecules. The use of immunopotentiating proteins, such as monoclonal antibodies and bacterial proteins, to activate T cells in the absence of the requirement for antigen/MHC interaction, coupled with the likelihood that most small peptides will express immunogenic epitopes even though they may not be recognized by the T cell or MHC proteins form a major foundation of this invention. One object of this invention was to directly couple a peptide to an immunopotentiating protein, e.g., monoclonal antibody or bacterial enterotoxin, to provide a more potent immunogen than a peptide alone. What has been achieved in this invention is to develop a "pass key" which tricks the cell into thinking it sees a foreign antigen being presented, causing it to be activated. By presenting a peptide either linked to an immunopotentiating protein, or in combination with it, the T cell activity is directed towards the unique antigen-specific B cell target. (FIG. 16 and 17).

For a heteroconjugate, the second protein is isolated and purified by standard methods from diseased or abnormal tissue, from an infectious agent, or by genetic engineering a specific amino acid sequence using standard molecular biology techniques. Embodiments of second proteins in general are shown in Table 6. A specific embodiment would be the amino acid sequence, T1, encoded within the gp 120 protein of the HIV virus: K Q I I N M W Q E V G K A M Y A.

TABLE 6

Embodiments of the second protein* in the heteroconjugate

| Category | Size | Example |
| --- | --- | --- |
| Hapten | Small Chemical Compounds | FITC (FIG. 7,8) |
| Peptide | 8–50aa | Peptide 18 |
| Protein | >50aa | gp 120 (HIV Virus) |

*Includes an epitope against which a humoral immune response is desired.

To complete formation of a heteroconjugate, cross-links are formed between the immunopotentiating protein and the second protein by use of any of the methods which link proteins to form bonds that are stable under normal physiologic conditions. Such methods include biotin-avidin bridges, SPDP functional groups, and cross-linking of maleimide and SH groups.

4. Immunotherapy and Immunization

This invention is also directed toward a method of stimulating an immune response in persons identified who are in need of such stimulation due to having diseases or infections. The heteroconjugate is prepared with a pharmaceutically acceptable excipient or diluent to form a therapeutically effective compound. Persons who are candidates for this treatment include those who have a tumor, are immunocompromised or have contracted AIDS or other viral, bacterial, fungal, or parasitic infections.

Another embodiment is to stimulate the immune response by administering only the immunopotentiating protein of the heteroconjugate not linked to the second protein. The immunopotentiating protein may be administered before, after or in conjunction with the second protein. Alternatively, a single immunopotentiating agent may be used.

For clinical use, the persons who are in need of treatment are identified and the monoclonal antibody which is specific for a non-polymorphic or polymorphic T cell surface protein is administered to the persons by intravenous route. The monoclonal antibody must not be immunosuppressive nor adversely affect CD3/TcR expression at the dose used. One embodiment disclosed is to use monoclonal antibody against the CD3 cell surface antigens associated with the TcR. The mAb mimics a physiologic antigen and bypasses the TcR antigen-specific recognition mechanism.

If the epitope is a tumor, treatment with doses of monoclonal antibody selected to be at levels which are not immunosuppressive, but immunopotentiating, prevents tumor outgrowth and also provides lasting tumor immunity. Methods disclosed in this invention enhance the immune potential of T-cells and other components of the immune system and provide powerful tools to amplify the immune system. An object of the invention is to augment the effects on the immune system of weakly immunogenic small peptides or proteins. For example, conjugating proteins to monoclonal antibodies produces a stronger response by bypassing the requirements of immunogenicity mandated by MHC restriction and antigen recognition by T cell receptor.

The strategy of this invention is to stimulate T cell immune reactivity using mAbs. T cell activation enhances the ability of an individual to reject a malignant tumor in a specific manner and produces long lasting tumor immunity. Therefore, the antigen-like effect of monoclonal antibodies to TcR/CD3 structures are disclosed as a means to specifically enhance immune function in vivo in tumor bearing individuals.

This invention allows for the direct interaction of the vital components of the immune response in developing strong cellular and humoral immunity. It is directed also toward protecting those who are not yet affected with the disease or condition by disclosing a vaccine comprising the immunogenic heteroconjugate described above. The use of this heteroconjugate does not require the interaction of the peptide with the major histocompatibility complex antigens, which presents a very significant advantage, that is, bypassing the polymorphic response which is usually a problem with the MHC system. All immune responses are dependent on the ability of T cells to recognize processed antigen associated with major histocompatibility antigens (MHC).

Any vaccine approach which utilizes HIV peptides or inactivated virus antigen must depend on the ability of antigenic peptides to bind the appropriate MHC antigens necessary to initiate an immune response. Specifically, the tremendous polymorphism of the MHC antigens expressed in the population and the variation of the virus, developing a successful HIV vaccine for general use faces major obstacles. Thus, developing an ideal form of immunotherapy and vaccines against, for example, AIDS, could be achieved by increasing the antigenicity of the peptide MHC interaction or boosting the activity of the immune cells, thus reducing the threshold of antigenicity necessary to trigger specific immune responses and memory following antigen exposure. A more general vaccine is created by use of the heteroconjugate which is an aspect of this invention because the extensive genetic diversity of the MHC is not a factor in binding to T cells. Given the highly polymorphic nature of both the MHC proteins and the TcR gene products, the number of peptides that are present in sufficient quantity to bind both the MHC and TcR, thus inducing an immune response, is small, factors limiting the success of vaccines.

The efficacy of vaccines, in particular those which may be weakly immunogenic, may be improved by modifying the foreign antigen such that it is more immunogenic, or allowing the use of peptides which are not immunogenic under normal conditions because they would not bind MHC, but which may constitute a conserved site on the major HIV viral proteins that is found in a large percentage of the population. In one embodiment, vaccines are comprised of heteroconjugates. Monoclonal antibodies which are used as the immunopotentiating protein in the vaccine include T-cell surface antibodies directed against non-polymorphic or polymorphic T-cell surface molecules. The second protein which is used as the other portion of the heteroconjugate includes those which are not capable of stimulating the immune system sufficiently to achieve immunization unless they are administered in a conjugate with the monoclonal antibody.

An object of this invention is an approach to therapy which activates the host antitumor cellular effector mechanisms, even though the epitope is only weakly immunogenic and could evade host recognition and rejection unless augmented. Major forms of immunodeficiency may be due to the inability of antigen to trigger a primary immune response due to suboptimal antigen presentation and T cell activation.

In addition to the administration of compositions for stimulating immunity, the present invention also contemplates that certain immunological products which are produced as the result of such an administration may provide a benefit to some individuals, particularly immunocompromised individuals. That is, it is contemplated that the immunopotentiating compositions of the present invention may be employed to produce antibody compositions, such as gamma globulin fractions, which may be administered to individuals for the development of passive immunity.

For such embodiments, immunopotentiating compositions hereof which contain appropriate compounds against which an immune response is desired, whether such compositions are in the form of "adjuvant" compositions or heteroconjugates, are administered to disease-free individuals in an amount effective to elicit a specific immune response against the second compound. The resultant gamma globulin fraction is then obtained and purified by well known techniques, and administered in effective amounts to individuals in need of such treatment. Note that in addition to the use of immunoglobulin fractions, the present invention contemplates that other immunological products, such as activated T and B cells will also be useful for such purposes, e.g., in the treatment of cancers and even HIV infections.

5. Summary

The development of the invention required production of the immunopotentiating agents, testing their effects in vitro, and finally developing their in vivo effects in mice as models, and in humans for purposes of treatment.

The in vivo effects disclosed in this invention are not absolutely predictable from the in vitro effects because an intact organism's response reflects interactions of a complex immune system, whereas, in vitro, individual components can be controlled, and system interactions are difficult to simulate. In vivo, various components which reacted separately in the laboratory in certain fashions, may not interact appropriately when their actions are combined.

METHODS

The following examples present methods for preparing the immunopotentiating agents described herein, methods for administering them to non-humans or humans, and methods for assaying their effects. The techniques employed in the following examples reflect those found or contemplated by the present inventor to constitute preferred modes for the practice of the invention. However, those of skill in the art will appreciate in light of the present disclosure that many modifications and changes may be made in the disclosed techniques without departing from the spirit and scope of the invention.

Example 1

Preparation of the Immunopotentiating Agents

1. Single Agents
A. Monoclonal Antibodies

Monoclonal antibodies were prepared against specific classes of T cell epitopes. These classes are listed in Table 3. In the following embodiment, methods for preparing a monoclonal antibody against a nonpolymorphic epitope, CD3, and polymorphic epitope V$\beta$x where x=a specific chain in the variable part of the TcR complex, are described:
(1) Preparation of a mAb Directed Against the Murine CD-3 Chain of the TCR Complex Monoclonal antibodies were generated which are reactive with the T cell surface structures expressed as alloreactive cytotoxic T cell (CTL) clones and involved in T cell activation. mAbs specific for these cell surface molecules were identified using an assay (developed by Bluestone, the redirected lysis assay (33), see also Example 13) based on the ability of antibodies reactive with the TcR complex to induce antigen-specific CTL to lyse cells which are not their natural targets. This activity depends on the ability of the antibody to both activate the CTL via the TcR and multivalently crosslink the effector to the target cells via the Fc receptor (FcR) on the target cells. Several mAbs have been derived in this fashion. This assay is one way to select for mAbs that activate T cells, and increase proliferation and lymphokine release.

The mAb, 145-2C11, was derived by fusing spleen cells from an Armenian hamster immunized with a murine CTL clone to SP2/0 cells, and screening the resulting hybridoma supernatants in the redirected lysis assay. This mAb immunoprecipitated the complete TcR complex using non-ionic detergents but reacted specifically with a 25-kD protein component (CD3-$\epsilon$) of the antigen-specific TcR complex. 145-2C11 mAb may also be obtained by growing hybridoma cells in an Acusyst P machine (Endotronics, Minn., Minn.) and then collecting the supernatant. Antibodies are then purified by 50% ammonium sulfate precipitation followed by gel filtration on an ACA 34 Ultragel column [BF Biotechnics, Savage, MR]

Another mAb, 143-4-2, was derived by fusing spleen cells from a BALB/c mouse immunized with a murine CTL clone and screened as in Example 13. This mAb defines a novel cell surface molecule involved in T cell activation. The expression of the 143-4-2 defined epitope was expressed on the Ly-6C molecule and was restricted in its lymphoid expression to bone marrow cells and to a subset of peripheral CD8+ cells (34). The anti-Ly-6.2C antibody can promote the lysis of target cells that do not bear antigens by alloreactive CTL clones and, in the presence of cofactors (PMA or IL-2), induced a subset of CD8+ cells to proliferate, perhaps through an autocrine pathway. Although the antibody described has antigen-like effects as described for anti-TcR complex reagents, it was shown that the Ly-6.2C molecule was not associated on the cell surface with components of the TcR complex. These included biochemical analyses, phenotypic studies and functional studies that showed that, unlike activation via the TcR/CD3 complex, Ly-6.2C-mediated activation was not inhibited by anti-CD8 mAbs (35). Nevertheless, cell surface expression of the TcR complex is required for optimal triggering of T cells via the Ly-6.2C molecule.

mAbs were purified by ion exchange chromatography and gel filtration. F(ab')2 and Fab fragments were prepared by pepsin and papain cleavage of purified antibody, respectively (36).

Additional mAbs were prepared that can be employed as immunopotentiating proteins in vivo to activate T cell subsets and hematopoietic stem cells. These include: UC3-10A6 and UC7-13D5 mAbs which are specific for the TcR δ receptor; UC3-7B7 which is specific for Thy-1; 145-4B11 and D7 (obtained from Tom Malek, Miami, Fla.) which are specific for Ly-6A (also known as the Sca1 antigen expressed on bone marrow stem cells); and H597.57, an anti-TcRαβ mAb (Ralph Kubo, Denver, Colo.).

(2) Preparation of a mAb Directed Against Vβx, Wherein x is a Specific Chain, e.g., Vβ2

Immunopotentiating proteins disclosed in this invention comprise monoclonal antibodies prepared as follows:

a. expand lymphocyte cell cultures by standard methods (37); use limiting dilution or hybridoma technology to clone T cells or produce T cell hybridoma (38) thereby being able to select discrete activation of cells from a single progenitor cell (clone);

b. use molecular probes or mAb to determine Vβx usage; this will identify all clones which express Vβx, (although these clones will also express other T cell antigens including a Vα chain, CD3 chains, and non-TcR associated proteins);

c. use clones or extracts of the clones expressing Vβx to immunize animals (mouse, rat or hamster), by standard techniques (39);

d. using spleens from the immunized animals, prepare hybridomas by standard techniques (40)

e. screen the hybridomas for those which satisfy both of the following criteria:
  1) activate T cells (determined by assays described in Example 13) (Note: of 1000–2000, mAb screened, a minority will activate T cells)
  2) produce a monoclonal antibody directed to the T cell clone;

f. select monoclonal antibodies which are specific only for Vβx, by eliminating mAb which activate clones which express with other Vβ proteins, based on the reactivity pattern of different Vβ-expressing clones, and biochemical analysis of TcR usage.

g. confirm that the antibody is specific for Vβx by biochemical techniques including immunoprecipitation and Western blots of the TcR antigen or Vβx and other T cell clones.

B. Preparation of an Immunopotentiating Agent Wherein this Agent is a Microbial Protein which Activates T Cells Any microbial component, e.g. a bacterial enterotoxin, may be assayed for T cell activation. Enterotoxins may by purchased from biochemical suppliers. Toxins that satisfy criteria of activation assays may be subjected to standard protein purification techniques, gel filtration and exchange chromatography. (1) At each step of the purification, the resulting product is assayed to determine whether the ability to activate T cells is preserved. Preferred epitopes may be selected from those shown in Table 3.

Example 2

Activation of T-cells by Administration of Anti-CD3

To evaluate whether low doses of anti-CD3 were effective as activating T cells in mice, mice were given different doses and their lymph nodes and spleen cells were examined for IL-2R expression by flow-cytometry. IL-2R expression was enhanced at the three doses tested (4, 40 and 400 micrograms) and plateaued at 400 micrograms. (FIG. 2). When the same lymphoid cells were incubated in media containing human rIL2, their proliferation was enhanced in proportion to their IL-2R expression. The immune suppression which results from a dose of 400 microgram of anti-CD3 was the result of T cell depletion, T cell receptor blockade and modulation of the TcR complex. The net result was that the amount of cell surface CD3 available to react with antigen was decreased, rendering the T cell unable to respond to antigenic stimuli because efficient antigenic specific activation depends on the presence of intact TcR. Therefore the quantity of available CD3 on lymph node cells from control and treated mice were examined 18 hours after treatment. Cells were stained with fluorescein isothiocyonate (FITC)-conjugated anti-CD3 and Thy-1+ T cells and were examined. (FIG. 2). Optimal conditions for anti-CD3 mediated T cell activation are those in which the concentration was 4 μg, low enough to permit activation without adversely affecting CD3/TcR expression. Additional evidence that the low dose anti-CD3 treatment not only non-specifically activated T cells but increased immune responsiveness was obtained from allogenic mixed lymphocytes reaction (MLR) and mixed lymphocytes tumor culture (MLTC) studies.

Example 3

Effect of Anti-CD3-Treatment on Sendai Virus Infection in Mice

The purpose of this example was to test the effect of mAb treatment on infection. Administration of low doses of anti-CD3 prevented the lethal pneumonia caused by the Sendai virus in >60% of mice. Anti-CD3 treated, virally-infected mice also developed lasting virus-specific immunity as evidenced by their ability to withstand a subsequent dose of Sendai virus of 1000 times the $LD_{50}$ dose. Treated mice also developed a Sendai virus specific DTH and antibody response similar to mice immunized with a non-virulent Sendai virus vaccine. Interestingly, the 129/J strain of mice were also protected by the anti-CD3 treatment. Because virus susceptibility in these mice has been shown to be caused by an inadequate generation of NK cell responses, it appears as if NK activity induced by the mAb treatment contributes to viral protection. (51)

Example 4

Anti-CD3 Prevents Malignant Progressor Tumor Growth in Mice

The purpose of this example was to determine the feasibility of immunotherapy designed to prevent tumor outgrowth and induce tumor immunity by administering anti-CD3 in vivo to activate T cells. This possibility was tested in mice with the eventual objective of pursuing similar strategies in humans.

Effects of the anti-CD3 treatment on malignant tumor growth in vivo were tested in mice. The C3H fibrosarcoma 1591-Pro-4L a weakly immunogenic ultraviolet-light-induced murine tumor that lacks cell surface CD3 and FcR does not react directly with the anti CD3 used for treatment. This malignant tumor grows progressively in 95 percent of normal CD3H mice and eventually kills the mice by infiltrative growth without macroscopic evidence of metastases.

None of the mice treated with 4 μg of anti CD3 developed tumors in this experiment. (Table 7). Animals treated with 4 μg of anti CD3 also developed tumor immunity because they failed to develop tumors following a second inoculation of Pro-4L 60 days later, despite no additional intervening monoclonal antibody therapy, whereas control animals challenged with tumor fragments at that time developed tumors. Treatment with F(ab')$_2$ is immunosuppressive but does not activate T cells and had no effect on tumor growth.

Immunopotentiating effects include increased tumor specific T cells, lymphokine-activated killer cell activity, increases in tumor necrosis factor (TNF) detected in the serum of treated, not control mice. Findings reported in Table 7 were confirmed using a metastatic tumor system MCA102. Lung metastases in mice having established MCA102 tumors are significantly reduced by the mAb treatment. In one experiment, mice injected with tumor alone developed a mean of 105±26 lung metastases while mice treated with anti-CD3 mAb 3 or 10 days after tumor inoculation developed 25±6 and 44±14 lung metastases respectively.

TABLE 7

Summary of Tumor Incidence at
Day 28 in Anti-CD3- Treated Mice
There was no recurrence, late outgrowth, or tumor regression after 28 days. The P value ($X^2$ method) for the difference between the control animals and those treated with 4 μg of anti-CD3 was P < 0.001.

| Treatment group (three separate experiments) | Tumor incidence (day 28) no. with tumor/ total no. (%). |
|---|---|
| Control | 42/44 (95) |
| Anti-CD3 (4 μg) | 11/31 (35) |
| F(ab')$_2$ anti-CD3 (2.6 μg) | 9/10 (90) |

*p < 0.001

Example 5

The Use of Staphylococcal Enterotoxins (SE) as Immunopotentiation Agents

The recent demonstration that Staphylococcal enterotoxins (SE) specifically activate T cells which express certain Vβ subsets (55) provide an approach for in vivo T cell activation in accordance with the present invention. These reagents, which activate in vivo have several advantages: 1) The SEs activate more than one Vβ-subset in vivo; 2) The SEs cause minimal TcR modulation and immunosuppression at low doses; 3) The SEs induce T cells to proliferate in vivo; and 4) Results using the SEs can be directly related to man since these reagents react with human T cell subsets in a similar manner (56).

Results of studies with SEB are presented in Tables 8a and 8b below. As shown in Table 8a, in vivo administration of SEB results in a selective activation of Vβ8$^+$ T cells. Moreover, the studies shown in Table 8b demonstrate that six of twenty mice treated with four μg of anti-CD3 developed tumors following tumor inoculation and, the administration of 50 μg of SEB resulted in tumor development in five out of twenty one cases.

TABLE 8a

IL-2 Receptor Expression on
T Cells from SEB Treated Mice.

| SPLEEN/ LYMPH NODE | % CD3$^+$ IL-2R$^+$ | % CD3$^+$ IL-2R$^-$ | % Vβ8$^+$ IL-2R$^+$ | % Vβ8$^+$ IL-2R$^-$ |
|---|---|---|---|---|
| CONTROL SPLEEN | 1 | 25 | 0 | 5 |
| ANTI-CD3 (4 μg, 18 HR) | 20 | 7 | 6 | 0 |
| SEB (50 μg, 18 HR) | 4.5 | 17 | 4 | 0 |
| CONTROL LN | 5 | 65 | 2 | 18 |
| ANTI-CD3 (4 μg, 6 DAYS) | 4 | 64 | 2 | 21 |
| SEB (5 μg, 6 DAYS) | 4 | 64 | 2 | 37 |

TABLE 8b

Tumor regression in anti-CD3
and SEB treated mice.

| Group | Tumor Incidence (Day 28) |
|---|---|
| CONTROL | 13/16 |
| ANTI-CD3 (4 μg) | 6/20 |
| SEB (50 μg) | 5/21  p < 0.01 |

Example 6

Alloresponse and Anti-tumor Response to SEB

To test the proposed use of SEB for immunopotentiation, C3H mice were treated either with anti-CD3 (145-2C11) or with one of three doses of Staphylococcus enterotoxin (5 μg, 50 μg, 500 μg). There were untreated controls. Both syngeneic and allogeneic responses were determined by $^3$H uptake of lymphocytes. As shown in FIG. 7 treatment with this single agent promoted an allogeneic response. A clear dose effect was also observed.

The surprising proliferative response of mouse lymphocytes to SEB alone, compared to anti-CD3 is shown in FIGS. 7–10, indicating that these enterotoxin are useful for immunotherapy. In fact, mice treated with SEB showed a significantly lower tumor incidence (Table 8b).

A difference was found between responses of the immune system to a single agent in the embodiment of anti-CD3 versus SEB. Anti-CD3 appeared to induce a more generalized response, whereas SEB could be directed to activate specific T-cell subsets. FIG. 8 presents results of SEB treatment of mice in vivo, in which IL-2R expression showed a clear dose response effect. Specific and preferential stimulation and expansion of Vβ8+ cells in the SEB-treated mice is further shown in FIG. 10.

Example 7

Response of Human Lymphocytes In Vivo to OKT3

Confirming the anti-CD3 responses in animal models, FIGS. 5A and B, 11, 12 illustrate the response of human cells to low doses of OKT3. Different lymphocyte subsets show a similar pattern of response, but different absolute percentages of total lymphocytes. These results are from the ongoing clinical trial of OKT3 in treating patients with cancer. The methods for this trial are described in Example 12.

Example 8

Anti-CD3 Treatment Abrogates Graft Versus Host Disease (GVHD)

Figure 13:
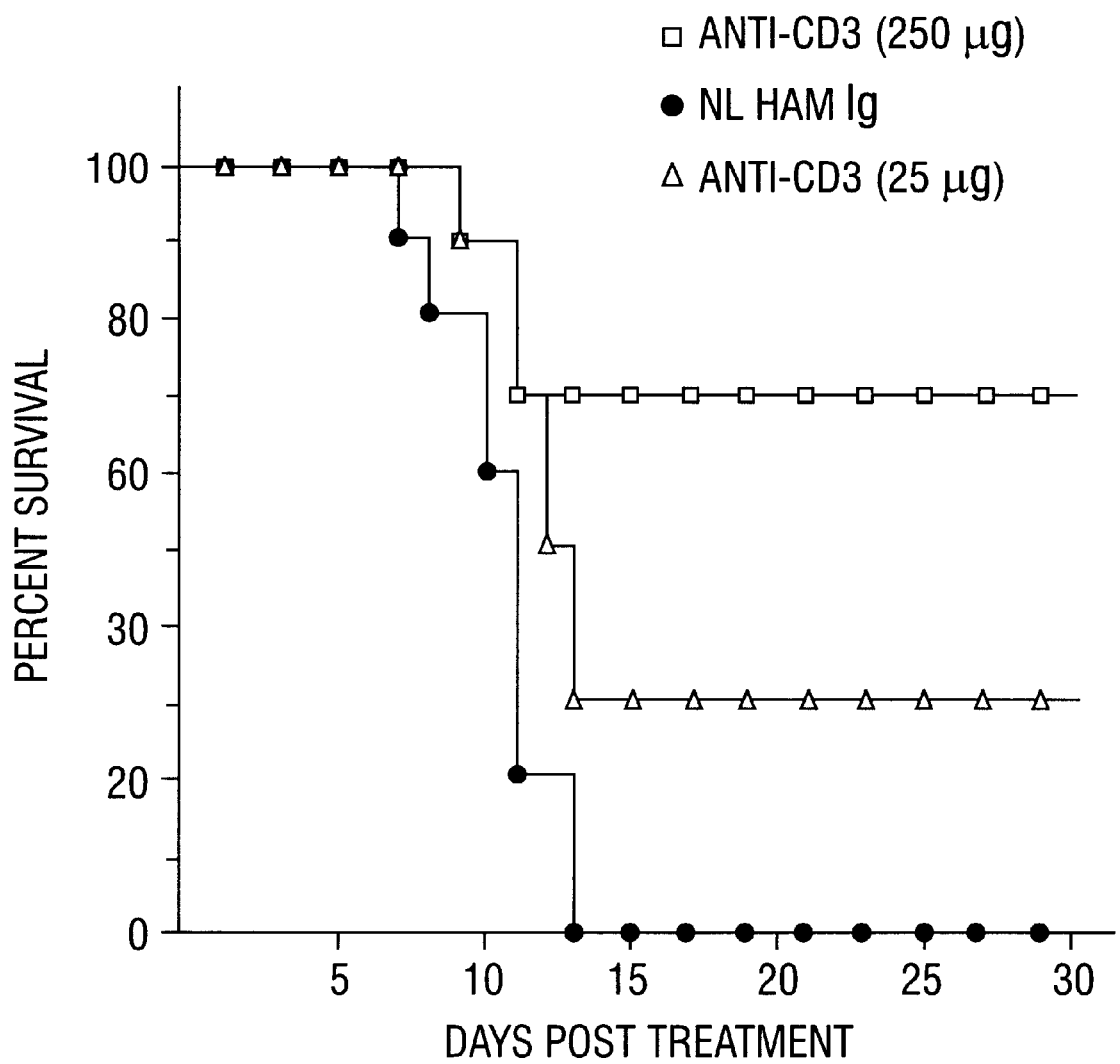
FIG. 13. Survival of grafts as a function of treatment with anti-CD3. In the study reflected by this figure, the ability of anti-CD3 to abrogate graft versus host disease (GVHD) was tested in a murine model wherein the mAb treatment also enhanced bone marrow engraftment. The study was carried out as follows: (B10×B100.BR)F$_1$ mice were sublethally irradiated with 500 RADs and injected with a lethal dose of GVH reactive B100.BR spleen cells in the presence or absence of immunosuppressive anti-CD3. The results, as displayed in the figure, show that when a control antibody was administered (normal hamster Ig), there was no survival by day 13. However, at the same time point, survival was about 25% for lower dose administration of anti-CD3 (25 μg) and a remarkable 75% at the higher dose (250 μg) suggesting the anti-CD3 had prevented graft v. host disease. Median survival was 11 days in controls and 12 days in animals treated with the low-dose of anti-CD3 (25 μg). Survival in the high dose anti-CD3 group plateaued at 75%.

The use of anti-CD3 will depend on the clinical condition. Depending on this, doses are selected. Mice were treated with 500 R radiation to suppress their immune response thereby facilitating transplantation. After 13 days, however, the graft was rejected in control animals. Dramatic increased survival of 75% was observed at the same point in time for animals treated with 250 μg of anti-CD3, and 30% survival after 25 μg of anti-CD3. (FIG. 13). This effect is believed due to induced hematopoesis which revitalizes the graft.

Example 9

Use of a Hapten or Peptide as a Second Protein in a Heteroconjugate or as a Combination Administered Concurrently Fluorescein isothiocyanate (Sigma) or Dinitrophenol (DNP) in borate buffer, pH 8.5 for 4 hours at 22° C. are examples of haptens tested for this purpose.

Examples of other second proteins are synthetic peptides of HIV, 13–23 residues long prepared by the multiple simultaneous peptide method of solid-phase synthesis in polypropylene mesh. These are coupled to the anti-CD3, BSA OVA or KLH using Maleimide as described in Example 2C. vSC-8 (recombinant Vaccinia vector containing the bacterial LACz gene), and vSC-25 (recombinant Vaccinia vector expressing the HIV env glycoprotein gp160 of the HTLV $III_b$ isolate of HIV structural or regulatory proteins) is used. Mice are conventionally immunized with 100 μg HIV/pep-KLH, or HIV/pep in Complete Freund's Adjuvant (Difco Laboratories) intraperitoneally 1–12 months before use either concomitantly or after injection of 4 μg of anti-CD3 mAb. Alternatively, mice may be immunized with anti-CD3 coupled FITC or HIV peptide.

Although concomitant treatment of mice with anti-CD3 mAb augmented antibody production specific for the FITC hapten, the most profound effect occurred when the anti-CD3 was directly coupled to FITC (FIG. 16). Anti-CD3-coupled TNP, FITC, and Ovalbumin (OVA) peptides are alternative immunogens. These studies provided insights into the ability of anti-CD3 to augment T cell and B cell immunity. They also provided the basis for an analysis of the ability of anti-CD3/hapten heteroconjugates to induce immunity by direct T cell/B cell interactions that may alter MHC restriction and IR gene control. These studies are best performed using in vitro plaque forming cell (PFC) responses or ELISA to examine the immunogenetics of antibody production. For instance, utilizing classic MHC restriction analyses to study the role of MHC/peptide interactions in anti-CD3 augments immunity, studies have shown that certain mice are low responders to OVA, depending on their MHC haplotype. The low response was due to the inability of carrier-specific T cells to recognize OVA peptides in the context of self MHC.

Anti-CD3 is coupled to various OVA peptides including amino acids 323–334 which is known to be immunogenic in H-$2^d$ strains as well as other peptides not capable of generating an immune response (46). These experiments were performed to assay the ability of anti-CD3/hapten heteroconjugates to induce immune responses in low responder haplotypes. In particular, the activation of B cells by a direct crosslinking of T and B cell by the heteroconjugate is believed to bypass the requirement for antigen presentation by MHC molecules (FIG. 17). Thus, these model antigens provides the basis for initial analyses of the immune regulation in anti-CD3-treated mice.

Example 10

Bispecific Ligands

Studies have also been conducted wherein the immunopotentiating effect of employing two monoclonal antibodies linked together to form a single molecule. The antibodies employed in these studies were directed against two distinct but specific epitopes, CD3 and CD4. These epitopes were selected because the anti-CD3 activates T cells, whereas the anti-CD4 focusses the activation towards a specific subset. This conjugate was constructed by crosslinking the respective antibodies using SPD as described in Example 15B hereinbelow.

In the studies which form the basis of the present example, 4 μg of the resultant conjugate, designated F(ab')$_2$ anti-CD3×anti-CD4, was administered to mice i.p. on day 0, and the resultant % of IL-2 receptor$^+$ cells determined by flow cytometry on spleen cells 18 hours post injection. The % of IL-2 receptor$^+$ cells is an indicator of T cell activation. The results of these studies are shown in FIG. 15.

As can be seen, the results shown in FIG. 15 demonstrate that this bispecific antibody construct selectively activates CD4$^+$ cells. Thus, the bispecific antibody conjugate is very highly active in terms of immunopotentiation.

MATERIALS

Example 11

Tumors

The UV-induced skin tumor lines 1591-Pro-4-L, 6139-Pro-1, 1316-Pro-1 and 1591-Var4L were produced as described (50). Tumor cells were passed by serial culture in complete media. For in vivo studies, tumor cells were injected into C3H nude mice. Solid tumors isolated 3 weeks later were cut into 2 mm fragments, and 10 of these fragments were injected into a single subcutaneous location using a 14 gauge, 2 inch long trochar needle. Tumor presence and size were determined at one month in mice. YAC-1 T lymphoma cells and P815 mastocytoma cells were used as targets in some assays in vitro.

Specific antigens may be prepared from tumor cells isolated by serological techniques or suspension dilutions. These antigens were purified by standard methods, for example, density gradient centrifugation or velocity immunosedimentation. The identity of the antigen was confirmed by serology or histological examination. Cells are lysed and used in the assays described in Example 3 to identify unique tumor antigens. Protein extracts are prepared by standard methods including molecular sizing and ion exchange chromatography. Further molecular and biochemical analysis for T specific antigens may be performed by established cloning techniques.

Example 12

Animals

C57BL/10 male mice between 8 to 12 weeks of age were obtained from The Jackson Laboratory, Bar Harbor, Me. A thymic BALB/c mice and NIH Swiss mice were obtained from the National Institutes of Health small animal production facility.

Example 13

Administration of the Heteroconjugate or Immunopotentiating Antibody to Patients In vivo response to OKT3 is shown in FIGS. 5A and B, 11, 12. Patients selected for treatment were those who have histologically documented malignancy which is either evaluable or measurable and for which standard therapy is unavailable. These patients should not have had prior administration of murine antibodies or history of documented or suspected life threatening immune mediated disorders such as asthma. There should not be concurrent drug therapy or infection. Patients should not be pregnant or have either class III or IV cardiac disease. (New York Heart Association Classification) The monoclonal antibody to be administered in a preferred embodiment was Muromonab-CD3 (OKT3), a murine monoclonal antibody directed against the T3 (CD3) antigen of human T cells. This antibody reacts with a 20,000 dalton molecule (CD3) in the membrane of human T cells that has been associated in vitro with the antigen recognition structure of T cells, and which is essential for signal transduction. In the in vitro cytolytic assays, low doses of OKT3 enhances both the generation and function of effector cells. In vivo, anti-CD3 reacts with most peripheral blood T cells and T cells in body tissues but has not been found to react with other hematopoietic elements or other body tissues. It is a potent mitogen in vivo.

The drug was administered through a needle in the contralateral vein by intravenous infusion. Monomurab-CD3 was pushed over 30 to 60 seconds using a 20 cc syringe containing OKT3 dose in 5% human serum albumin. The patient's vital signs were monitored every five minutes for the first fifteen minutes, then at two hours and four hours until twenty-four hour post infusion. Patients received 3 treatments at 2 week intervals unless precluded by toxicity. Toxic response is defined by published criteria.

Orthoclone OKT3 (Muromonab-CD3) sterile solution is a murine monoclonal antibody to the T3 (CD3) antigen of human T cells which functions as an immunosuppressant. The antibody is a biochemically purified IgG2 immunoglobulin with a heavy chain of approximately 50,000 daltons and a light chain of approximately 25,000 daltons. It is directed to a glycoprotein with a molecular weight of 20,000 in the human T cell surface which is essential for T cell function. Because it is a monoclonal antibody preparation, Orthoclone OKT3 sterile solution is a homogenous reproducible antibody product with consistent measurable reactivity to human T cells. Each 5 ml ampule of Orthoclone OKT3 sterile solution contains 5 ml (1 milligram per ml) of Muromonab-CD3 in a clear colorless solution which may contain a few fine translucent protein particles. Each ampule contains a buffer solution (Ph 7.0±0.5) of monobasic sodium phosphate (2.5 ml), sodium sulphate (9.0 mg), sodium chloride (43 mg), and polysorbate 80 (1.0 mg) in water for injection. The proper name Monomurab CD3 is derived from the descriptive "murine monoclonal antibody." The CD3 designation identifies the specificity of the antibody as the cell differentiation (CD) cluster 3 defined by the International Workshop on Leukocyte Differentiation Antigens.

Orthoclone OKT3 is supplied as a sterile solution and packed in 5 ml ampules containing 5 ml of Muromonab-CD3. These vials are stored, refrigerated at 2–8° C. Prior to administration the Orthoclone OKT3 protein solution may develop a few fine translucent particles. These have been shown not to affect its potency. The product is prepared for injection by drawing the solution from the vial into a syringe through a low protein binding 0.2 micrometer filter. The filter is discarded and the needle attached for IV bolus injection. Orthoclone OKT3 is delivered as an IV bolus in less than one minute. This drug should not be administered as an intravenous infusion or in conjunction with other drug solutions. When necessary, Orthoclone OKT3 solution may be diluted with sterile saline.

For the preparation of OKT3 for injection, the antibody was drawn into a syringe as described above. The appropriate dose of OKT3 was then added to 15 to 20 cc 5% human serum albumin in normal saline and placed in a 20 cc syringe. Toxicity was monitored and may include fever and chills, shortness of breath, allergic reaction, chest pains, vomiting, wheezing, nausea, diarrhea or tremors.

Measurement of the effect of CD3 was performed as shown in Table 9.

TABLE 9

Measurement of the Effect of CD3 Treatment on the Immune system

I. Peripheral Leukocyte Phenotype

Total Lymphocyte Count.
Total T-Cell Count.
Total Th and Ts counts. Helper/suppressor
Total NK Cell count.
CD3 and CD25 Expression.

II. Lymphokine Production

Interleukin-2 (IL-2) Level.
Soluble IL-2 receptor - a reflection of T-Cell Activation.
G-CSF and GM-CSF Levels.
TNF Level.

III. Cellular Cytotoxicity.

NK Cell Cytotoxicity on K562 Cell Line at 0 and 24 hours.
LAK Cell Cytotoxicity on Raji Cell Line at 0 and 24 hours.
Pre-LAK Cell (LAK Cell Cytotoxicity After 3-day Culture in IL-2)

IV. Cellular Proliferative Responses.

Anti-CD3 Induced Proliferation.
IL-2 Induced Proliferation.
Unidirectional MLC against pooled, Mitomycin C-Treated Lymphocytes.
PHA- and Con A- induced proliferation.

LAK = Lymphokine activated killer cells

ASSAYS

Example 14

Assays for T Cell Activation

A. Cytotoxicity Assays

Effector cells and $^{51}$Cr-labeled target cells were added to wells of 96-well tissue culture Seroclusters (Costar, Cambridge, Mass.) at various effector to target ratios, in triplicate, in a total volume of 200 µl of complete medium. The monoclonal anti-TcR antibody, 2.4G2 (47), was added to wells at a concentration of 10% cs where indicated. Plates were then incubated for 4 or 6 hours at 37° C. following which 100 µl of supernatant was aspirated and analyzed on a gamma counter (Micromedic Systems, Inc., Horsham, Pa.). Percent specific lysis was calculated by using the formula $[E^{cpm}-S^{cpm}/T^{cpm}-S^{cpm}] \times 100$. $E^{cpm}$ which represents the $^{51}$Cr released from the target cells incubated with effector cells; $T^{cpm}$ represents release of radiolabel from target cells in a 0.05N solution of HCL; $S^{cpm}$ represents background release of target cells cultured in media in the absence of effector cells. In general, the data should represent at least three experiments with identical results. Standard errors for all $^{51}$Cr release values should be less than 5%.

B. Cell-mediated Lympholysis $^{51}$Cr-release Assays

Virus-specific CTL populations were generated in vitro using 5×10$^6$ splenic responder cells mixed with 2.5×10$^6$ irradiated (3300 rad) Vaccinia virus infected syngeneic spleen cells (1 hr., 37° C., multiplicity of injection, 10:1) in 2 ml cultures in complete media (RPMI 1640 supplemented with 10% selected fetal, calf serum (FCS), sodium pyruvate, nonessential amino acids, glutamine, and 2-mercaptoethanol). Cytolytic activity is assayed after 6 days on appropriate virally-infected targets or peptide-pulsed syngeneic or allogeneic $^{51}$Cr-labeled targets.

C. Proliferation and Lymphokine Assays

T cells were cultured in RPMI 1640 medium containing 10% FCS and 2-mercaptoethanol, in the presence or absence of mAbs and/or factors in flat-bottomed microliter 96 wells plates. In some experiments purified anti-CD3 mAb were immobilized on plates as a means of activating cells in the absence of Fc receptor$^+$ cells. After three days, the cells were pulsed with 1 $\mu$Ci [$^3$H] thymidine for 16 hours, the samples were harvested and incorporation of radioactive isotope measured using a scintillation counter. The secretion of soluble lymphokines were monitored by the ability of culture supernatants of activated T cells to support the growth of the lymphokine-dependent HT-2 cell line. $5 \times 10^3$ HT-2 cells were cultured for 24–36 hours with the supernatant to be assayed, then pulsed for 16 hours with 1 $\mu$Ci [$^3$H] thymidine.

This protocol is adaptable in time and cell number when assayed in humans versus animals.

D. Assays of in Vitro Antibody Response

Antibody responses were assayed in vitro by two methods: (1) Plaque forming cells (PFC) responses were measured on the day of culture by assaying TNP, HIV peptide of FITC-conjugated sheep erythrocytes as described (48). Indirect IgG responses were evaluated by blocking the IgM plaques with goat-anti-mouse IgM and developing with a rabbit anti-mouse IgG. (2) Direct binding enzyme-linked immunosorbant assays (ELISA) of FITC, TNP or peptide binding antibodies were carried out as follows. Nunc ELISA plates were coated overnight with 100 $\mu$l of 50 $\mu$g/ml FITC-BSA, TNP-BSA or HIV-peptide-BSA in Voller's buffer (4° C.) Plates were washed extensively with 0.05% Tween 20 diluted in PBS. Free sites were blocked by incubating the plates with 0.5% BSA for 1 hr. at room temperature. One hundred $\mu$l of control or immune sera, diluted in PBS-Tween was added to each well in 3-fold serial dilutions and incubated for 1 hr. After washing, 100 $\mu$l of 1 $\mu$g/well horseradish peroxidase conjugated goat anti-mouse IgG were added. After 1 hr, plates were washed and 100 $\mu$l of peroxidase substrate system were added. This reaction was developed at room temperature for approximately 20 minutes, stopped with 100 $\mu$l of 1% SDS, and read at 415 nm with an automatic ELISA plate reader. ELISA assays was performed by titrating sera, and the optical density (O.D.) values reported will be obtained from a linear portion of the titration curves where O.D. is proportional to sera concentration. Where appropriate, affinity-purified mouse anti-FITC, anti-DNP or HIV antibodies will be prepared, and experimental responses was determined as $\mu$g/ml of antibody based on this standard.

E. Specific Embodiment of Assays for Humans Treated with OKT3

I. CONTROL PROTOCOL

1. Make at least six replicates for control cells.
2. Plate 100,000 cells/well in a total volume of 200 uL.
3. Incubate at 37 deg C. and 5% carbon dioxide for same amount of time as stimulated cells.
4. Add 20 uL of MTT (5 mG/mL in PBS).
5. Incubate for 5 hours at 37 deg C. and 5% carbon dioxide.
6. Centrifuge for 5 minutes at 600×g.
7. Aspirate 160 uL supernatant carefully.
8. Add 160 uL DMSO to each well.
9. Agitate plate for 30 minutes or until all crystals dissolve completely.
10. Read immediately on Multiskan at 550 nm.

II. PATIENT SAMPLE PROTOCOL

1. Make at least six replicates per stimulant.
2. Plate 100,000 cells/well in a total volume of 180 uL.
3. Add stimulant in 20 uL volume to well.
4. Incubate at 37 degrees C. and 5% carbon dioxide.
5. Add 20 uL of MTT (5 mg/mL in PBS).
6. Incubate 5 hours at 37 deg C. and 5% carbon dioxide.
7. Centrifuge at 600×g for 5 minutes.
8. Aspirate 160 uL supernatant carefully.
9. Add 160 uL DMSO to each well.
10. Agitate plate for 30 minutes or until all crystals dissolve completely.
11. Read immediately on Multiskan at 550 nm.

Pre-treatment and 24 hour Time Points:

Put cells in culture as per proliferation assay and triplicate plates with LPS (U plates).

After 18–24 hours, remove 150 uL of cell suspension and freeze suspension and pellets at 70° C.

Assay pellets for tissue factor.

Assay suspension for TNF-$\alpha$ and IL-1$\beta$

Example 15

Biochemical Analysis

Cell surface-labeling with $^{125}$I (Amersham Corp., Arlington Heights, Ill.) was performed by the lactoperoxidase method as described previously (52). Labeled cells were lysed in 1% digitonin buffer, and precleared with hyperimmune rabbit serum. Lysates were immuno-precipitated with anti-CD3 (145-2C11) and protein A agarose beads. Immunoprecipitates were eluted from the protein A agarose in non-reducing sample buffer (containing 2% SDS) and were either directly electrophoresed or reimmunoprecipitated with specific anti-TcR sera prior electrophoresis. The generation of the anti-TcR antisera has been described previously (53). Analyses were performed on 2-dimensional/off-diagonal (2-D) gels (54). Lysates were first subject to electrophoresis under non-reducing conditions in 10% polyacrylamide SDS-PAGE tube gels and were then electrophoresed under reducing conditions (5% 2-ME) on 10% polyacrylamide SDS-PAGE slab gels. Proteins were visualized by autoradiography. Molecular mass determinations were made by comparison to pre-stained high molecular mass standard markers.

Example 16

Coupling the Immunopotentiating Protein to the Second Protein to form a Heteroconjugate For purposes of this invention, any of the various procedures available to form cross-links between proteins can be utilized. The method chosen must not destroy the immunopotentiating activity of the heteroconjugate. Several possible methods are presented below:

A. Biotin-Avidin Coupling

In this method, both of the proteins to be linked are individually coupled to biotin molecules. Avidin then forms a bridge between the biotin molecules, thereby linking the two proteins. This is not a covalent bonding. A variation of the biotin-avidin method is to couple one protein to biotin, the other to avidin, and to mix the two compounds resulting in biotin-avidin links. (41)

B. Coupling Effected by Heterobifunctional Reagents

Whole antibodies or fragments are crosslinked using the heterobifunctional reagent succinimidyl-3-(2-pyridyldithiol) propionate (SPDP) at a 3-fold molar excess SPDP to protein. After crosslinking, a small amount of iodoacetamide is added each sample is applied to a 1.6×90 cm Ultragel AcA 22 (LKB Instruments, Inc., Gaithersburg, Md.) column to remove uncoupled monomers. Functional groups are introduced on each of the proteins to be conjugated so that the predominant reaction when the two substituted proteins are mixed, is between the introduced functional groups. A preferred reagent used for this purpose is N-succinimidyl-3-(2-pyridyldithio) propionate. Disulfide groups are introduced into one of the proteins to be conjugated, and thiol groups are introduced in the other by pyridyldithiolation and subsequent reduction with dithiothreitol. Upon being mixed, the two substituted proteins conjugate by means of a disulfide bond. The details of this method are provided by Carlsson (42). This method has been successfully applied to form antibody-toxin conjugates (43).

C. Cross-linking of Maleimide and SH Groups

SH groups on an one protein are fully alkytated with O-phenylenedimaleimide to provide free maleimide groups. The other protein is reduced to produce SH groups. The two preparations are then cross-linked (44).

D. Peptide-antibody Coupling with Sulfosuccinimidyl 4-(N-Maleimidomethyl) Cyclohexane-1-Carboxylate ("Sulfo-SMCC")

MATERIALS:
1. Antibody to be coupled.
2. Peptide to be coupled.
3. Dithiothreitol
4. Sulfo-SMCC (Pierce 22322)
5. Degassed PBS, pH 7.2.
6. Dialysis tubing with 12,000–14,000 MW cutoff (Spectra/Por 08-667A).
7. SEP-PAK C18 cartridges (Waters 51910).
8. Acetonitrile PROCEDURE:
1. Dialyse 10 mg antibody into 10 ml PBS pH 7.2; degas buffer with vacuum prior to use.
2. Add 10-fold molar excess Sulfo-SMCC and stir for two hours at room temperature.
3. Remove excess Sulfo-SMCC by dialyzing against degassed PBS.
4. Reduce peptide with 100 mM dithiothreitol for one hour at 37 degrees.
5. Remove excess reductant with SEP-PAK C18 cartridge; prewet cartridge with degassed PBS, run reduced peptide over cartridge, and wash with degassed PBS; the reduced peptide will be retained.
6. Elute with 1 ml acetonitrile directly into derivatized antibody while stirring.
7. Incubate for 20 hours at 4 degrees.
8. Remove uncoupled peptide by dialysing against PBS.

E. Peptide-antibody Coupling with 2.2'-Dipyridyl Dithiol (2-PD)

MATERIALS:
1. Antibody to be coupled.
2. Peptide to be coupled.
3. Dithiothreitol
4. 2-PD (Aldrich 14,309-9; "Aldrithiol-2")
5. Sephadex G25 column (Pharmacia 17-0851-01)
6. Degassed PBS, pH 7.2 with EDTA 1 mM.
7. Dialysis tubing with 1000 MW cutoff (Spectra/Por 131084, Spectrum Medical Industries) and with 12,000–14,000 cutoff (Spectra/Por 08-667a).

PROCEDURE:
1. Dialyse antibody into PBS pH 7.2+EDTA 1 mM; degas buffer with vacuum prior to use.
2. Reduce with 250-fold molar excess of dithiothreitol for 1.5 hours at room temperature.
3. Remove excess reductant with Sephadex G25 sizing column (or by dialysis).
4. Add 2-PD in 100-fold molar excess to block newly exposed sulfhydryl groups and monitor reaction by OD at 380 nm or visually by appearance of orange color.
5. Remove excess 2-PD with G25 column (or by dialysis).
6. Concentrate antibody to 10–15 mg/ml.
7. Reduce peptide with DTT as above.
8. Remove reductant from peptide by dialysing against degassed PBS, pH 7.2+1 mM EDTA using 1000 MW cutoff dialysis tubing.
9. Add 5 to 10-fold molar excess of reduced peptide to concentrated antibody; keep total volume small so that the final concentration of antibody is at least 10 mg/ml.
10. Monitor reaction as above.
11. Remove uncoupled peptide by dialysing with standard (MW cutoff 12,000–14,000) dialysis tubing.

OTHER METHODS

Example 17

Cell Separation and Tissue Culture Techniques

General techniques for purifying T cells by cell sorting or antibody and complement treatment routinely performed by published laboratory methods (49) well-known to those skilled in the art.

Example 18

Preparation of a Vaccine

All immune responses are dependent on the ability of T cell to recognize processed antigen associated with major histocompatibility antigens (MHC). Any vaccine approach which utilizes, e.g. HIV peptides or inactivated virus antigen must depend on the ability of antigenic peptides to bind the appropriate MHC antigens necessary to initiate an immune response. Given the tremendous polymorphism of the MHC antigens expressed in the population and the variation of the virus, developing a successful HIV vaccine for general use is difficult.

The efficacy of vaccines, in particular those which may be weakly immunogenic, may be improved by modifying the foreign antigen such that it is more immunogenic, or allowing the use of peptides which are not immunogenic under normal conditions, since they would not bind MHC, but which may constitute a conserved site on the major HIV viral proteins.

Mice are immunized with an amount of heteroconjugate between the amounts of 100 ug and 5 mg added to 30 $\mu$l–1 ml of a physiologic salt solution or Freund's adjuvant (Difco). Alum or pertussis may be added as adjuvants. This solution is then injected into a mammal (mouse, rat, hamster, rabbit) or human to stimulate an immune response against the second protein. Injection may be subcutaneous, or by an intravenous or intramuscular route. Preferred sites for mice are the foot pad or the base of the tail. A booster shot is given 30 days after the primary injection.

To determine if immunity has been successfully induced, delayed skin hypersensitivity or direct tests for antibodies to the amino acid sequence in the second protein of the heteroconjugate, may be performed.

Example 19

Synthetic Peptides

Synthetic peptides corresponding to selected sites are prepared using standard methods of solid-phase peptide synthesis on a Vega 250 peptide synthesizer using double dicyclohexylcarbodimide-mediated couplings (57, 58) and butyloxycarbonyi (Boc)-protected amino acid derivatives. Hydroxybenzotriazole preactivation couplings are performed when coupling glutamine or asparagine. The extent of coupling is monitored using the qualitative ninhydrin test and recoupling is performed when <99.4% coupling is observed. Peptides are cleaved from the resin using the low/high hydrogen fluoride (HF) method (59). For peptide env T2, standard HF cleavage is employed as removal of the tryptophan formyl protecting group is found not to be required for antigenic activity. Peptides are purified to homogeneity by gel filtration and reverse phase HPLC (60). Composition was confirmed and concentration determined by amino acid analysis (61).

Example 20

Purified and Recombinant Proteins

As an example of a protein relevant to HIV, native gp120 is purified from virus-infected cells as described (62). The recombination proteins R10 and PB1 are produced by cloning restriction fragments Kpn I (nucleotide 5923) to Bgl II (nucleotide 7197) or Pvu II (nucleotide 6659) to Bgl II (nucleotide 7197) from the BH10 clone of type III human T-cell lymphotropic virus (HTLV-IIIg) into the Repugen expression vector, followed by expression in *Escherichia coli* and purification as described (63). R10 is initially solubilized in 20 mM Tris-HCl, pH 8.0, with 10 mM 2-mercaptoethanol at 0.22–0.66 mg/mi. B1 is solubilized in 8 M urea at 1.9 mg/ml. Protein R10 represents residues 49–474 of the HTLV-IIIg envelope protein with 25 non-HTLV-III vector-derived residues at the N terminus and 440 such residues at the C terminus. Protein PB1 represents residues 294–474 of gp120 with 30 and 24 non-HTLV-III residues at the N and C termini, respectively. The N-terminal residues of PB1 are partially shared with those of R10, whereas the C-terminal residues are unrelated.

Other desired proteins may be prepared by methods well to those skilled in the art.

Example 21

Models to Test Use of Anti-CD3 as an Immunopotentiating Agent in Anti-Viral and Anti-Tumor Immunity A preclinical huSCID model for an anti-human CD3 and staphylococcus enterotoxin augmented viral and tumor immunity may be developed as a model for the human counterpart, OKT3, or SEB to activate immunity in a similar manner. Initial studies suggested that patients treated with OKT3 develop activated T cells soon after antibody injection. In addition, in other studies, serum from patients have been shown to contain soon after OKT3 injection various lymphokines and cytokines including TNF, γ-interferon, IL-2, and GM-CSF. Therefore, like anti-murine CD3, OKT3 activates T cells in vivo. However, to determine whether in vivo activation of human T cells can lead to immunopotentiation, a model may be developed to examine the OKT3 antibody. SCID mice populated with human T and B cells may be used to study whether OKT3 will potentiate anti-tumor immune responses. Approaches:

a: Development of the huSCID model. Severe combined immunodeficiency (SCID) mice have been developed by Bosma, et al. [49]. These mice contain a genetic defect in a recombinase gene which prevents the expression of mature T cells and B cells. The resulting immunodeficiency allows for the survival of human cells in these mice. One model for studying the function of human T and B cells in reconstituted SCID mice (huSCID) has been developed by Mosier, et al. [50]. In this model, $10^7$ human peripheral blood cells are injected intraperitoneally into SCID mice. Four to six weeks post-injection the lymphoid tissues and peritoneal cavity are examined for the presence of human T cells and B cells. In this model, mice repopulated with human cells have been shown to produce antibodies against diphtheria toxin. Preliminary studies have shown that SCID mice can be reconstituted with human peripheral blood T and B cells as monitored in the peritoneal cavity three to six weeks post-injection. In addition, SCID mice reconstituted with HLA presensitized PBL can reject human skin allografts.

b: Treatment of huSCID mice with OKT3 and tumors. After the huSCID model has been developed, graded doses of OKT3 were injected into engrafted animals. Flow cytometry analysis were used to determine the degree of T cell receptor modulation, depletion, and activation as assessed by IL-2 receptor expression. The serum of treated animals were also examined for the presence of lymphokines and cytokines.

Whereas the invention is susceptible to various modifications and alternative forms, specific embodiments thereof have been shown by way of example in the drawings and are herein described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

REFERENCES

The references listed below are incorporated herein by reference to the extent that they supplement, explain, provide a background for, or teach methodology, techniques, and/or compositions employed herein.

Reference 1. Klein, J. *Immunology: The Science of Self-Nonself Discrimination,* Wiley & Sons, N.Y. (1982).

Reference 2. Leo, O, Foo, M, Sachs, DH, et al. PNAS(USA) 84:1374 (1987).

Reference 3. Weiss, A, Imboden, J, Shoback, D, et al. PNAS (USA) 81:4169 (1984); Hoffman, RW, Bluestone, JA, Leo, OJ, *Immunol;* 135:5 (1985).

Reference 4. Samelson, LE, Harford, JB, Klausner, RD. *Cell* 43:223 (1985).

Reference 5. *Immunology Today,* 10:254 (1989).

Reference 6. Saito, T, Weiss, A, Miller, J, et al. *Nature,* 325:125 (1987); Kranenberg, M, Siu, G, Hood, E L, et al. *Ann. Rev. Immunol* 4:529 (1986).

Reference 7. Starzl, TE, Marchioro, TL, Porter, KA, et al. *Surg. Gynecol. Obstet.* 124;301 (1967).

Reference 8. Sheild, CF, Cosimi, AB, Tolkoff-Rubin, NE, et al. *Transplantation* 28:461 (1979).

Reference 9. Nelson, PW, Cosimi, AB, Delmonico, FL, et al. *Transplantation* 36:587 (1983).

Reference 10. Goldstein, G, *Transpl. Proc.* XIX, No 2, Suppl. 1:1 (1987).

Reference 11. Van Wauwe, JP, de Mey JR, Goossens, JG, *J. Immunol.* 124:2078 (1980);

Reference 12. Leo, O, Foo, M, Henkart, PA, et al. *J. Immumol,* (In Press, 1989).

Reference 13. Takada, S, Engleman, EG, *J. Immunol.* 139:3231 (1987).

Reference 14. Langlet, C, Guimezanes, A, Kaldy, P, et al. *Cytotoxic T cells: Biology and Relevance to Diseases.* eds. Battisto et al. *Ann, NY Acad. Sci.* 532:33 (1988).

Reference 15. Gunther, KC, Malek, TR, Shenvach, EM, *J. Exp. Med.* 159:716 (1984).

Reference 16. Leo, O, Foo, M, Henkart, PA, et al. *J. Immunol.* 139:3556 (1987).

Reference 17. White, J, Herman, A, Pullen, AM, et al. *Cell.* 56:27 (1989).

Reference 18. Rosenberg, SA, Lotze, MF, Muul, LM, et al. *N. Eng. J. Med.* 316:889 (1987).

Reference 19. Topalian, SL, Solomon, D, Avis, FP, et al. *J. Clin. Onc.* 6:839 (1988).

Reference 20. Gallo, RC, *J. Acquir, Immune Defic. Syndr.* 1:521 (1988).

Reference 21. *J. NIH Research,* v 1 pp. 30,50–52, May–June (1989).

Reference 22. Infra

Reference 23. Hirsch, R, Gress, R, Pluznik, D, et al. *J. Immunol.* 142:737 (1989).

Reference 24. Infra.

Reference 25. Leo, O, Foo, M, Sachs, DH et al. *PNAS,* (USA) 84:1374 (1987).

Reference 26. Hirsch, R, Gress, R, Pluznik; D, et al. *J. Immunol.* 142:737 (1989).

Reference 27. Meuer, SC, Hodgdon, JC, Hussey, RE, et al. *J Exp. Med.* 158; 988 (1984).

Reference 28. Ellenhorn, JDI, Hirsch, R, and Schreiber, H, Bluestone, JA, *Science* 242:569 (1988).

Reference 29. Leo, O, Foo, M, Sachs, DH, et al. *PNAS.,* (USA), 84:1374 (1987).

Reference 30. Infra.

Reference 31. White, J, Herman, A, Pullen, AM, et al. *Cell,* 56:27 (1989).

Reference 32. Leo et al Supra.

Reference 33. Hoffman, RW, Bluestone, JA, Leo, O et al. *J. Immunol.* 135:5 (1985).

Reference 34. Leo, O, Foo, M, Segal, DM et al., *J. Immunol,* 139:1214 (1988).

Reference 35. Leo, O, Foo, M, Henkart, PA, et al., *J. Immunol* (In Press, 1989).

Reference 36. Hirsch, R, Gress, RE, Pluznik, DH, *J. Immunol,* 142:737 (1989).

Reference 37. Samuelson, LE, Germain, RN, Schwartz, RH, PNAS(USA) 80:6972 (1983).

Reference 38. White, J, Herman, A, Pullen, AM, et al. *Cell* 56:27 (1989).

Reference 39. Kappler, J, Kotzin, B, Herron, L, et al., *Science* 244:811 (1989).

Reference 40. Klein, supra, pp 251–253.

Reference 41. Green, NM, et al. *Adv. in Prot, Chem.,* (ed.) Afinsen, CB, et al 29:85 (1975); Boyer, EA, Wilchek, M, *Meth. in Biochem Anal.* 26:1 (1980).

Reference 42. Carlsson, J, Drevin, H, Axen, R. *Biochem J.* 173:723 (1978).

Reference 43. Cumber, AJ, Forrester, JA, Foxwell, BMJ, et al. *Methods in Enzymology* 112:207 (1985).

Reference 44. Glennie, MJ, McBride, HM, Worth, AT, et al., *J. Immunol.* 139:2367 (1987). Reference 45. Bluestone, J. A., *Proc. 15th Intl. Leuk. Cult. Conf.,* eds. Parker, J. W. and O'Brien, R. L., Wiley, Sussex, U.K., pp. 149–152 (1983)

Reference 46. Krieger, J, Jenis, DM, Chesnut, RW et al., *J. Immunol.* 140:388 (1988).

Reference 47. Unkeless, JC, *J. Exp. Med.* 150:580 (1979).

Reference 48. Asano, Y, Singer, A, Hodes, RJ, *J. Exp. Med.* 154:1100 (1981).

Reference 49. Leo, O, Sachs, DH, Samelson, L, et al. *J. Immunol.* 137:3874 (1986).

Reference 50. Von Waes, C, Urban, JL, Rothstein, JL, et al. *J. Exp. Med.* 164:1547 (1986); Strauss, HJ, Von Waes, C, Fink, MA, et al. *J. Exp Med* 164:1516 (1986).

Reference 51. Kast, WM, Bluestone, JA, Spaargaren, J. et al. *Nature* (submitted, 1989).

Reference 52. Samelson, LE, Harford, JB, Klausner, RD, *Cell* 43:223 (1985).

Reference 53. Sussman, J Bonifacino, JS, Lippencott-Schwartz, J et al., *Cell* 52:85 (1988).

Reference 54. Wortzel, RD, Philipps, C, Schreiber, H, *Nature* (Lond.) 304:165 (1983).

Reference 55. White, J Hermon, A, Pullen, AM et al. *Cell* 56:27 (1989).

Reference 56. Kappler, J, Kotzin, B. Herron, L, et al., *Science* 244:811 (1989).

Reference 57. Merrifield, RB, *J Am Chem Soc* 85:2149 (1963).

Reference 58. Stewart, JM, Young, JD, *Solid Phase Peptide Synthesis* (Pierce), Rockford, Ill., (1984).

Reference 59. Tam, JP, Heath, WF, Merrifield, RB, *J Am. Chem. Soc.* 105:6442 (1983).

Reference 60. Cease, KB, Berkower, J, York-Jolly, J et al., *J. Exp. Med.* 164:1779 (1986).

Reference 61. Cease, KB, Margalit, H, Cornette, JL, et al., PNAS(USA), 84:4249 (1987).

Reference 62. Robey, WG, Arthur, LO, Matthews, TJ, et al., PNAS(USA) 83:7023 (1986).

Reference 63. Putney, SD, Matthews, TJ, Robey, WG, et al., *Science* 234:1392 (1986).

Reference 64. Gajewski, T. Goldwasser, G. and F. W. Fitch. (1988) *J. Immunol.* 139:1348–1353.

Reference 65. Leo O, Foo M, Sachs DH, Samelson LE, Bluestone, JA (1987) *Proc. Natl. Acad Sci. USA,* 84:1374.

Reference 66. Jenkins, M. K., Pardoll, D., Mizuguchi, J., Chused, T. M., and R. Schwartz. (1987) *Proc. Natl. Acad. Sci. USA* 84:5409–5413.

Reference 67. Klausner, R. D., O'Shea, J. J., Luong, H., Ross, P., Bluestone, J. A. and Samelson, L. E. (1987) *J. Biological Chemistry* 262:12654–12659.

Reference 68. June, C. R., Martin, P. J., Spooner, C. E., Hansen, J. A., Meier, K. E. (1986) *J. Immunol.* 136:3945–3952.

Reference 69. Yang, S. Y., Chouaib, S., DuPont, B (1986) *J. Immunol.* 137:1097–1100.

Reference 70. Hayward, A., Roylston, A., Beverley, P. (1988) *Immunol.* 64:87–92.

What is claimed is:

1. A method of preparing immunological products, comprising the steps of:

(a) immunizing a mammal with:

an immunopotentiating composition comprising an immunopotentiating amount of anti-CD3 monoclonal antibody and an antigen; and (b) obtaining immunological products from said immunized mammal, said products including T cell, B cells or antibodies, wherein said products are directed against said antigen.

2. The method of claim 1, wherein said immunological products comprise antibodies, and the method further comprises preparing a gamma globulin fraction from said antibodies.

3. The method of claim 1, wherein said mammal is a human.

4. The method of claim 1, wherein the anti-CD3 monoclonal antibody comprises a soluble anti-CD3 monoclonal antibody.

5. The method of claim 1, wherein said immunological products comprise antibodies.

6. The method of claim 5, further comprising preparing a gamma globulin fraction from said antibodies.

7. The method of claim 1, wherein the anti-CD3 monoclonal antibody is conjugated to the antigen.

8. The method of claim 1, wherein said antigen is a protein.

9. The method of claim 8, wherein said protein is derived from a tumor, a virus, a bacteria, a fungus, or a protozoal or metazoal parasite.

10. The method of claim 9, wherein said protein is tumor-specific, tumor-associated, viral-specific, or viral-associated.

11. The method of claim 1, wherein said antigen is a non-protein molecule selected from a group consisting of glycolipids, carbohydrates, and lectins.

12. A method of preparing antibodies, comprising the steps of:
   (a) immunizing mammals with:
      an immunopotentiating composition comprising an immunopotentiating amount of anti-CD3 monoclonal antibody and an antigen; and
   (b) obtaining antibodies from said immunized mammal directed against said antigen.

13. The method of claim 12, wherein the antigen is a protein.

14. The method of claim 12, wherein the anti-CD3 monoclonal antibody comprises a soluble anti-CD3 monoclonal antibody.

15. The method of claim 12, wherein the anti-CD3 monoclonal antibody is conjugated to the antigen.

16. The method of claim 12, wherein said mammal is a human.

17. The method of claim 13, wherein said protein is derived from a tumor, a virus, a bacteria, a fungus, or a protozoal or metazoal parasite.

18. The method of claim 17, wherein said protein is tumor-specific, tumor-associated, viral-specific, or viral-associated.

19. The method of claim 12, wherein said antigen is a non-protein molecule selected from a group consisting of glycolipids, carbohydrates, and lectins.

20. A method of producing immunological products in a mammal, comprising the steps of:
   (a) immunizing the mammal with:
      an immunopotentiating composition comprising an immunopotentiating amount of anti-CD3 monoclonal antibody and an antigen; and
   (b) producing immunological products in said immunized mammal, said products including T cell, B cells or antibodies, wherein said products are directed against said antigen.

21. The method of claim 20, wherein the anti-CD3 monoclonal antibody comprises a soluble anti-CD3 monoclonal antibody.

22. The method of claim 20, wherein the anti-CD3 monoclonal antibody is conjugated to the antigen.

23. The method of claim 20, wherein said mammal is a human.

24. The method of claim 20, wherein the antigen is a protein.

25. The method of claim 24, wherein said protein is derived from a tumor, a virus, a bacteria, a fungus, or a protozoal or metazoal parasite.

26. The method of claim 25, wherein said protein is tumor-specific, tumor-associated, viral-specific, or viral-associated.

27. The method of claim 20, wherein said antigen is a non-protein molecule selected from a group consisting of glycolipids, carbohydrates, and lectins.

* * * * *